(12) United States Patent
Sasada et al.

(10) Patent No.: US 11,532,790 B2
(45) Date of Patent: Dec. 20, 2022

(54) COMPOSITION AND LIGHT EMITTING DEVICE USING THE SAME

(71) Applicant: Sumitomo Chemical Company, Limited, Tokyo (JP)

(72) Inventors: Toshiaki Sasada, Tsukuba (JP); Naoki Hayashi, Osaka (JP); Shinichi Inakazu, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 404 days.

(21) Appl. No.: 16/500,872

(22) PCT Filed: Apr. 20, 2018

(86) PCT No.: PCT/JP2018/016308
§ 371 (c)(1),
(2) Date: Oct. 4, 2019

(87) PCT Pub. No.: WO2018/198973
PCT Pub. Date: Nov. 1, 2018

(65) Prior Publication Data
US 2020/0044156 A1    Feb. 6, 2020

(30) Foreign Application Priority Data

Apr. 27, 2017  (JP) .............................. JP2017-088007

(51) Int. Cl.
*C07D 209/86* (2006.01)
*H01L 51/00* (2006.01)
(Continued)

(52) U.S. Cl.
CPC ........ *H01L 51/0043* (2013.01); *C07D 209/86* (2013.01); *C07D 219/02* (2013.01); *C07D 279/22* (2013.01); *C07D 307/91* (2013.01); *C07D 333/76* (2013.01); *C07F 15/0033* (2013.01); *C08G 61/12* (2013.01); *C09K 11/06* (2013.01); *H01L 51/0039* (2013.01); *H01L 51/0056* (2013.01); *H01L 51/0058* (2013.01); *H01L 51/0071* (2013.01); *H01L 51/0072* (2013.01); *H01L 51/0073* (2013.01); *H01L 51/0074* (2013.01); *H01L 51/0085* (2013.01); *C08G 2261/124* (2013.01); *C08G 2261/148* (2013.01); *C08G 2261/1412* (2013.01);
(Continued)

(58) Field of Classification Search
None
See application file for complete search history.

(56) References Cited

U.S. PATENT DOCUMENTS

2012/0068170 A1   3/2012   Pflumm et al.
2012/0168735 A1   7/2012   Pflumm et al.
(Continued)

FOREIGN PATENT DOCUMENTS

CN   102870248 A   1/2013
CN   102911145 A   2/2013
(Continued)

OTHER PUBLICATIONS

Office Action dated Jun. 23, 2021 in CN Application No. 201880027265.7.
Extended European Search Report dated Dec. 3, 2020 in EP Application No. 18791375.1.
International Search Report dated Jul. 17, 2018 in International Application No. PCT/JP2018/016308.
Written Opinion dated Jul. 17, 2018 in International Application No. PCT/JP2018/016308.
Office Action dated Mar. 15, 2019 in JP Application No. 2018568994.
Office Action dated Sep. 22, 2022 in KR Application No. 10-2019-7034215.
Office Action dated Sep. 28, 2022 in EP Application No. 18791375.1.

* cited by examiner

*Primary Examiner* — Robert S Loewe
(74) *Attorney, Agent, or Firm* — Panitch Schwarze Belisario & Nadel LLP

(57) ABSTRACT

A composition which is useful for producing a light emitting device having excellent external quantum efficiency contains two or more compounds represented by the formula (C-1) and a phosphorescent compound, in which at least one of the compounds represented by the formula (C-1) is a compound in which $R^C$ is a group represented by the formula (C'-1).

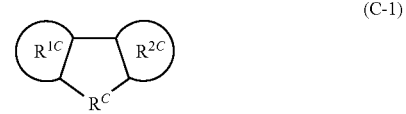

(C-1)

Ring $R^{1C}$ and Ring $R^{2C}$ represent an aromatic hydrocarbon ring or an aromatic hetero ring. $R^C$ represents an oxygen atom, a sulfur atom or a group represented by the formula (C'-1).

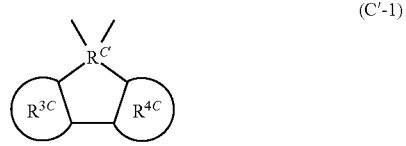

(C'-1)

Ring $R^{3C}$ and Ring $R^{4C}$ represent an aromatic hydrocarbon ring or an aromatic hetero ring. $R^{C'}$ represents a carbon atom, a silicon atom, a germanium atom, a tin atom or a lead atom.

12 Claims, No Drawings

(51) Int. Cl.
*C07D 219/02* (2006.01)
*C07D 279/22* (2006.01)
*C07D 307/91* (2006.01)
*C07D 333/76* (2006.01)
*C07F 15/00* (2006.01)
*C08G 61/12* (2006.01)
*C09K 11/06* (2006.01)
*H01L 51/50* (2006.01)

(52) U.S. Cl.
CPC . *C08G 2261/1414* (2013.01); *C08G 2261/18* (2013.01); *C08G 2261/228* (2013.01); *C08G 2261/312* (2013.01); *C08G 2261/3142* (2013.01); *C08G 2261/3162* (2013.01); *C08G 2261/512* (2013.01); *C08G 2261/95* (2013.01); *C09K 2211/1029* (2013.01); *C09K 2211/1044* (2013.01); *C09K 2211/185* (2013.01); *H01L 51/5016* (2013.01); *H01L 51/5056* (2013.01)

(56) References Cited

U.S. PATENT DOCUMENTS

| | | | |
|---|---|---|---|
| 2012/0228552 A1* | 9/2012 | Parham | H01L 51/0072 544/212 |
| 2013/0037791 A1 | 2/2013 | Horiuchi et al. | |
| 2013/0221340 A1 | 8/2013 | Kamatani et al. | |
| 2015/0236278 A1 | 8/2015 | Bryman et al. | |
| 2016/0056393 A1 | 2/2016 | Oikawa et al. | |
| 2016/0285003 A1 | 9/2016 | Gaudin et al. | |
| 2017/0141328 A1 | 5/2017 | Hayer et al. | |
| 2018/0026209 A1 | 1/2018 | Stoessel et al. | |
| 2019/0185411 A1* | 6/2019 | Lee | C07D 409/14 |
| 2020/0098996 A1* | 3/2020 | Koenen | H01L 51/006 |
| 2022/0093870 A1* | 3/2022 | Mun | H01L 51/0054 |

FOREIGN PATENT DOCUMENTS

| | | |
|---|---|---|
| EP | 3001474 A1 | 3/2016 |
| JP | 2011249754 A | 12/2011 |
| JP | 2012102024 A | 5/2012 |
| JP | 2013527989 A | 7/2013 |
| KR | 10-2017-0018946 A | 2/2017 |
| WO | 2012048820 A1 | 4/2012 |
| WO | 2013045410 A1 | 4/2013 |
| WO | 2014085296 A1 | 6/2014 |
| WO | 2014136213 A1 | 9/2014 |
| WO | 2014163083 A1 | 10/2014 |
| WO | 2015071473 A1 | 5/2015 |
| WO | 2016124304 A1 | 8/2016 |

COMPOSITION AND LIGHT EMITTING DEVICE USING THE SAME

CROSS-REFERENCE TO RELATED APPLICATIONS

This application is a Section 371 of International Application No. PCT/JP2018/016308, filed Apr. 20, 2018, which was published in the Japanese language on Nov. 1, 2018 under International Publication No. WO 2018/198973 A1, which claims priority under 35 U.S.C. § 119(b) to Japanese Application No. 2017-088007, filed Apr. 27, 2017, the disclosures of which are incorporated herein by reference in their entirety.

TECHNICAL FIELD

The present invention relates to a composition and a light emitting device using the same.

BACKGROUND ART

Light emitting devices such as organic electroluminescent devices and the like can be suitably used for display and lighting applications. As a light emitting material used for a light emitting layer of a light emitting device, for example, a composition containing a compound (H0) and FIrpic has been proposed (Patent Document 1).

[Chemical Formula 1]

compound (H0)

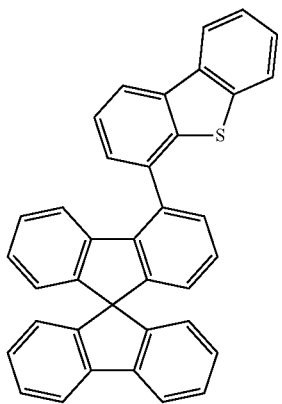

FIrpic

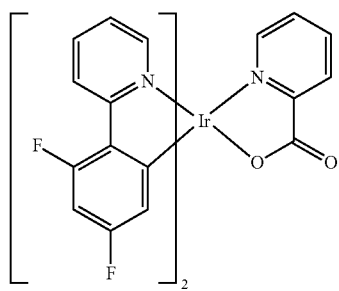

PRIOR ART DOCUMENT

Patent Document

[Patent Document 1]
Chinese Patent Application Publication No. 102911145

SUMMARY OF THE INVENTION

Problem to be Solved by the Invention

However, a light emitting device produced using the above-described composition was not necessarily sufficient in external quantum efficiency. Then, the present invention has an object of providing a composition which is useful for production of a light emitting device excellent in external quantum efficiency.

Means for Solving the Problem

The present invention provides the following [1] to [11].
[1] A composition comprising two or more compounds represented by the formula (C-1) and a phosphorescent compound, wherein
at least one of the above-described two or more compounds represented by the formula (C-1) is a compound represented by the formula (C-1) in which $R^C$ is a group represented by the formula (C'-1):

[Chemical Formula 2]

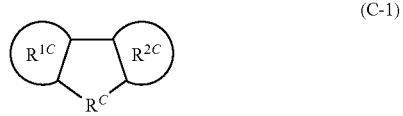

(C-1)

[wherein,
Ring $R^{1C}$ and Ring $R^{2C}$ each independently represent an aromatic hydrocarbon ring or an aromatic hetero ring, and the foregoing rings optionally have a substituent. When a plurality of the substituents are present, they may be combined together to form a ring together with the atoms to which they are attached.
$R^C$ represents an oxygen atom, a sulfur atom or a group represented by the formula (C'-1).]

[Chemical Formula 3]

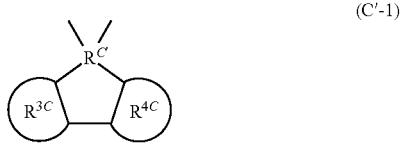

(C'-1)

[wherein,
Ring $R^{3C}$ and Ring $R^{4C}$ each independently represent an aromatic hydrocarbon ring or an aromatic hetero ring, and the foregoing rings optionally have a substituent. When a plurality of the substituents are present, they may be combined together to form a ring together with the atoms to which they are attached.
$R^{C'}$ represents a carbon atom, a silicon atom, a germanium atom, a tin atom or a lead atom.].

[2] The composition according to [1], wherein the above-described compound represented by the formula (C-1) in which $R^C$ is a group represented by the formula (C'-1) is a compound represented by the formula (C-2-1):

[Chemical Formula 4]

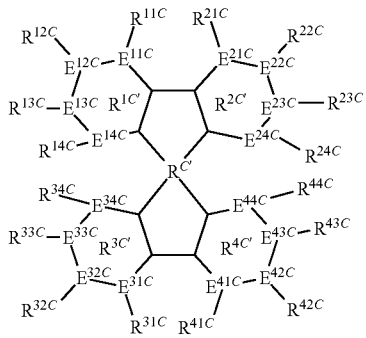

(C-2-1)

[wherein, $R^{C'}$ represents the same meaning as described above.

$E^{11C}$, $E^{12C}$, $E^{13C}$, $E^{14C}$, $E^{21C}$, $E^{22C}$, $E^{23C}$, $E^{24C}$, $E^{31C}$, $E^{32C}$, $E^{33C}$, $E^{34C}$, $E^{41C}$, $E^{42C}$, $E^{43C}$ and $E^{44C}$ each independently represent a nitrogen atom or a carbon atom.

Ring $R^{1C'}$, Ring $R^{2C'}$, Ring $R^{3C'}$ and Ring $R^{4C'}$ each independently represent a benzene ring, a pyridine ring or a diazabenzene ring.

$R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent.

When $E^{11C}$ is a nitrogen atom, $R^{11C}$ is absent. When $E^{12C}$ is a nitrogen atom, $R^{12C}$ is absent. When $E^{13C}$ is a nitrogen atom, $R^{13C}$ is absent. When $E^{14C}$ is a nitrogen atom, $R^{14C}$ is absent. When $E^{21C}$ is a nitrogen atom, $R^{21C}$ is absent. When $E^{22C}$ is a nitrogen atom, $R^{22C}$ is absent. When $E^{23C}$ is a nitrogen atom, $R^{23C}$ is absent. When $E^{24C}$ is a nitrogen atom, $R^{24C}$ is absent. When $E^{31C}$ is a nitrogen atom, $R^{31C}$ is absent. When $E^{32C}$ is a nitrogen atom, $R^{32C}$ is absent. When $E^{33C}$ is a nitrogen atom, $R^{33C}$ is absent. When $E^{34C}$ is a nitrogen atom, $R^{34C}$ is absent. When $E^{41C}$ is a nitrogen atom, $R^{41C}$ is absent. When $E^{42C}$ is a nitrogen atom, $R^{42C}$ is absent. When $E^{43C}$ is a nitrogen atom, $R^{43C}$ is absent. When $E^{44C}$ is a nitrogen atom, $R^{44C}$ is absent.

$R^{11C}$ and $R^{12C}$, $R^{12C}$ and $R^{13C}$, $R^{13C}$ and $R^{14C}$, $R^{14C}$ and $R^{34C}$, $R^{34C}$ and $R^{33C}$, $R^{33C}$ and $R^{32C}$, $R^{32C}$ and $R^{31C}$, $R^{31C}$ and $R^{41C}$, $R^{41C}$ and $R^{42C}$, $R^{42C}$ and $R^{43C}$, $R^{43C}$ and $R^{44C}$, $R^{44C}$ and $R^{24C}$, $R^{24C}$ and $R^{23C}$, $R^{23C}$ and $R^{22C}$, $R^{22C}$ and $R^{21C}$, and $R^{21C}$ and $R^{11C}$ may each be combined together to form a ring together with the carbon atoms to which they are attached.].

[3] The composition according to [1] or [2], wherein at least one of the above-described two or more compounds represented by the formula (C-1) is a compound represented by the formula (C-2-2):

[Chemical Formula 5]

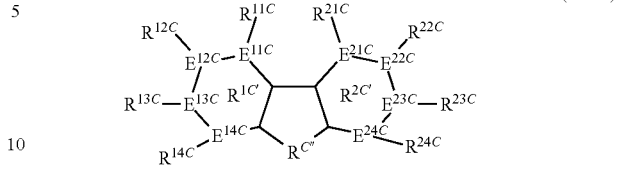

(C-2-2)

[wherein, $R^{C''}$ represents an oxygen atom or a sulfur atom.

$E^{11C}$, $E^{12C}$, $E^{13C}$, $E^{14C}$, $E^{21C}$, $E^{22C}$, $E^{23C}$ and $E^{24C}$ each independently represent a nitrogen atom or a carbon atom.

Ring $R^{1C'}$ and Ring $R^{2C'}$ each independently represent a benzene ring, a pyridine ring or a diazabenzene ring.

$R^{11C}$, $R^{12C}$, $R^{13C}$, $R^{14C}$, $R^{21C}$, $R^{22C}$, $R^{23C}$ and $R^{24C}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent.

When $E^{11C}$ is a nitrogen atom, $R^{11C}$ is absent. When $E^{12C}$ is a nitrogen atom, $R^{12C}$ is absent. When $E^{13C}$ is a nitrogen atom, $R^{13}$: is absent. When $E^{14C}$ is a nitrogen atom, $R^{14C}$ is absent. When $E^{21C}$ is a nitrogen atom, $R^{21C}$ is absent. When $E^{22C}$ is a nitrogen atom, $R^{22C}$ is absent. When $E^{23C}$ is a nitrogen atom, $R^{23C}$ is absent. When $E^{24C}$ is a nitrogen atom, $R^{24C}$ is absent.

$R^{11C}$ and $R^{12C}$, $R^{12C}$ and $R^{13C}$, $R^{13C}$, and $R^{14C}$, $R^{24C}$ and $R^{23C}$, $R^{23C}$ and $R^{22C}$, $R^{22C}$ and $R^{21C}$, and $R^{21C}$ and $R^{11C}$ may each be combined together to form a ring together with the carbon atoms to which they are attached.].

[4] The composition according to [2] or [3], wherein the above-described compound represented by the formula (C-2-1) is a compound represented by the formula (C-3-1):

[Chemical Formula 6]

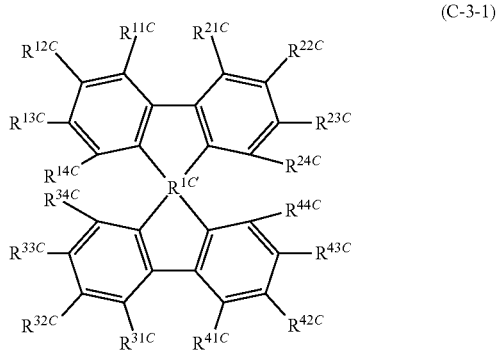

(C-3-1)

[wherein, $R^{C'}$, $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ represent the same meaning as described above.].

[5] The composition according to [3] or [4], wherein the above-described compound represented by the formula (C-2-2) is a compound represented by the formula (C-3-2):

[Chemical Formula 6]

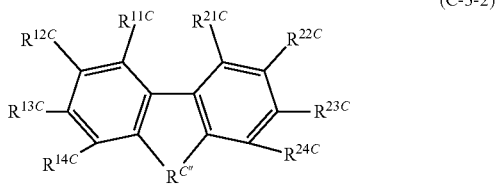

(C-3-2)

[wherein, $R^{C''}$, $R^{11C}$, $R^{12C}$, $R^{13C}$, $R^{14C}$, $R^{21C}$, $R^{22C}$, $R^{23C}$ and $R^{24C}$ represent the same meaning as described above.].

[6] The composition according to any one of [1] to [5], wherein the above-described phosphorescent compound is a phosphorescent compound represented by the formula (1):

[Chemical Formula 8]

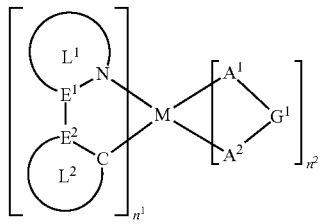

(1)

[wherein,

M represents a ruthenium, a rhodium atom, a palladium atom, an iridium atom or a platinum atom.

$n^1$ represents an integer of 1 or more, $n^2$ represents an integer of 0 or more. $n^1+n^2$ is 3 when M is a ruthenium, a rhodium atom or an iridium atom, while $n^1+n^2$ is 2 when M is a palladium atom or a platinum atom.

$E^1$ and $E^2$ each independently represent a carbon atom or a nitrogen atom. At least one of $E^1$ and $E^2$ is a carbon atom. When a plurality of $E^1$ and $E^2$ are present, they may be the same or different at each occurrence.

Ring $L^1$ represents an aromatic hetero ring, and this aromatic hetero ring optionally has a substituent. When a plurality of the substituents are present, they may be combined together to form a ring together with the atoms to which they are attached. When a plurality of Ring $L^1$ are present, they may be the same or different.

Ring $L^2$ represents an aromatic hydrocarbon ring or an aromatic hetero ring, and the foregoing rings optionally have a substituent. When a plurality of the substituents are present, they may be combined together to form a ring together with the atoms to which they are attached. When a plurality of Ring $L^2$ are present, they may be the same or different.

The substituent which Ring $L^1$ optionally has and the substituent which Ring $L^2$ optionally has may be combined together to form a ring together with the atoms to which they are attached.

$A^1$-$G^1$-$A^2$ represents an anionic bidentate ligand. $A^1$ and $A^2$ each independently represent a carbon atom, an oxygen atom or a nitrogen atom, and these atoms may be a ring constituent atom. $G^1$ represents a single bond or an atomic group constituting a bidentate ligand together with $A^1$ and $A^2$. When a plurality of $A^1$-$G^1$-$A^2$ are present, they may be the same or different.].

[7] The composition according to [6], wherein the above-described phosphorescent compound represented by the formula (1) is a phosphorescent compound represented by the formula (1-B):

[Chemical Formula 9]

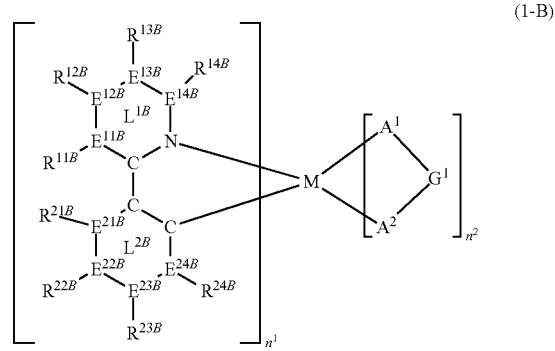

(1-B)

[wherein,

M, $n^1$, $n^2$ and $A^1$-$G^1$-$A^2$ represent the same meaning as described above.

$E^{11B}$, $E^{12B}$, $E^{13B}$, $E^{14B}$, $E^{21B}$, $E^{22B}$, $E^{23B}$ and $E^{24B}$ each independently represent a nitrogen atom or a carbon atom. When a plurality of $E^{11B}$, $E^{12B}$, $E^{13B}$, $E^{14B}$, $E^{21B}$, $E^{22B}$, $E^{23B}$ and $E^{24}B$ are present, they may be the same or different at each occurrence. When $E^{11B}$ is a nitrogen atom, $R^{11B}$ is absent. When $E^{12B}$ is a nitrogen atom, $R^{12B}$ is absent. When $E^{13B}$ is a nitrogen atom, $R^{13B}$ is absent. When $E^{14B}$ is a nitrogen atom, $R^{14B}$ is absent. When $E^{21B}$ is a nitrogen atom, $R^{21B}$ is absent. When $E^{22B}$ is a nitrogen atom, $R^{22B}$ is absent. When $E^{23B}$ is a nitrogen atom, $R^{23B}$ is absent. When $E^{24B}$ is a nitrogen atom, $R^{24B}$ is absent.

$R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. When a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence. $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ may each be combined together to form a ring together with the atoms to which they are attached.

Ring $L^3$ represents a pyridine ring or a diazabenzene ring.

Ring $L^{2B}$ represents a benzene ring, a pyridine ring or a diazabenzene ring.].

[8] The composition according to [7], wherein the above-described phosphorescent compound represented by the formula (1-B) is a phosphorescent compound represented by the formula (1-B1), a phosphorescent compound represented by the formula (1-B2), a phosphorescent compound represented by the formula (1-B3), a phosphorescent compound represented by the formula (1-B4) or a phosphorescent compound represented by the formula (1-B5):

[Chemical Formula 10]

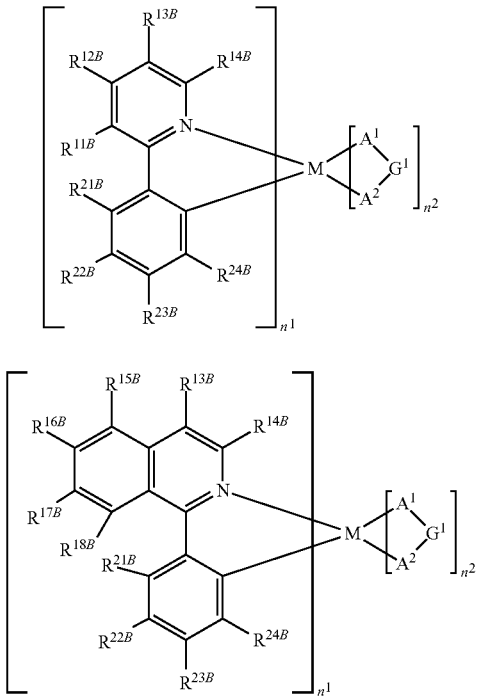

(1-B1)

(1-B2)

(1-B3)

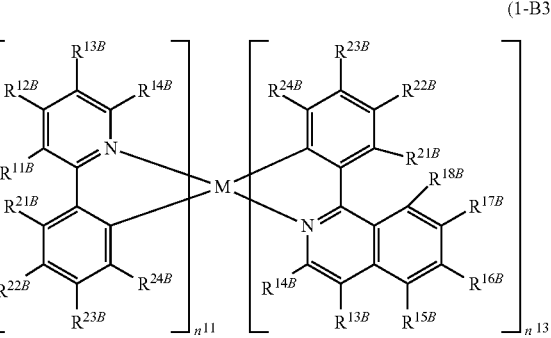

(1-B4)

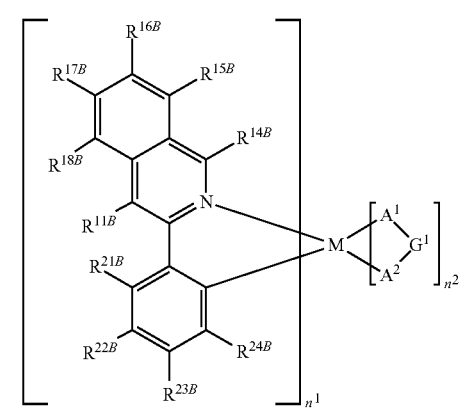

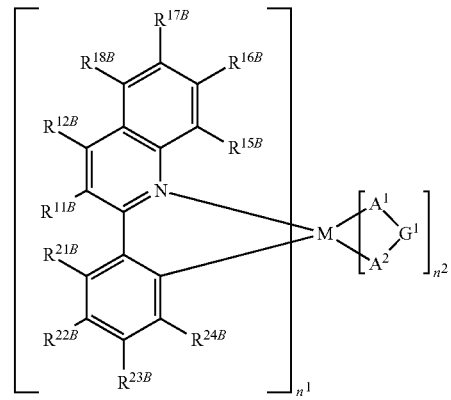

(1-B5)

[wherein,

M, $n^1$, $n^2$, $A^1$-$G^1$-$A^2$, $R^{11B}$, $R^{12B}$, $R^{13B}$, $R^{14B}$, $R^{21B}$, $R^{22B}$, $R^{23B}$ and $R^{24B}$ represent the same meaning as described above.

$n^{11}$ and $n^{12}$ each independently represent an integer of 1 or more. $n^{11}+n^{12}$ is 3 when M is a ruthenium, a rhodium atom or an iridium atom, while $n^{11}+n^{12}$ is 2 when M is a palladium atom or a platinum atom.

$R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. When a plurality of $R^{15B}$, $R^{16B}$, $R^{17B}$ and $R^{18B}$ are present, they may be the same or different at each occurrence. $R^{13B}$ and $R^{15B}$, $R^{15B}$ and $R^{16B}$, $R^{16B}$ and $R^{17B}$, $R^{17B}$ and $R^{18B}$, and $R^{18B}$ and $R^{21B}$ may each be combined together to form a ring together with the atoms to which they are attached.].

[9] The composition according to [6], wherein the above-described phosphorescent compound represented by the formula (1) is a phosphorescent compound represented by the formula (1-A):

[Chemical Formula 11]

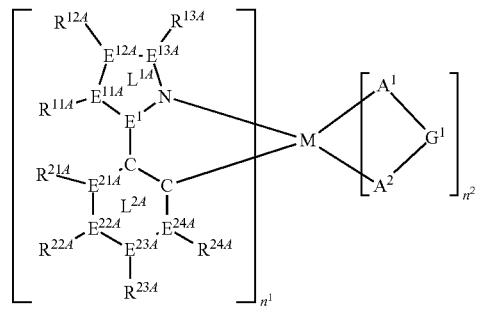

(1-A)

[wherein,

M, $n^1$, $n^2$, $E^1$ and $A^1$-$G^1$-$A^2$ represent the same meaning as described above.

$E^{11A}$, $E^{12A}$, $E^{13A}$, $E^{21A}$, $E^{22A}$, $E^{23A}$ and $E^{24A}$ each independently represent a nitrogen atom or a carbon atom. When a plurality of $E^{11A}$, $E^{12A}$, $E^{13A}$, $E^{21A}$, $E^{22A}$, $E^{23A}$ and $E^{24A}$ are present, they may be the same or different at each occurrence. When $E^{11A}$ is a nitrogen atom, $R^{11A}$ may be present or absent. When $E^{12A}$ is a nitrogen atom, $R^{12A}$ may be present or absent. When $E^{13A}$ is a nitrogen atom, $R^{3A}$ may be present or absent. When $E^{21A}$ is a nitrogen atom, $R^{21A}$ is absent. When $E^{22A}$ is a nitrogen atom, $R^{22A}$ is absent. When $E^{23A}$ is a nitrogen atom, $R^{23A}$ is absent. When $E^{24A}$ is a nitrogen atom, $R^{24A}$ is absent.

$R^{11A}$, $R^{12A}$, $R^{13A}$, $R^{21A}$, $R^{22A}$, $R^{23A}$ and $R^{24A}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. When a plurality of $R^{11A}$, $R^{12A}$, $R^{13A}$, $R^{21A}$, $R^{22A}$, $R^{23A}$ and $R^{24A}$ are present, they may be the same or different at each occurrence. $R^{11A}$ and $R^{12A}$, $R^{12A}$ and $R^{13A}$, $R^{11A}$ and $R^{21A}$, $R^{21A}$ and $R^{22A}$, $R^{22A}$ and $R^{23A}$, and $R^{23A}$ and $R^{24A}$ may each be combined together to form a ring together with the atoms to which they are attached.

Ring $L^{1A}$ represents a diazole ring.

Ring $L^{2A}$ represents a benzene ring, a pyridine ring or a diazabenzene ring.].

[10] The composition according to [9], wherein the above-described phosphorescent compound represented by the formula (1-A) is a phosphorescent compound represented by the formula (1-A4) or a phosphorescent compound represented by the formula (1-A5):

[Chemical Formula 12]

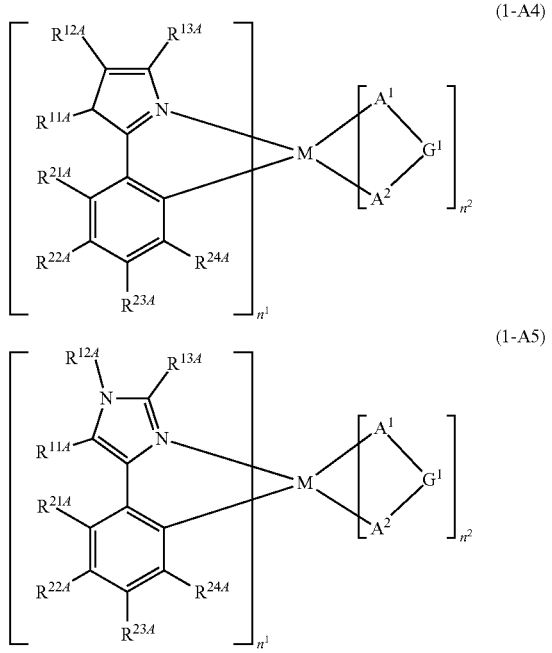

(1-A4)

(1-A5)

[wherein, M, $n^1$, $n^2$, $R^{11A}$, $R^{12A}$, $R^{13A}$, $R^{21A}$, $R^{22A}$, $R^{23A}$, $R^{24A}$ and $A^1$-$G^1$-$A^2$ represent the same meaning as described above.].

[11] A light emitting device comprising the composition according to any one of [1] to [10].

Effect of the Invention

According to the present invention, a composition which is useful for production of a light emitting device excellent in external quantum efficiency can be provided. Further, according to the present invention, a light emitting device comprising the composition can be provided.

MODES FOR CARRYING OUT THE INVENTION

Suitable embodiments of the present invention will be illustrated in detail below.

Explanation of Common Terms

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

In the formula representing a metal complex, the solid line representing the bond to the central metal means a covalent bond or a coordinate bond.

"The polymer compound" means a polymer having molecular weight distribution and having a polystyrene-equivalent number-average molecular weight of $1 \times 10^3$ to $1 \times 10^8$.

"The low molecular compound" means a compound having no molecular weight distribution and having a molecular weight of $1 \times 10^4$ or less.

"The constitutional unit" means a unit which is present one or more times in the polymer compound.

"The alkyl group" may be any of linear or branched. The number of carbon atoms of the linear alkyl group is, not including the number of carbon atoms of the substituent, usually 1 to 50, preferably 3 to 30, more preferably 4 to 20. The number of carbon atoms of the branched alkyl group is, not including the number of carbon atoms of the substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group, and these groups in which its hydrogen atom is substituted with a cycloalkyl group, an alkoxy group, a cycloalkoxy group, an aryl group, a fluorine atom or the like (for example, a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl)propyl group and a 6-ethyloxyhexyl group).

The number of carbon atoms of the "cycloalkyl group" is, not including the number of carbon atoms of the substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"The aryl group" means an atomic group remaining after removing from an aromatic hydrocarbon one hydrogen atom directly bonding to a carbon atom constituting the ring. The number of carbon atoms of the aryl group is, not including the number of carbon atoms of the substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group and a 4-phenylphenyl group, and these groups in which its hydrogen atom is substituted with an alkyl group, a cycloalkyl group, an alkoxy group, a cycloalkoxy group, an aryl group, a fluorine atom or the like.

"The alkoxy group" may be any of linear or branched. The number of carbon atoms of the linear alkoxy group is, not including the number of carbon atoms of the substituent, usually 1 to 40, preferably 4 to 10. The number of carbon atoms of the branched alkoxy group is, not including the number of carbon atoms of the substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauryloxy group, and these groups in which its hydrogen atom is substituted with a cycloalkyl group, an alkoxy group, a cycloalkoxy group, an aryl group, a fluorine atom or the like.

The number of carbon atoms of the "cycloalkoxy group" is, not including the number of carbon atoms of the substituent, usually 3 to 40, preferably 4 to 10.

The cycloalkoxy group optionally has a substituent, and examples thereof include a cyclohexyloxy group.

The number of carbon atoms of the "aryloxy group" is, not including the number of carbon atoms of the substituent, usually 6 to 60, preferably 6 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group and a 1-pyrenyloxy group, and these groups in which its hydrogen atom is substituted with an alkyl group, a cycloalkyl group, an alkoxy group, a cycloalkoxy group, a fluorine atom or the like.

"The p-valent heterocyclic group" (p represents an integer of 1 or more.) means an atomic group remaining after removing from a heterocyclic compound p hydrogen atoms among hydrogen atoms directly bonding to carbon atoms or hetero atoms constituting the ring. Of the p-valent heterocyclic groups, preferable are "p-valent aromatic heterocyclic groups" which are atomic groups remaining after removing from an aromatic heterocyclic compound p hydrogen atoms among hydrogen atoms directly bonding to carbon atoms or hetero atoms constituting the ring.

"The aromatic heterocyclic compound" means a compound in which the hetero ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzophosphole and the like and a compound in which an aromatic ring is condensed to the hetero ring even if the hetero ring itself shows no aromaticity such as phenoxazine, phenothiazine, dibenzoborole, dibenzosilole, benzopyran and the like.

The number of carbon atoms of the monovalent heterocyclic group is, not including the number of carbon atoms of the substituent, usually 2 to 60, preferably 4 to 20.

The monovalent heterocyclic group optionally has a substituent, and examples thereof include a thienyl group, a pyrrolyl group, a furyl group, a pyridyl group, a piperidinyl group, a quinolinyl group, an isoquinolinyl group, a pyrimidinyl group and a triazinyl group, and these groups in which its hydrogen atom is substituted with an alkyl group, a cycloalkyl group, an alkoxy group, a cycloalkoxy group or the like.

"The halogen atom" denotes a fluorine atom, a chlorine atom, a bromine atom or an iodine atom.

"The amino group" optionally has a substituent, and a substituted amino group is preferable. The substituent which the amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl)amino group and a bis(3,5-di-tert-butylphenyl)amino group.

"The alkenyl group" may be any of linear or branched. The number of carbon atoms of the linear alkenyl group is, not including the number of carbon atoms of the substituent, usually 2 to 30, preferably 3 to 20. The number of carbon atoms of the branched alkenyl group is, not including the number of carbon atoms of the substituent, usually 3 to 30, preferably 4 to 20.

The number of carbon atoms of "the cycloalkenyl group" is, not including the number of carbon atoms of the substituent, usually 3 to 30, preferably 4 to 20.

The alkenyl group and the cycloalkenyl group optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group and a 7-octenyl group, and these groups having a substituent.

"The alkynyl group" may be any of linear or branched. The number of carbon atoms of the alkynyl group is, not including the number of carbon atoms of the substituent, usually 2 to 20, preferably 3 to 20. The number of carbon atoms of the branched alkynyl group is, not including the number of carbon atoms of the substituent, usually 4 to 30, preferably 4 to 20.

The number of carbon atoms of "the cycloalkynyl group" is, not including the number of carbon atoms of the substituent, usually 4 to 30, preferably 4 to 20.

The alkynyl group and the cycloalkynyl group optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group and a 5-hexynyl group, and these groups having a substituent.

"The arylene group" means an atomic group remaining after removing from an aromatic hydrocarbon two hydrogen atoms directly bonding to carbon atoms constituting the ring. The number of carbon atoms of the arylene group is, not including the number of carbon atoms of the substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group and a chrysenediyl group, and these groups having a substituent, and preferable are groups represented by the formula (A-1) to the formula (A-20). The arylene group includes groups in which a plurality of these groups are connected.
[Chemical Formula 13]
(A-1)
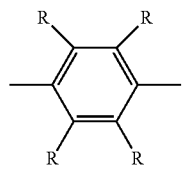
(A-2)
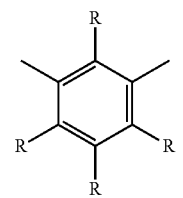
(A-3)
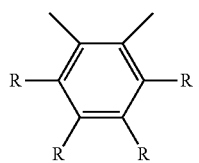
(A-4)
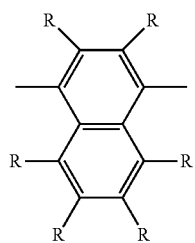
(A-5)
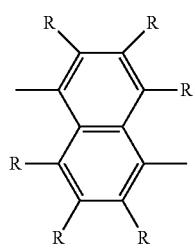
(A-6)
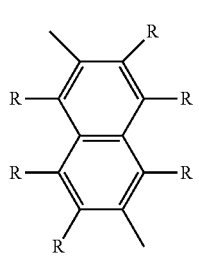
[Chemical Formula 14]
(A-7)
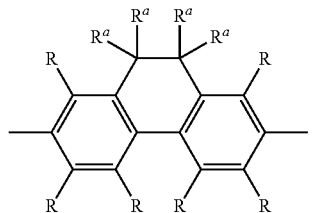
(A-8)
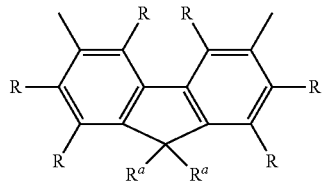
(A-9)
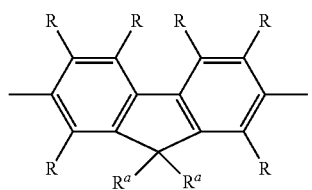
(A-10)
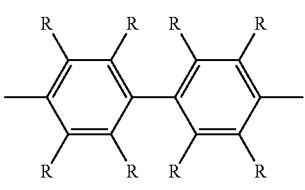
[Chemical Formula 15]
(A-11)
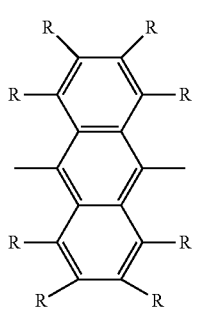
(A-12)
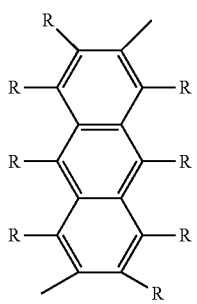

(A-13)
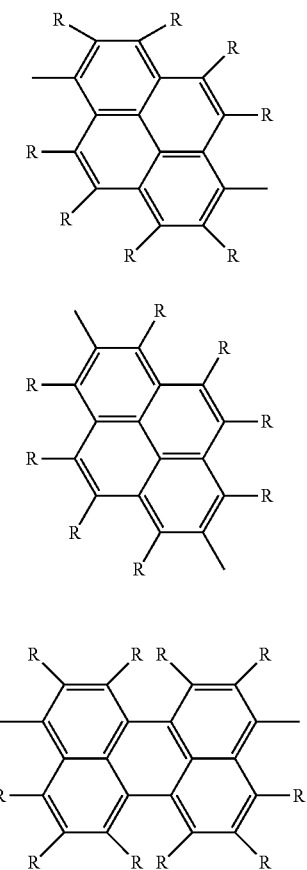

(A-14)

(A-15)

[Chemical Formula 16]

(A-16)

(A-17)
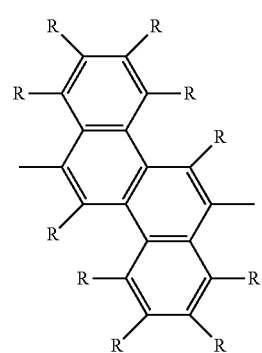

(A-18)
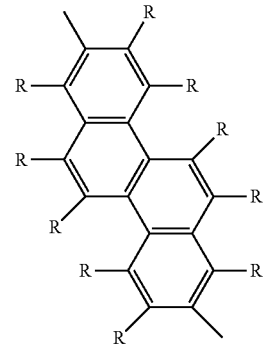

(A-19)
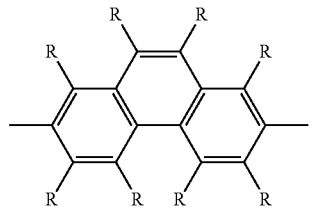

(A-20)
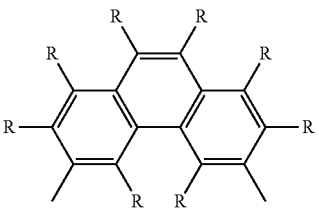

[wherein, R and $R^3$ each independently represent a hydrogen atom, an alkyl group, a cycloalkyl group, an aryl group or a monovalent heterocyclic group. A plurality of R and $R^a$ each may be the same or different, and the plurality of $R^a$ may be combined together to form a ring together with the atoms to which they are attached.]

The number of carbon atoms of the divalent heterocyclic group is, not including the number of carbon atoms of the substituent, usually 2 to 60, preferably 3 to 20, more preferably 4 to 15. The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole or triazole two hydrogen atoms among hydrogen atoms directly bonding to carbon atoms or hetero atoms constituting the ring, and preferable are groups represented by the formula (AA-1) to the formula (AA-34). The divalent heterocyclic group includes groups in which a plurality of these groups are connected.

[Chemical Formula 17]

(AA-1)
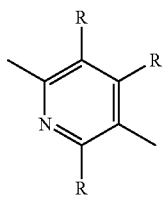

-continued
(AA-2) 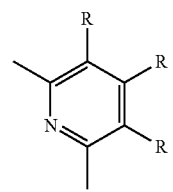
(AA-3) 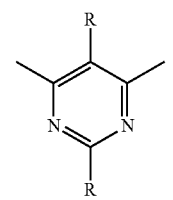
(AA-4) 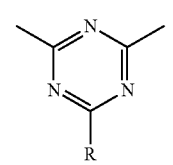
(AA-5) 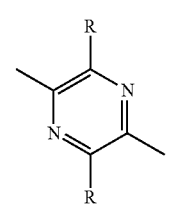
(AA-6) 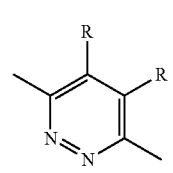
(AA-7) 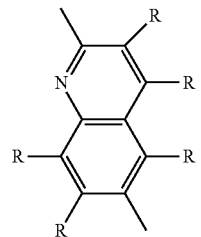
[Chemical Formula 18]
(AA-8) 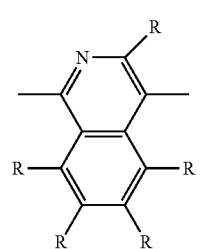
-continued
(AA-9) 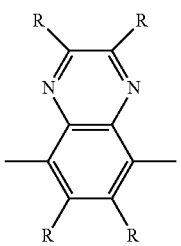
(AA-10) 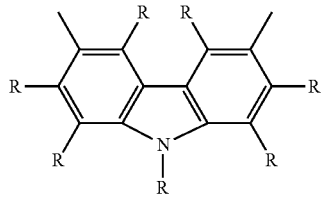
(AA-11) 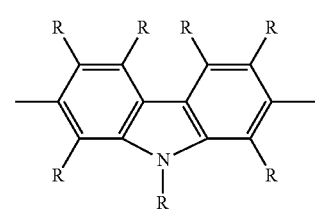
(AA-12) 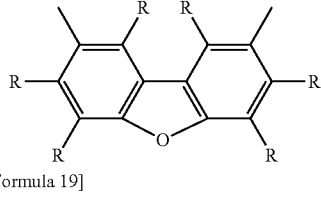
[Chemical Formula 19]
(AA-13) 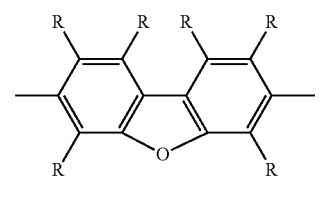
(AA-14) 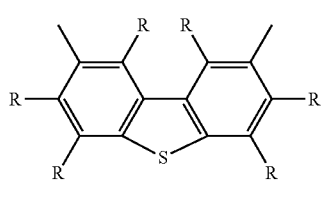
(AA-15) 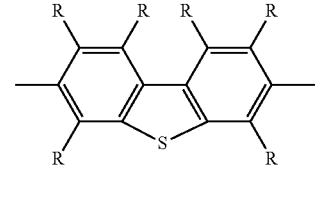
(AA-16) 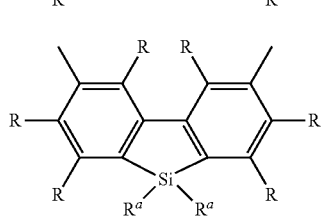

[Chemical Formula 20]
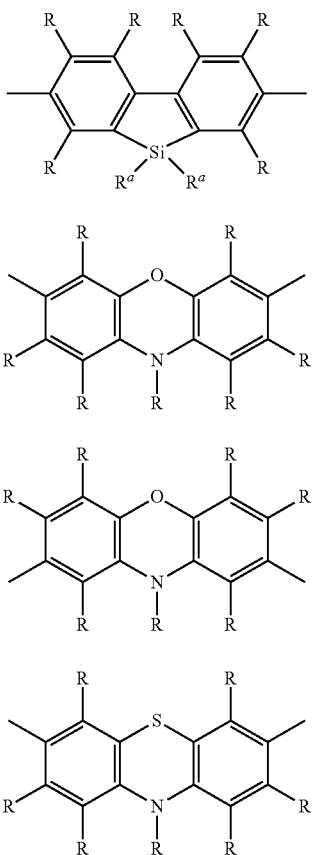
(AA-17)
(AA-18)
(AA-19)
(AA-20)
[Chemical Formula 21]
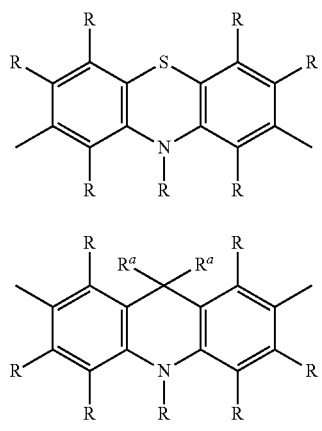
(AA-21)
(AA-22)
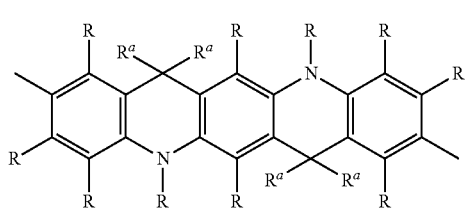
(AA-23)
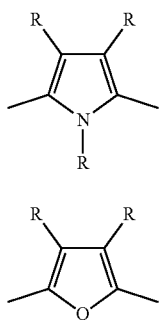
(AA-24)
(AA-25)
[Chemical Formula 22]
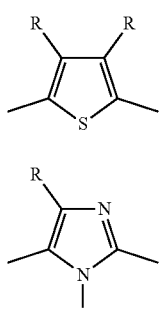
(AA-26)
(AA-27)
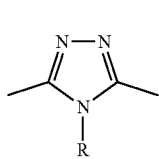
(AA-28)
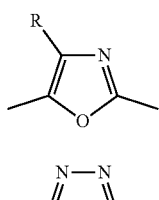
(AA-29)
(AA-30)
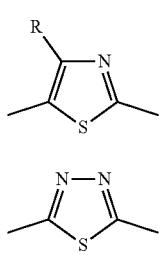
(AA-31)
(AA-32)
[Chemical Formula 23]
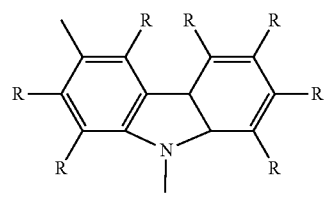
(AA-33)

-continued

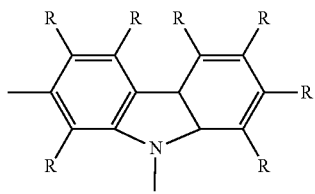
(AA-34)

[wherein, R and $R^a$ represent the same meaning as described above.]

"The crosslinkable group" is a group capable of generating a new bond by being subjected to heating, ultraviolet irradiation, near ultraviolet irradiation, visible light irradiation, infrared irradiation, radical reaction and the like, and preferably is a crosslinkable group represented by the formula (XL-1) to the formula (XL-17) in Group A of crosslinkable group.

(Group A of Crosslinkable Group)

[Chemical Formula 24]

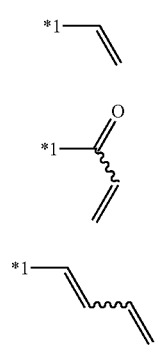
(XL-1)

(XL-2)

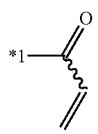
(XL-3)

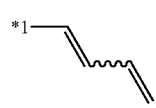
(XL-4)

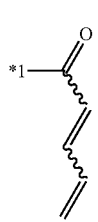
(XL-5)

(XL-6)

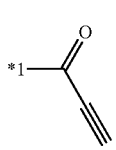
(XL-7)

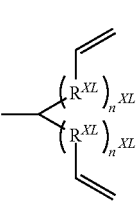

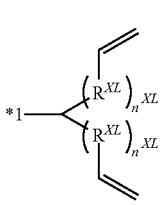

-continued

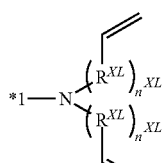
(XL-8)

(XL-9)

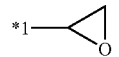
(XL-10)

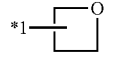
(XL-11)

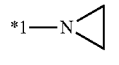
(XL-12)

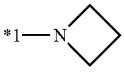
(XL-13)

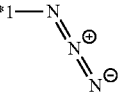
(XL-14)

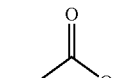
(XL-15)

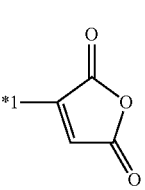
(XL-16)

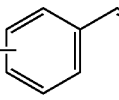
(XL-17)

[wherein, $R^{XL}$ represents a methylene group, an oxygen atom or a sulfur atom, and $n^{XL}$ represents an integer of 0 to 5. When a plurality of $R^{XL}$ are present, they may be the same or different, and when a plurality of $n^{XL}$ are present, they may be the same or different. *1 represents a binding position. These crosslinkable groups optionally have a substituent.]

"The substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Composition>

The composition of the present invention is a composition comprising two or more compounds represented by the formula (C-1) and a phosphorescent compound, wherein at least one of the above-described two or more compounds represented by the formula (C-1) is a compound represented by the formula (C-1) in which $R^C$ is a group represented by the formula (C'-1).

In the composition of the present invention, the phosphorescent compounds may be used only singly or in combination of two or more.

Compound Represented by the Formula (C-1)

The molecular weight of the compound represented by the formula (C-1) is preferably $2\times10^2$ to $5\times10^4$, more preferably $2\times10^2$ to $5\times10^3$, further preferably $3\times10^2$ to $3\times10^3$, particularly preferably $4\times10^2$ to $1\times10^3$.

The number of carbon atoms of the aromatic hydrocarbon ring represented by Ring $R^{1C}$ and Ring $R^{2C}$ is, not including the number of carbon atoms of the substituent, usually 6 to 60, preferably 6 to 30, more preferably 6 to 18.

The aromatic hydrocarbon ring represented by Ring $R^{1C}$ and Ring $R^{2C}$ includes, for example, a benzene ring, a naphthalene ring, an anthracene ring, an indene ring, a fluorene ring, a spirobifluorene ring, a phenanthrene ring, a dihydrophenanthrene ring, a pyrene ring, a chrysene ring and a triphenylene ring, and is preferably a benzene ring, a naphthalene ring, an anthracene ring, a fluorene ring, a spirobifluorene ring, a phenanthrene ring or a dihydrophenanthrene ring, more preferably a benzene ring, a naphthalene ring, a fluorene ring or a spirobifluorene ring, further preferably a benzene ring, and the foregoing rings optionally have a substituent.

The number of carbon atoms of the aromatic hetero ring represented by Ring $R^{1C}$ and Ring $R^{2C}$ is, not including the number of carbon atoms of the substituent, usually 2 to 60, preferably 3 to 30, more preferably 4 to 15.

The aromatic hetero ring represented by Ring $R^{1C}$ and Ring $R^{2C}$ includes, for example, a pyrrole ring, a diazole ring, a triazole ring, a furan ring, a thiophene ring, an oxadiazole ring, a thiadiazole ring, a pyridine ring, a diazabenzene ring, a triazine ring, an azanaphthalene ring, a diazanaphthalene ring, a triazanaphthalene ring, an azaanthracene ring, a diazaanthracene ring, a triazaanthracene ring, an azaphenanthrene ring, a diazaphenanthrene ring, a triazaphenanthrene ring, a dibenzofuran ring, a dibenzothiophene ring, a dibenzosilole ring, a dibenzophosphole ring, a carbazole ring, an azacarbazole ring, a diazacarbazole ring, a phenoxazine ring, a phenothiazine ring, a dihydroacridine ring and a dihydrophenazine ring, and is preferably a pyridine ring, a diazabenzene ring, an azanaphthalene ring, a diazanaphthalene ring, an azaanthracene ring, a diazaphenanthrene ring, a dibenzofuran ring, a dibenzothiophene ring, a carbazole ring, a phenoxazine ring, a phenothiazine ring, a dihydroacridine ring or a dihydrophenazine ring, more preferably a pyridine ring, a diazabenzene ring, an azanaphthalene ring, a diazanaphthalene ring, a dibenzofuran ring, a dibenzothiophene ring or a carbazole ring, further preferably a pyridine ring or a diazabenzene ring, and the foregoing rings optionally have a substituent.

It is preferable that at least one of Ring $R^{1C}$ and Ring $R^{2C}$ is an aromatic hydrocarbon ring, it is more preferable that both of them are each an aromatic hydrocarbon ring, it is further preferable that both of them are each a benzene ring, since a light emitting device comprising the composition of the present invention (hereinafter, referred to as "light emitting device of the present invention") is more excellent in external quantum efficiency.

The substituent which Ring $R^{1C}$ and Ring $R^{2C}$ optionally have is preferably an alkyl group, a cycloalkyl group, an alkoxy group, a cycloalkoxy group, an aryl group, an aryloxy group, a monovalent heterocyclic group, a substituted amino group or a halogen atom, more preferably an alkyl group, a cycloalkyl group, an aryl group, a monovalent heterocyclic group or a substituted amino group, further preferably an aryl group, a monovalent heterocyclic group or a substituted amino group, particularly preferably an aryl group or a monovalent heterocyclic group, and the foregoing groups optionally further have a substituent.

The number of carbon atoms of the aryl group as the substituent which Ring $R^{1C}$ and Ring $R^{2C}$ optionally have is, not including the number of carbon atoms of the substituent, usually 6 to 60, preferably 6 to 40, more preferably 6 to 25.

The aryl group as the substituent which Ring $R^{1C}$ and Ring $R^{2C}$ optionally have includes, for example, groups obtained by removing from a benzene ring, a naphthalene ring, an anthracene ring, an indene ring, a fluorene ring, a spirobifluorene ring, a phenanthrene ring, a dihydrophenanthrene ring, a pyrene ring, a chrysene ring, a triphenylene ring or a ring obtained by condensing these rings one hydrogen atom directly bonding to a carbon atom constituting the ring, and is preferably a group obtained by removing from a benzene ring, a naphthalene ring, a fluorene ring, a spirobifluorene ring, a phenanthrene ring, a dihydrophenanthrene ring or a triphenylene ring one hydrogen atom directly bonding to a carbon atom constituting the ring, more preferably a group obtained by removing from a benzene ring, a fluorene ring or a spirobifluorene ring one hydrogen atom directly bonding to a carbon atom constituting the ring, further preferably a group obtained by removing from a fluorene ring or a spirobifluorene ring one hydrogen atom directly bonding to a carbon atom constituting the ring, and the foregoing groups optionally further have a substituent.

The number of carbon atoms of the monovalent heterocyclic group as the substituent which Ring $R^{1C}$ and Ring $R^{2C}$ optionally have is, not including the number of carbon atoms of the substituent, usually 2 to 60, preferably 3 to 30, more preferably 3 to 15.

The monovalent heterocyclic group as the substituent which Ring $R^{1C}$ and Ring $R^{2C}$ optionally have includes, for example, groups obtained by removing from a pyrrole ring, a diazole ring, a triazole ring, a furan ring, a thiophene ring, an oxadiazole ring, a thiadiazole ring, a pyridine ring, a diazabenzene ring, a triazine ring, an azanaphthalene ring, a diazanaphthalene ring, a triazanaphthalene ring, an azaanthracene ring, a diazaanthracene ring, a triazaanthracene ring, an azaphenanthrene ring, a diazaphenanthrene ring, a triazaphenanthrene ring, a dibenzofuran ring, a dibenzothiophene ring, a dibenzosilole ring, a dibenzophosphole ring, a carbazole ring, an azacarbazole ring, a diazacarbazole ring, a phenoxazine ring, a phenothiazine ring, a dihydroacridine ring, a dihydrophenazine ring or a ring obtained by condensing an aromatic ring to these rings one hydrogen atom directly bonding to a carbon atom or a hetero atom constituting the ring, and is preferably a group obtained by removing from a pyridine ring, a diazabenzene ring, a triazine ring, an azanaphthalene ring, a diazanaphthalene ring, a dibenzofuran ring, a dibenzothiophene ring, a carbazole ring, an azacarbazole ring, a diazacarbazole ring, a phenoxazine ring, a phenothiazine ring, a dihydroacridine ring or a dihydrophenazine ring one hydrogen atom directly bonding to a carbon atom or a hetero atom constituting the ring, more preferably a group obtained by removing from a pyridine ring, a diazabenzene ring, a triazine ring, a dibenzofuran ring, a dibenzothiophene ring, a carbazole ring, an azacarbazole ring, a diazacarbazole ring, a phenoxazine ring, a phenothiazine ring, a dihydroacridine ring or a dihydrophenazine ring one hydrogen atom directly bonding to a carbon atom or a hetero atom constituting the ring, further preferably a group obtained by removing from a pyridine ring, a diazabenzene ring, a triazine ring, a dibenzofuran ring, a dibenzothiophene ring, a carbazole ring, a phenoxazine ring, a phenothiazine ring, a dihydroacridine ring or a dihydrophenazine ring one hydrogen atom directly bonding to a carbon atom or a hetero atom constituting the ring, particularly preferably a group obtained by removing from a triazine ring, a dibenzofuran ring, a dibenzothiophene ring or a carbazole ring one hydrogen atom directly bonding to a carbon atom or a hetero atom constituting the ring, and the foregoing rings optionally have a substituent.

In the substituted amino group as the substituent which Ring $R^{1C}$ and Ring $R^{2C}$ optionally have, the substituent which the amino group has is preferably an aryl group or a monovalent heterocyclic group, more preferably an aryl group, and the foregoing groups optionally further have a substituent. The examples and preferable ranges of the aryl group as the substituent which the amino group has are the same as the examples and preferable ranges of the aryl group as the substituent which Ring $R^{1C}$ and Ring $R^{2C}$ optionally have. The examples and preferable ranges of the monovalent heterocyclic group as the substituent which the amino group has are the same as the examples and preferable ranges of the monovalent heterocyclic group as the substituent which Ring $R^{1C}$ and Ring $R^{2C}$ optionally have.

The substituent which the substituent which Ring $R^{1C}$ and Ring $R^{2C}$ optionally have optionally further has is preferably an alkyl group, a cycloalkyl group, an alkoxy group, a cycloalkoxy group, an aryl group, an aryloxy group, a monovalent heterocyclic group, a substituted amino group or a halogen atom, more preferably an alkyl group, a cycloalkyl group, an aryl group or a monovalent heterocyclic group, further preferably an alkyl group or an aryl group, and the foregoing groups optionally further have a substituent, but it is preferable that these groups do not further have a substituent.

The examples and preferable ranges of the aryl group, the monovalent heterocyclic group and the substituted amino group as the substituent which the substituent which Ring $R^{1C}$ and Ring $R^{2C}$ optionally have optionally further has are the same as the examples and preferable ranges of the aryl group, the monovalent heterocyclic group and the substituted amino group as the substituent which Ring $R^{1C}$ and Ring $R^{2C}$ optionally have, respectively.

The aryl group, the monovalent heterocyclic group and the substituted amino group as the substituent which Ring $R^{1C}$ and Ring $R^{2C}$ optionally have are each preferably a group represented by the formula (D-1), the formula (E-1), the formula (D-A), the formula (D-B) or the formula (D-C) described later, more preferably a group represented by the formula (D-1), the formula (E-1) or the formula (D-A), further preferably a group represented by the formula (D-1) or the formula (E-1).

In the group represented by the formula (D-A) and the formula (D-B) as the substituent which Ring $R^{1C}$ and Ring $R^{2C}$ optionally have, $G^{DA}$ is preferably a group represented by the formula (GDA-11) to the formula (GDA-15) described later, more preferably a group represented by the formula (GDA-11) to the formula (GDA-14), further preferably a group represented by the formula (GDA-12) to the formula (GDA-14), particularly preferably a group represented by the formula (GDA-14).

The group represented by the formula (D-A) as the substituent which Ring $R^{1C}$ and Ring $R^{2C}$ optionally have is preferably a group represented by the formula (D-A1) to the formula (D-A5) described later, more preferably a group represented by the formula (D-A1) to the formula (D-A3), further preferably a group represented by the formula (D-A3).

The group represented by the formula (D-B) as the substituent which Ring $R^{1C}$ and Ring $R^{2C}$ optionally have is preferably a group represented by the formula (D-B1) to the formula (D-B6) described later, more preferably a group represented by the formula (D-B1), the formula (D-B4) or the formula (D-B5), further preferably a group represented by the formula (D-B5).

The group represented by the formula (D-C) as the substituent which Ring $R^{1C}$ and Ring $R^{2C}$ optionally have is preferably a group represented by the formula (D-C1) to the formula (D-C4) described later, more preferably a group represented by the formula (D-C1).

$R^C$ is preferably a sulfur atom or a group represented by the formula (C'-1), since the light emitting device of the present invention is more excellent in external quantum efficiency.

Group Represented by the Formula (C'-1)

$R^{C'}$ is preferably a carbon atom, a silicon atom or a germanium atom, more preferably a carbon atom or a silicon atom, further preferably a carbon atom, since the light emitting device of the present invention is more excellent in external quantum efficiency.

It is preferable that at least one of Ring $R^{3C}$ and Ring $R^{4C}$ is an aromatic hydrocarbon ring, it is more preferable that both of them are each an aromatic hydrocarbon ring, it is further preferable that both of them are each a benzene ring, since the light emitting device of the present invention is more excellent in external quantum efficiency.

The examples and preferable ranges of the aromatic hydrocarbon ring and the aromatic hetero ring represented by Ring $R^{3C}$ and Ring $R^{4C}$ are the same as the examples and preferable ranges of the aromatic hydrocarbon ring and the aromatic hetero ring represented by Ring $R^{1C}$ and Ring $R^{2C}$, respectively. The examples and preferable ranges of the substituent which Ring $R^{3C}$ and Ring $R^{4C}$ optionally have are the same as the examples and preferable ranges of the substituent which Ring $R^{1C}$ and Ring $R^{2C}$ optionally have.

The examples and preferable ranges of the substituent which the substituent which Ring $R^{3C}$ and Ring $R^{4C}$ optionally have optionally further has are the same as the examples and preferable ranges of the substituent which the substituent which Ring $R^{1C}$ and Ring $R^{2C}$ optionally have optionally further has.

When $R^C$ is a group represented by the formula (C'-1), at least one of Ring $R^{1C}$, Ring $R^{2C}$, Ring $R^{3C}$ and Ring $R^{4C}$ preferably has an aryl group, a monovalent heterocyclic group or a substituted amino group, more preferably has a group represented by the formula (D-1), the formula (E-1), the formula (D-A), the formula (D-B) or the formula (D-C) described later, further preferably has a group represented by the formula (D-1), the formula (E-1) or the formula (D-A), particularly preferably has a group represented by the formula (D-1) or the formula (E-1), since the light emitting device of the present invention is more excellent in external quantum efficiency.

When $R^C$ is a group represented by the formula (C'-1) and at least one of Ring $R^{1C}$, Ring $R^{2C}$, Ring $R^{3C}$ and Ring $R^{4C}$ is an aryl group, a monovalent heterocyclic group or a substituted amino group, the total number of the aryl group, the monovalent heterocyclic group and the substituted amino group which Ring $R^{1C}$ and Ring $R^{2C}$ have is preferably 1 to 5, more preferably 1 to 3, further preferably 1 or 2, particularly preferably 1.

When $R^C$ is a group represented by the formula (C'-1), when at least one of Ring $R^{1C}$, Ring $R^{2C}$, Ring $R^{3C}$ and Ring $R^{4C}$ has a group represented by the formula (D-1), the formula (E-1), the formula (D-A), the formula (D-B) or the formula (D-C) described later, the total number of the group represented by the formula (D-1), the formula (E-1), the formula (D-A), the formula (D-B) and the formula (D-C) which Ring $R^{1C}$ and Ring $R^{2C}$ have is preferably 1 to 5, more preferably 1 to 3, further preferably 1 or 2, particularly preferably 1.

When $R^C$ is an oxygen atom or a sulfur atom, at least one of Ring $R^{1C}$ and Ring $R^{2C}$ preferably has an aryl group or a monovalent heterocyclic group, more preferably has a group represented by the formula (D-1) or the formula (E-1) described later, further preferably has a group represented by the formula (E-1), since the light emitting device of the present invention is more excellent in external quantum efficiency.

When $R^C$ is an oxygen atom or a sulfur atom, when at least one of Ring $R^{1C}$ and Ring $R^{2C}$ has an aryl group or a monovalent heterocyclic group, the total number of the aryl group and the monovalent heterocyclic group which Ring $R^{1C}$ and Ring $R^{2C}$ have is preferably 1 to 5, more preferably 1 to 3, further preferably 1 or 2, particularly preferably 1.

When $R^C$ is an oxygen atom or a sulfur atom, when at least one of Ring $R^{1C}$ and Ring $R^{2C}$ has a group represented by the formula (D-1) or the formula (E-1) described later, the total number of the group represented by the formula (D-1) and the formula (E-1) which Ring $R^{1C}$ and Ring $R^{2C}$ have is preferably 1 to 5, more preferably 1 to 3, further preferably 1 or 2, particularly preferably 1.

Group Represented by the Formula (D-1)

[Chemical Formula 25]

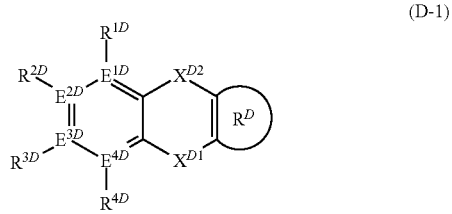

(D-1)

[wherein,

Ring $R^D$ represents an aromatic hydrocarbon ring or an aromatic hetero ring, and the foregoing rings optionally have a substituent. When a plurality of the substituents are present, they may be combined together to form a ring together with the atoms to which they are attached.

$X^{D1}$ and $X^{D2}$ each independently represent a single bond, an oxygen atom, a sulfur atom, a group represented by $-N(R^{XD1})-$ or a group represented by $-C(R^{XD2})_2-$. $R^{XD1}$ and $R^{XD2}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. A plurality of $R^{XD2}$ may be the same or different and may be combined together to form a ring together with the carbon atoms to which they are attached.

$E^{1D}$, $E^{2D}$, $E^{3D}$ and $E^{4D}$ each independently represent a nitrogen atom or a carbon atom. At least one of $E^{1D}$, $E^{2D}$, $E^{3D}$ and $E^{4D}$ is a carbon atom.

$R^{1D}$, $R^{2D}$, $R^{3D}$ and $R^{4D}$ each independently represent, a connecting bond, a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. One of $R^{1D}$, $R^{2D}$, $R^{3D}$ and $R^{4D}$ is a connecting bond.

When $E^{1D}$ is a nitrogen atom, $R^{1D}$ is absent. When $E^2$ is a nitrogen atom, $R^{2D}$ is absent. When $E^{3D}$ is a nitrogen atom, $R^{3D}$ is absent. When $E^{41}$ is a nitrogen atom, $R^{4D}$ is absent.

When $R^{1D}$ is a connecting bond, $E^{1D}$ is a carbon atom. When $R^{2D}$ is a connecting bond, $E^{2D}$ is a carbon atom. When $R^{3D}$ is a connecting bond, $E^{3D}$ is a carbon atom. When $R^{4D}$ is a connecting bond, $E^{4D}$ is a carbon atom.

$R^{1D}$ and $R^{2D}$ may be combined together to form a ring together with the atoms to which they are attached. $R^{2D}$ and $R^{3D}$ may be combined together to form a ring together with the atoms to which they are attached. $R^{3D}$ and $R^{4D}$ may be combined together to form a ring together with the atoms to which they are attached. $R^{1D}$ and $R^{XD1}$ may be combined together to form a ring together with the atoms to which they are attached. $R^{1D}$ and $R^{XD2}$ may be combined together to form a ring together with the atoms to which they are attached. $R^{4D}$ and $R^{XD1}$ may be combined together to form a ring together with the atoms to which they are attached. $R^{4D}$ and $R^{XD2}$ may be combined together to form a ring together with the atoms to which they are attached. The substituent which Ring $R^D$ optionally has and $R^{XD1}$ may be combined together to form a ring together with the atoms to which they are attached. The substituent which Ring $R^D$ optionally has and $R^{XD2}$ may be combined together to form a ring together with the carbon atoms to which they are attached.]

The examples and preferable ranges of the aromatic hydrocarbon ring and the aromatic hetero ring represented by Ring $R^D$ are the same as the examples and preferable ranges of the aromatic hydrocarbon ring and the aromatic hetero ring represented by Ring $R^{1C}$ and Ring $R^{2C}$, respectively.

The examples and preferable ranges of the substituent which Ring $R^D$ optionally has are the same as the examples and preferable ranges of the substituent which the substituent which Ring $R^{1C}$ and Ring $R^{2C}$ optionally have optionally further has.

Ring $R^D$ is preferably an aromatic hydrocarbon ring, more preferably a benzene ring, since the light emitting device of the present invention is more excellent in external quantum efficiency.

$X^{D1}$ and $X^{D2}$ are each preferably a single bond, an oxygen atom, a sulfur atom or a group represented by $-C(R^{XD2})_2-$, more preferably a single bond, a sulfur atom or $-C(R^{XD2})_2-$, further preferably a single bond or a sulfur atom, since the light emitting device of the present invention is more excellent in external quantum efficiency.

It is preferable that at least one of $X^{D1}$ and $X^{D2}$ is a single bond, it is more preferable that $X^{D2}$ is a single bond.

$R^{XD1}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

$R^{XD2}$ is preferably an alkyl group, a cycloalkyl group, an aryl group or a monovalent heterocyclic group, more preferably an alkyl group or an aryl group, further preferably an aryl group, and the foregoing groups optionally have a substituent.

The examples and preferable ranges of the aryl group, the monovalent heterocyclic group and the substituted amino group represented by $R^{XD1}$ and $R^{XD2}$ are the same as the examples and preferable ranges of the aryl group, the monovalent heterocyclic group and the substituted amino group as the substituent which Ring $R^{1C}$ and Ring $R^{2C}$ optionally have, respectively.

Regarding the combination of two groups $R^{XD2}$ in the group represented by —C($R^{XD2}$)$_2$— represented by $X^{D1}$ and $X^{D2}$, it is preferable that the both are alkyl groups or cycloalkyl groups, the both are aryl groups, the both are monovalent heterocyclic groups, or one is an alkyl group or a cycloalkyl group and the other is an aryl group or a monovalent heterocyclic group, it is more preferable that the both are aryl groups, or one is an alkyl group or a cycloalkyl group and the other is an aryl group, it is further preferable that the both are aryl groups, and the foregoing groups optionally have a substituent. It is preferable that two groups $R^{XD2}$ are combined together to form a ring together with the carbon atoms to which they are attached. When $R^{XD2}$ forms a ring, the group represented by —C($R^{XD2}$)$_2$— is preferably a group represented by the formula (Y-A1) to the formula (Y-A5), more preferably a group represented by the formula (Y-A$^4$), and the foregoing groups optionally have a substituent.

[Chemical Formula 26]

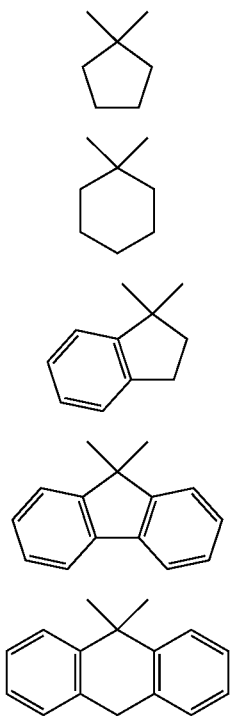

(Y-A1)

(Y-A2)

(Y-A3)

(Y-A4)

(Y-A5)

The examples and preferable ranges of the substituent which $R^{XD1}$ and $R^{XD2}$ optionally have are the same as the examples and preferable ranges of the substituent which the substituent which Ring $R^{1C}$ and Ring $R^{2C}$ optionally have optionally further has.

$E^{1D}$, $E^{2D}$, $E^3$ and $E^{4D}$ are each preferably a carbon atom.

It is preferable that $R^{1D}$, $R^{3D}$ or $R^{4D}$ is a connecting bond, it is more preferable that $R^{1D}$ or $R^{4D}$ is a connecting bond, it is further preferable that $R^{4D}$ is a connecting bond.

In the case where $R^{1D}$, $R^{2D}$, $R^{3D}$ and $R^{4D}$ are other than a connecting bond, $R^{1D}$, $R^{2D}$, $R^{3D}$ and $R^{4D}$ are each preferably a hydrogen atom, an alkyl group, a cycloalkyl group, an aryl group, a monovalent heterocyclic group or a substituted amino group, more preferably a hydrogen atom, an alkyl group or an aryl group, further preferably a hydrogen atom, and the foregoing groups optionally further have a substituent.

The examples and preferable ranges of the aryl group, the monovalent heterocyclic group and the substituted amino group represented by $R^{1D}$, $R^{2D}$, $R^{3D}$ and $R^{4D}$ are the same as the examples and preferable ranges of the aryl group, the monovalent heterocyclic group and the substituted amino group as the substituent which Ring $R^{1C}$ and Ring $R^{2C}$ optionally have, respectively.

The examples and preferable ranges of the substituent which $R^{1D}$, $R^{2D}$, $R^{3D}$ and $R^{4D}$ optionally have are the same as the examples and preferable ranges of the substituent which $R^{XD1}$ and $R^{XD2}$ optionally have.

$R^{1D}$ and $R^{2D}$, $R^{2D}$ and $R^{3D}$, $R^{3D}$ and $R^{4D}$, $R^{1D}$ and $R^{XD1}$, $R^{1D}$ and $R^{XD1}$, $R^{1D}$ and $R^{XD2}$, $R^{4D}$ and $R^{XD1}$, $R^{4D}$ and $R^{XD2}$, $R^{XD1}$ and the substituent which Ring $R^D$ optionally has, and, $R^{XD2}$ and the substituent which Ring $R^D$ optionally has may each be combined together to form a ring together with the carbon atoms to which they are attached, but it is preferable that they do not form a ring.

The group represented by the formula (D-1) is preferably a group represented by the formula (D-2), since the light emitting device of the present invention is more excellent in external quantum efficiency.

Group Represented by the Formula (D-2)

[Chemical Formula 27]

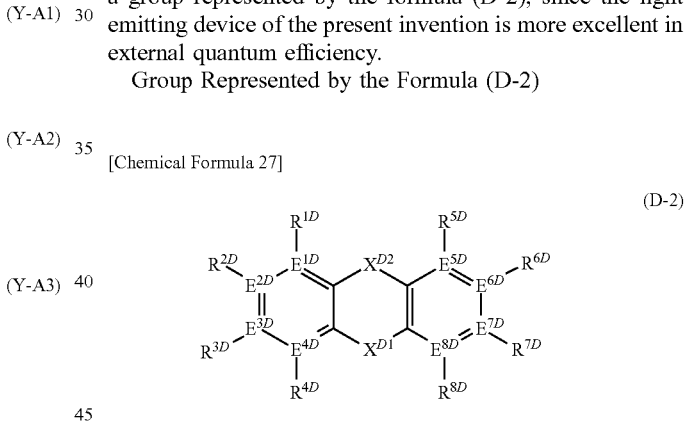

(D-2)

[wherein, $X^{D1}$, $X^{D2}$, $E^{1D}$, $E^{2D}$, $E^{3D}$, $E^{4D}$, $R^{1D}$, $R^{2D}$, $R^{3D}$ and $R^{4D}$ represent the same meaning as described above.

$E^{5D}$, $E^{6D}$, $E^{7D}$ and $E^{8D}$ each independently represent a nitrogen atom or a carbon atom.

$R^{5D}$, $R^{6D}$, $R^{7D}$ and $R^{8D}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent.

When $E^{5D}$ is a nitrogen atom, $R^{5D}$ is absent. When $E^{6D}$ is a nitrogen atom, $R^{6D}$ is absent. When $E^{7D}$ is a nitrogen atom, $R^{7D}$ is absent. When $E^{8D}$ is a nitrogen atom, $R^{8D}$ is absent.

$R^{5D}$ and $R^{6D}$, $R^{6D}$ and $R^{7D}$, $R^{7D}$ and $R^{8D}$, $R^{5D}$ and $R^{XD1}$, $R^{5D}$ and $R^{XD2}$, $R^{8D}$ and $R^{XD1}$, and $R^{8D}$ and $R^{XD2}$ may each be combined together to form a ring together with the carbon atoms to which they are attached.]

$E^{5D}$, $E^{6D}$, $E^{7D}$ and $E^{8D}$ are each preferably a carbon atom.

The examples and preferable ranges of $R^{5D}$, $R^{6D}$, $R^{7D}$ and $R^{8D}$ are the same as the examples and preferable ranges of $R^{1D}$, $R^{2D}$, $R^{3D}$ and $R^{4D}$ when $R^{1D}$, $R^{2D}$, $R^{3D}$ and $R^{4D}$ are other than a connecting bond.

The examples and preferable ranges of the substituent which $R^{5D}$, $R^{6D}$, $R^{7D}$ and $R^{8D}$ optionally have are the same as the examples and preferable ranges of the substituent which $R^{1D}$, $R^{2D}$, $R^{3D}$ and $R^{4D}$ optionally have.

$R^{5D}$ and $R^{6D}$, $R^{6D}$ and $R^{7D}$, $R^{7D}$ and $R^{8D}$, $R^{5D}$ and $R^{XD1}$, $R^{5D}$ and $R^{XD2}$, $R^{8D}$ and $R^{XD1}$, and $R^{8D}$ and $R^{XD2}$ may each be combined together to form a ring together with the carbon atoms to which they are attached, but it is preferable that they do not form a ring.

Group Represented by the Formula (E-1)

[Chemical Formula 28]

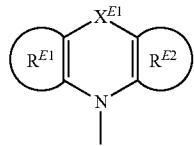

(E-1)

[wherein,

Ring $R^{E1}$ and Ring $R^{E2}$ each independently represent an aromatic hydrocarbon ring or an aromatic hetero ring, and the foregoing rings optionally have a substituent. When a plurality of the substituents are present, they may be combined together to form a ring together with the atoms to which they are attached.

$X^{E1}$ represents a single bond, an oxygen atom, a sulfur atom, a group represented by —N($R^{XE1}$)— or a group represented by —C($R^{XE2}$)$_2$—. $R^{XE1}$ and $R^{XE2}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. A plurality of $R^{XE2}$ may be the same or different and may be combined together to form a ring together with the carbon atoms to which they are attached.]

The examples and preferable ranges of the aromatic hydrocarbon ring and the aromatic hetero ring represented by Ring $R^{E1}$ and Ring $R^{E2}$ are the same as the examples and preferable ranges of the aromatic hydrocarbon ring and the aromatic hetero ring represented by Ring $R^{1C}$ and Ring $R^{2C}$, respectively.

The examples and preferable ranges of the substituent which Ring $R^{E1}$ and Ring $R^{E2}$ optionally have are the same as the examples and preferable ranges of the substituent which the substituent which Ring $R^{1C}$ and Ring $R^{2C}$ optionally have optionally further has, respectively.

It is preferable that at least one of Ring $R^{E1}$ and Ring $R^{E2}$ is an aromatic hydrocarbon ring, it is more preferable that both of them are each an aromatic hydrocarbon ring, it is further preferable that both of them are each a benzene ring, since the light emitting device of the present invention is more excellent in external quantum efficiency.

$X^{E1}$ is preferably a single bond, an oxygen atom, a sulfur atom or a group represented by —C($R^{XD2}$)$_2$—, more preferably a single bond, an oxygen atom or a sulfur atom, further preferably a single bond, since the light emitting device of the present invention is more excellent in external quantum efficiency.

The examples and preferable ranges of the group represented by $R^{XE1}$ are the same as the examples and preferable ranges of the group represented by $R^{XD1}$. The examples and preferable ranges of the group represented by $R^{XE2}$ are the same as the examples and preferable ranges of the group represented by $R^{XD2}$.

The group represented by the formula (E-1) is preferably a group represented by the formula (E-2), since the light emitting device of the present invention is more excellent in external quantum efficiency.

[Chemical Formula 29]

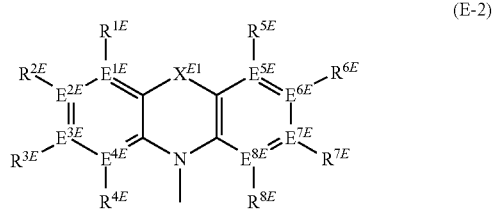

(E-2)

[wherein, $X^{E1}$ represents the same meaning as described above.

$E^{1E}$, $E^{2E}$, $E^{3E}$, $E^{4E}$, $E^{5E}$, $E^{6E}$, $E^{7E}$ and $E^{9E}$ each independently represent a nitrogen atom or a carbon atom.

$R^{1E}$, $R^{2E}$, $R^{3E}$, $R^{4E}$, $R^{5E}$, $R^{6E}$, $R^{7E}$ and $R^{8E}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent.

When $E^{1E}$ is a nitrogen atom, $R^{1E}$ is absent. When $E^{2E}$ is a nitrogen atom, $R^{2E}$ is absent. When $E^{3E}$ is a nitrogen atom, $R^{3E}$ is absent. When $E^{4E}$ is a nitrogen atom, $R^{4E}$ is absent. When $E^{5E}$ is a nitrogen atom, $R^{5E}$ is absent. When $E^{6E}$ is a nitrogen atom, $R^{6E}$ is absent. When $E^{7E}$ is a nitrogen atom, $R^{7E}$ is absent. When $E^{8E}$ is a nitrogen atom, $R^{8E}$ is absent.

$R^{1E}$ and $R^{2E}$, $R^{2E}$ and $R^{3E}$, $R^{3E}$ and $R^{4E}$, $R^{5E}$ and $R^{6E}$, $R^{6E}$ and $R^{7E}$, $R^{7E}$ and $R^{6E}$, $R^{5E}$ and $R^{XD1}$, $R^{5E}$ and $R^{XD2}$, $R^{1E}$ and $R^{XD1}$, and $R^{1E}$ and $R^{XD2}$ may each be combined together to form a ring together with the carbon atoms to which they are attached.]

$E^{1E}$, $E^{2E}$, $E^{3E}$, $E^4$, $E^{5E}$, $E^{6E}$, $E^{7E}$ and $E^{8E}$ are each preferably a carbon atom.

The examples and preferable ranges of $R^{1E}$, $R^{2E}$, $R^{3E}$, $R^{4E}$, $R^{5E}$, $R^{6E}$, $R^{7E}$ and $R^{6E}$ are the same as the examples and preferable ranges of $R^{1D}$, $R^{2D}$, $R^{3D}$ and $R^{4D}$ when $R^{1D}$, $R^{2D}$, $R^{3D}$ and $R^{4D}$ are other than a connecting bond.

The examples and preferable ranges of the substituent which $R^{1E}$, $R^{2E}$, $R^{3E}$, $R^{4E}$, $R^{5E}$, RCE, $R^{7E}$ and $R^{8E}$ optionally have are the same as the examples and preferable ranges of the substituent which $R^{1D}$, $R^{2D}$, $R^{3D}$ and $R^{4D}$ optionally have.

$R^{1E}$ and $R^{2E}$, $R^{2E}$ and $R^{3E}$, $R^{3E}$ and $R^{4E}$, $R^{5E}$ and $R^{6E}$, $R^{6E}$ and $R^{7E}$, $R^{7E}$ and $R^{5E}$, $R^{5E}$ and $R^{XD1}$, $R^{5E}$ and $R^{XD2}$, $R^{1E}$ and $R^{XD1}$, and $R^{1E}$ and $R^{XD2}$ may each be combined together to form a ring together with the carbon atoms to which they are attached, but it is preferable that they do not form a ring.

Compound Represented by the Formula (C-2-1) and Compound Represented by the Formula (C-2-2)

The compound represented by the formula (C-1) is preferably a compound represented by the formula (C-2-1) or a compound represented by the formula (C-2-2), since the light emitting device of the present invention is more excellent in external quantum efficiency.

In the compound represented by the formula (C-2-1) and the formula (C-2-2), $E^{11C}$, $E^{12C}$, $E^{13C}$, $E^{14C}$, $E^{21C}$, $E^{22C}$, $E^{23C}$, $E^{24C}$, $E^{31C}$, $E^{32C}$, $E^{33C}$, $E^{34C}$, $E^{41C}$, $E^{42C}$, $E^{43C}$ and $E^{44C}$ are each preferably a carbon atom.

In the compound represented by the formula (C-2-1) and the formula (C-2-2), Ring $R^{1C'}$, Ring $R^{2C'}$, Ring $R^{3C'}$ and Ring $R^{4C'}$ are each preferably a benzene ring.

In the compound represented by the formula (C-2-2), $R^{C''}$ is preferably a sulfur atom, since the light emitting device of the present invention is more excellent in external quantum efficiency.

In the compound represented by the formula (C-2-1), $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ are each preferably a hydrogen atom, an alkyl group, a cycloalkyl group, an aryl group, a monovalent heterocyclic group or a substituted amino group, more preferably a hydrogen atom, an aryl group, a monovalent heterocyclic group or a substituted amino group, further preferably a hydrogen atom or a group represented by the formula (D-1), the formula (E-1), the formula (D-A) described later, the formula (D-B) described later or the formula (D-C) described later, particularly preferably a hydrogen atom or a group represented by the formula (D-1), the formula (E-1) or the formula (D-A), especially preferably a hydrogen atom or a group represented by the formula (D-1) or the formula (E-1), and the foregoing groups optionally further have a substituent.

In the compound represented by the formula (C-2-1), at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is preferably an aryl group, a monovalent heterocyclic group or a substituted amino group, more preferably a group represented by the formula (D-1), the formula (E-1), the formula (D-A) described later, the formula (D-B) described later or the formula (D-C) described later, further preferably a group represented by the formula (D-1), the formula (E-1) or the formula (D-A), particularly preferably a group represented by the formula (D-1) or the formula (E-1), and the foregoing groups optionally further have a substituent.

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is an aryl group, a monovalent heterocyclic group or a substituted amino group, the total number of the aryl group, the monovalent heterocyclic group or the substituted amino group represented by $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is preferably 1 to 5, more preferably 1 to 3, further preferably 1 or 2, particularly preferably 1.

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is a group represented by the formula (D-1), the formula (E-1), the formula (D-A) described later, the formula (D-B) described later or the formula (D-C) described later, the total number of the group represented by the formula (D-1), the formula (E-1), the formula (D-A), the formula (D-B) or the formula (D-C) represented by $R^{11C}$, $R^{12C}$, $R^{13C}$, $R^{14C}$, $R^{21C}$, $R^{22C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is preferably 1 to 5, more preferably 1 to 3, further preferably 1 or 2, particularly preferably 1.

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is an aryl group, a monovalent heterocyclic group or a substituted amino group, it is preferable that at least one of $R^{11C}$, $R^{12C}$, $R^{13C}$, $R^{21C}$, $R^{22C}$, $R^{23C}$, $R^{31C}$, $R^{32C}$, $R^{33C}$, $R^{41C}$, $R^{42C}$ and $R^{43C}$ is an aryl group, a monovalent heterocyclic group or a substituted amino group, it is more preferable that at least one of $R^{11C}$, $R^{12C}$, $R^{13C}$, $R^{21C}$, $R^{22C}$ and $R^{23C}$ is an aryl group, a monovalent heterocyclic group or a substituted amino group, and the foregoing groups optionally have a substituent.

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is a group represented by the formula (D-1), it is preferable that at least one of $R^{11C}$, $R^{12C}$, $R^{13C}$, $R^{21C}$, $R^{22C}$, $R^{23C}$, $R^{31C}$, $R^{32C}$, $R^{33C}$, $R^{41C}$, $R^{42C}$ and $R^{43C}$ is a group represented by the formula (D-1), it is more preferable that at least one of $R^{11C}$, $R^{12C}$, $R^{13C}$, $R^{21C}$, $R^{22C}$ and $R^{23C}$ is a group represented by the formula (D-1), it is further preferable that at least one of $R^{11C}$, $R^{12C}$, $R^{21C}$ and $R^{22C}$ is a group represented by the formula (D-1).

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C\,C}$, $R^{31C}$, $R^{32C}$, $R^{33C}$, $R^{34C}$, $R^{41C}$, $R^{42C}$, $R^{43C}$ and $R^{44C}$ is a group represented by the formula (E-1), it is preferable that at least one of $R^{11C}$, $R^{12C}$, $R^{13C}$, $R^{21C}$, $R^{22C}$, $R^{23C}$, $R^{31C}$, $R^{32C}$, $R^{33C}$, $R^{41C}$, $R^{42C}$ and $R^{43C}$ is a group represented by the formula (E-1), it is more preferable that at least one of $R^{11C}$, $R^{12C}$, $R^{13C}$, $R^{21C}$, $R^{22C}$ and $R^{23C}$ is a group represented by the formula (E-1), it is further preferable that at least one of $R^{12C}$ and $R^{22C}$ is a group represented by the formula (E-1), it is particularly preferable that $R^{12C}$ and $R^{22C}$ are each a group represented by the formula (E-1).

In the compound represented by the formula (C-2-1), when at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is a group represented by the formula (D-A), the formula (D-B) or the formula (D-C) described later, it is preferable that at least one of $R^{11C}$, $R^{12C}$, $R^{13C}$, $R^{21C}$, $R^{22C}$, $R^{23C}$, $R^{31C}$, $R^{32C}$, $R^{32C}$, $R^{33C}$, $R^{41C}$, $R^{42C}$ and $R^{43C}$ is a group represented by the formula (D-A), the formula (D-B) or the formula (D-C), it is more preferable that at least one of $R^{11C}$, $R^{12C}$, $R^{13C}$, $R^{21C}$, $R^{22C}$ and $R^{23C}$ is a group represented by the formula (D-A), the formula (D-B) or the formula (D-C), it is further preferable that at least one of $R^{13C}$ and $R^{23C}$ is a group represented by the formula (D-A), the formula (D-B) or the formula (D-C), it is particularly preferable that at least one of $R^{13C}$ and $R^{23C}$ is a group represented by the formula (D-A).

In the compound represented by the formula (C-2-2), $R^{11C}$, $R^{12C}$, $R^{13C}$, $R^{14C}$, $R^{21C}$, $R^{22C}$, $R^{23C}$ and $R^{24C}$ are each preferably a hydrogen atom, an alkyl group, a cycloalkyl group, an aryl group, a monovalent heterocyclic group or a substituted amino group, more preferably a hydrogen atom, an aryl group, a monovalent heterocyclic group or a substituted amino group, further preferably a hydrogen atom or a group represented by the formula (D-1), the formula (E-1), the formula (D-A) described later, the formula (D-B) described later or the formula (D-C) described later, particularly preferably a hydrogen atom or a group represented by the formula (D-1) or the formula (E-1), especially preferably a hydrogen atom or a group represented by the formula (E-1), and the foregoing groups optionally further have a substituent.

In the compound represented by the formula (C-2-2), at least one of $R^{11C}$, $R^{12C}$, $R^{13C}$, $R^{14C}$, $R^{21C}$, $R^{22C}$, $R^{23C}$ and $R^{24C}$ is preferably an aryl group, a monovalent heterocyclic group or a substituted amino group, more preferably a group represented by the formula (D-1), the formula (E-1), the formula (D-A) described later, the formula (D-B) described later or the formula (D-C) described later, further preferably a group represented by the formula (D-1) or the formula (E-1), particularly preferably a group represented by the formula (E-1), and the foregoing groups optionally further have a substituent.

In the compound represented by the formula (C-2-2), when at least one of $R^{11C}$, $R^{12C}$, $R^{13C}$, $R^{14C}$, $R^{21C}$, $R^{22C}$, $R^{23C}$ and $R^{24C}$ is an aryl group, a monovalent heterocyclic group or a substituted amino group, the total number of the aryl group, the monovalent heterocyclic group or the substituted amino group represented by $R^{11C}$, $R^{12C}$, $R^{13C}$, $R^{14C}$, $R^{21C}$, $R^{22C}$, $R^{23C}$ and $R^{24C}$ is preferably 1 to 5, more preferably 1 to 3, further preferably 1 or 2, particularly preferably 2.

In the compound represented by the formula (C-2-2), when at least one of $R^{11C}$, $R^{12C}$, $R^{13C}$, $R^{14C}$, $R^{21C}$, $R^{22C}$, $R^{23C}$ and $R^{24C}$ is a group represented by the formula (D-1), the formula (E-1), the formula (D-A) described later, the formula (D-B) described later or the formula (D-C) described later, the total number of the group represented by the formula (D-1), the formula (E-1), the formula (D-A), the formula (D-B) or the formula (D-C) represented by $R^{11C}$, $R^{12C}$, $R^{13C}$, $R^{14C}$, $R^{21C}$, $R^{22C}$, $R^{23C}$ and $R^{24C}$ is preferably 1 to 5, more preferably 1 to 3, further preferably 1 or 2, particularly preferably 2.

In the compound represented by the formula (C-2-2), when at least one of $R^{11C}$, $R^{12C}$, $R^{13C}$, $R^{14C}$, $R^{21C}$, $R^{22C}$, $R^{23C}$ and $R^{24C}$ is an aryl group, a monovalent heterocyclic group or a substituted amino group, it is preferable that at least one of $R^{11C}$, $R^{12C}$, $R^{13C}$, $R^{21C}$, $R^{22C}$ and $R^{23C}$ is an aryl group, a monovalent heterocyclic group or a substituted amino group, it is more preferable that at least one of $R^{12C}$ and $R^{22C}$ is an aryl group, a monovalent heterocyclic group or a substituted amino group.

In the compound represented by the formula (C-2-2), when at least one of $R^{11C}$, $R^{12C}$, $R^{13C}$, $R^{14C}$, $R^{21C}$, $R^{22C}$, $R^{23C}$ and $R^{24C}$ is a group represented by the formula (D-1), the formula (E-1), the formula (D-A) described later, the formula (D-B) described later or the formula (D-C) described later, it is preferable that at least one of $R^{11C}$, $R^{12C}$, $R^{13C}$, $R^{21C}$, $R^{22C}$ and $R^{23C}$ is a group represented by the formula (D-1), the formula (E-1), the formula (D-A), the formula (D-B) or the formula (D-C), it is more preferable that at least one of $R^{12C}$ and $R^{22C}$ is a group represented by the formula (D-1), the formula (E-1), the formula (D-A), the formula (D-B) or the formula (D-C), it is further preferable that at least one of $R^{12C}$ and $R^{22C}$ is a group represented by the formula (D-1) or the formula (E-1), it is particularly preferable that at least one of $R^{12C}$ and $R^{22C}$ is a group represented by the formula (E-1).

In the compound represented by the formula (C-2-1) and the formula (C-2-2), the examples and preferable ranges of the aryl group, the monovalent heterocyclic group and the substituted amino group represented by $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ are the same as the examples and preferable ranges of the aryl group, the monovalent heterocyclic group and the substituted amino group as the substituent which Ring $R^{1C}$ and Ring $R^{2C}$ optionally have, respectively.

In the compound represented by the formula (C-2-1) and the formula (C-2-2), the examples and preferable ranges of the substituent which $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ optionally have are the same as the examples and preferable ranges of the substituent which the substituent which Ring $R^{1C}$ and Ring $R^{2C}$ optionally have optionally further has.

In the compound represented by the formula (C-2-1) and the formula (C-2-2), $R^{11C}$ and $R^{12C}$, $R^{12C}$ and $R^{13C}$, $R^{13C}$ and $R^{14C}$, $R^{14C}$ and $R^{34C}$, $R^{34C}$ and $R^{33C}$, $R^{33C}$ and $R^{32C}$, $R^{32C}$ and $R^{31C}$, $R^{31C}$ and $R^{41C}$, $R^{41C}$ and $R^{42C}$, $R^{42C}$ and $R^{43C}$, $R^{43C}$ and $R^{44C}$, $R^{44C}$ and $R^{24C}$, $R^{24C}$ and $R^{23C}$, $R^{23C}$ and $R^{22C}$, $R^{22C}$ and $R^{21C}$, and $R^{21C}$ and $R^{11C}$ may each be combined together to form a ring together with the carbon atoms to which they are attached, but it is preferable that they do not form a ring.

The compound represented by the formula (C-2-1) is preferably a compound represented by the formula (C-3-1), since the light emitting device of the present invention is more excellent in external quantum efficiency.

The compound represented by the formula (C-2-2) is preferably a compound represented by the formula (C-3-2), since the light emitting device of the present invention is more excellent in external quantum efficiency.

The compound represented by the formula (C-1) includes, for example, compounds represented by the formula (C-101) to the formula (C-146).

[Chemical Formula 30]

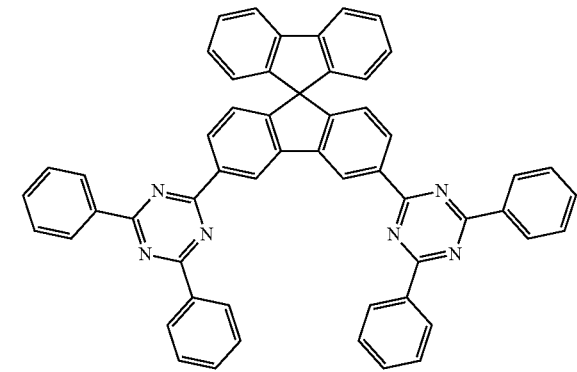

(C-101)

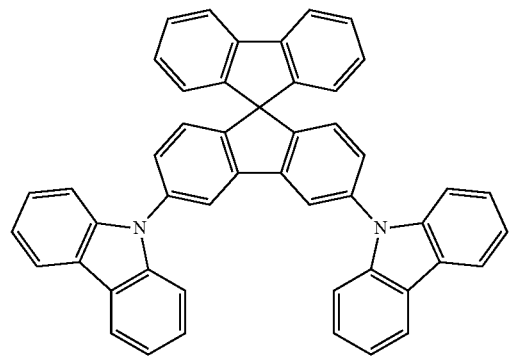

(C-102)

(C-103)
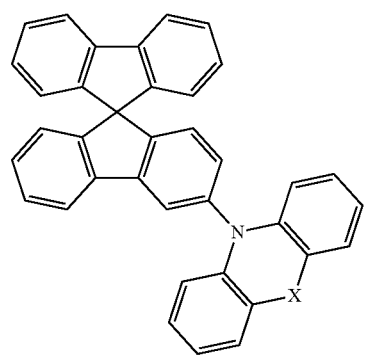
(C-104)
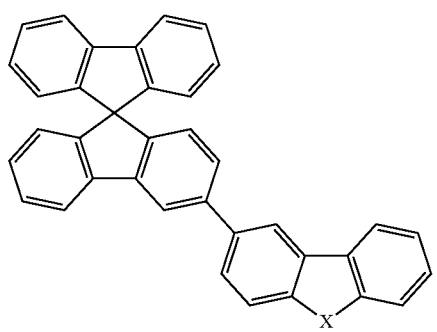
[Chemical Formula 31]
(C-105)
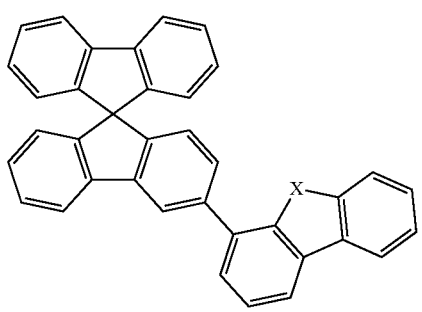
(C-106)
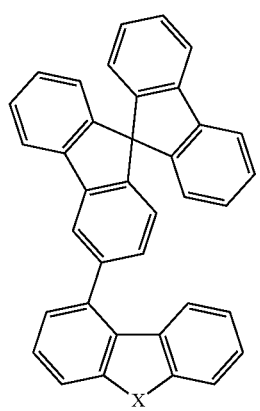
(C-107)
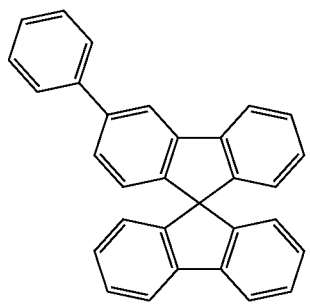
(C-108)
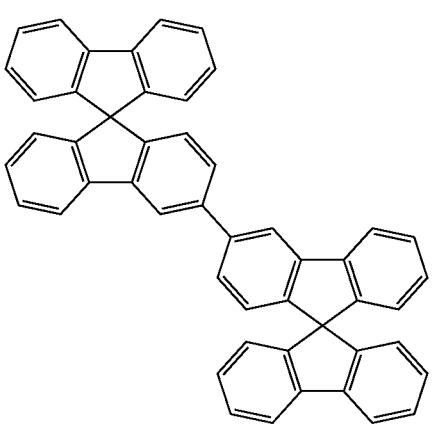
(C-109)
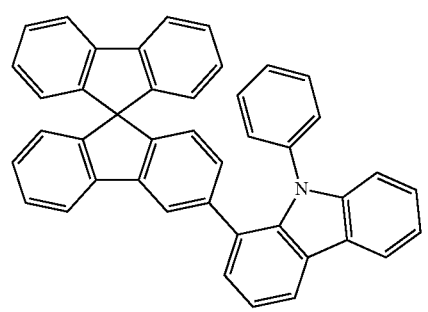
[Chemical Formula 32]
(C-110)
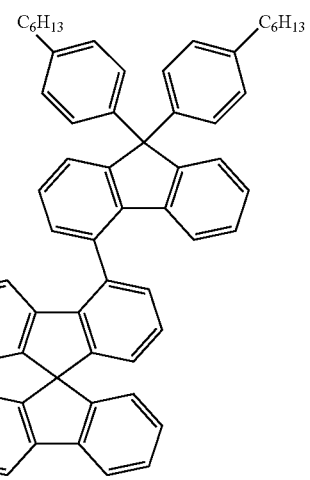

(C-111)
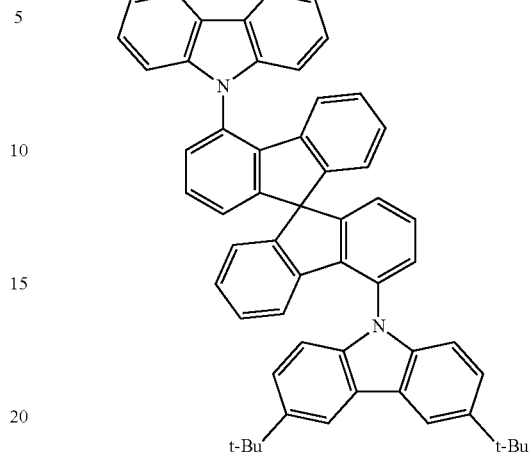
(C-114)
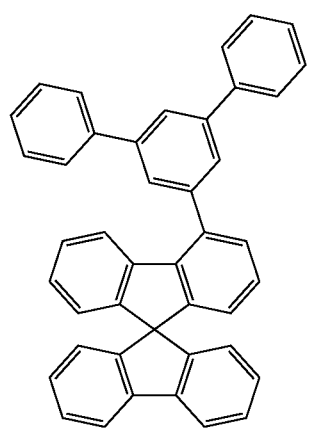
(C-115)
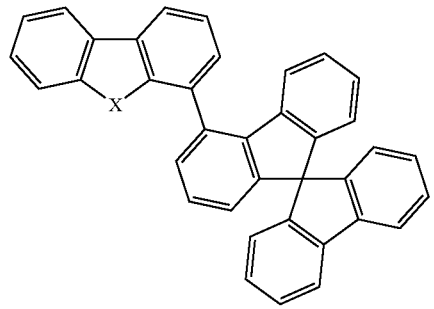
[Chemical Formula 33]
(C-112)
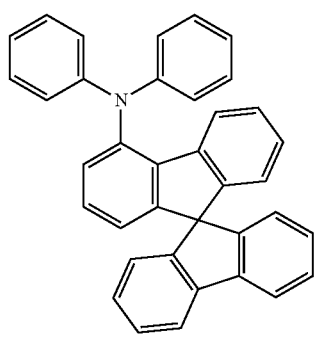
(C-116)
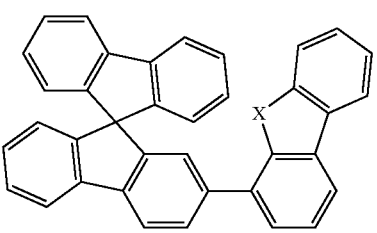
(C-113)
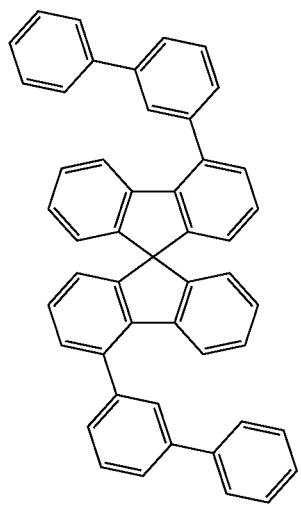
(C-117)
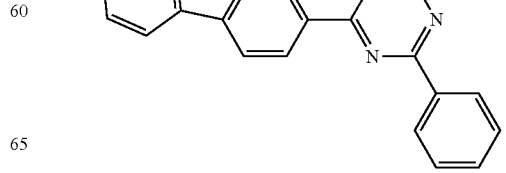

(C-118)
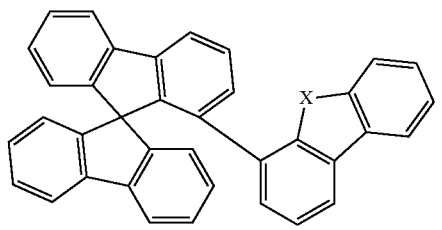
(C-119)
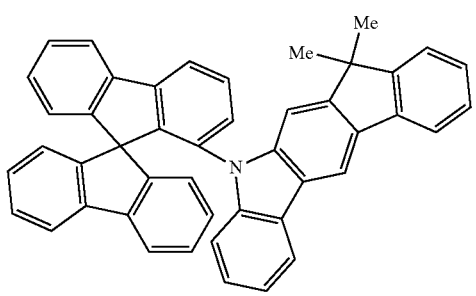
[Chemical Formula 34]
(C-120)
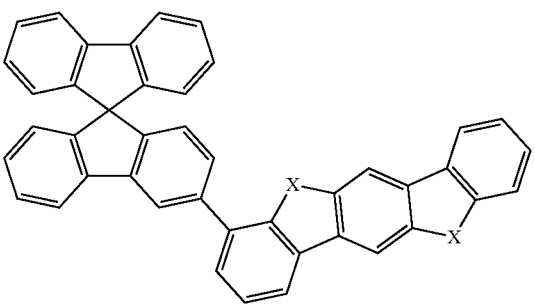
(C-121)
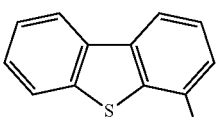
(C-122)
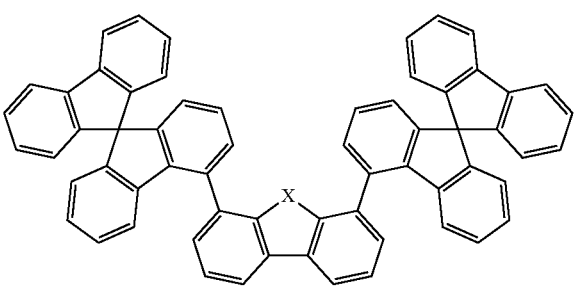
(C-123)
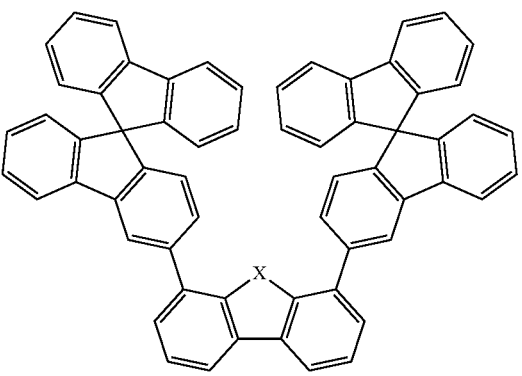
[Chemical Formula 35]
(C-124)
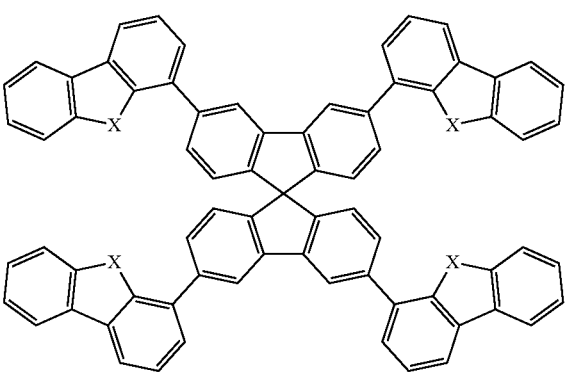
(C-125)
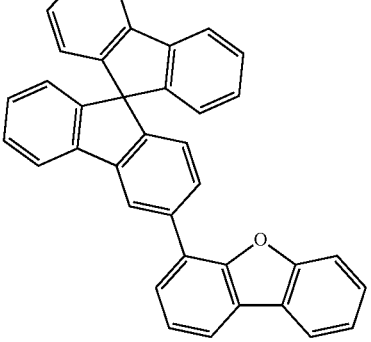

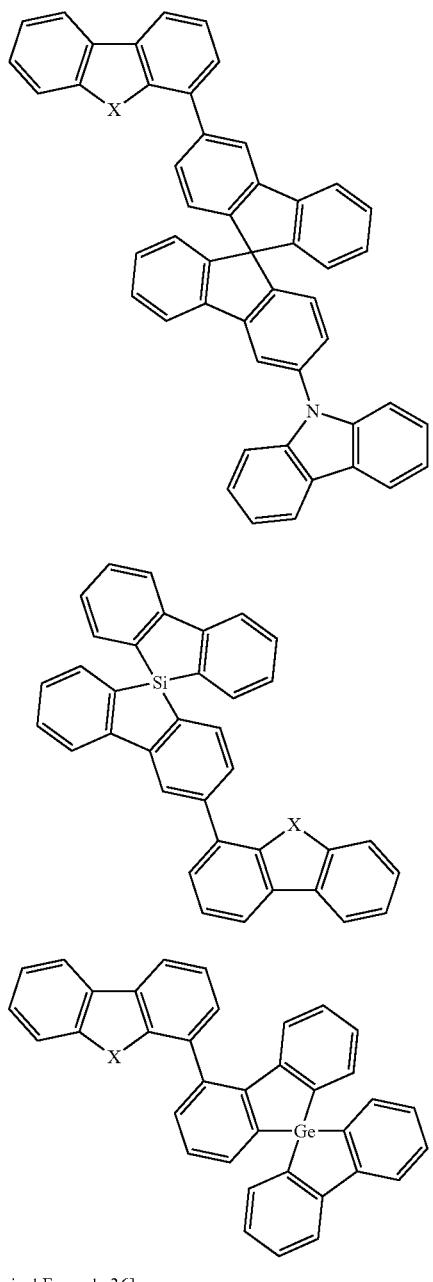
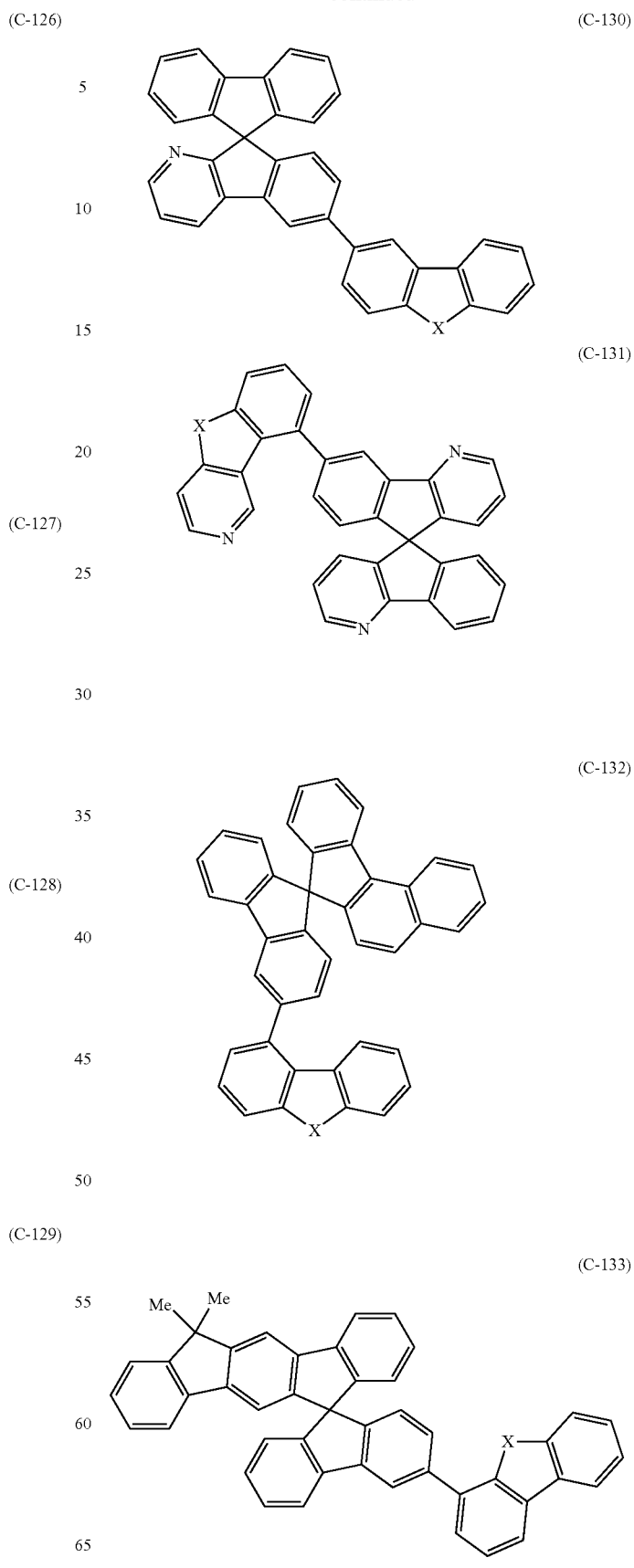

[Chemical Formula 37]
(C-134)
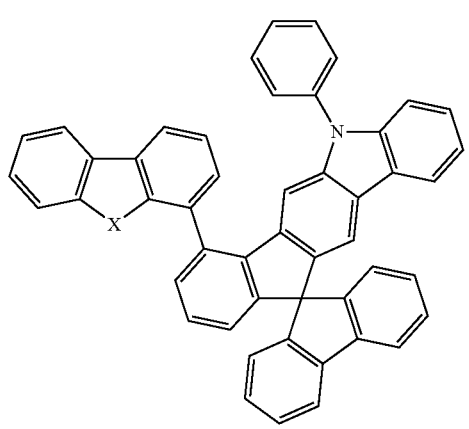
(C-135)
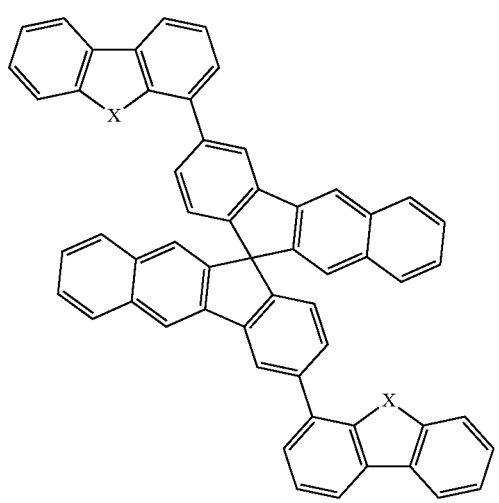
(C-136)
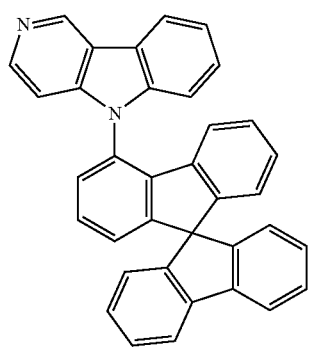
(C-137)
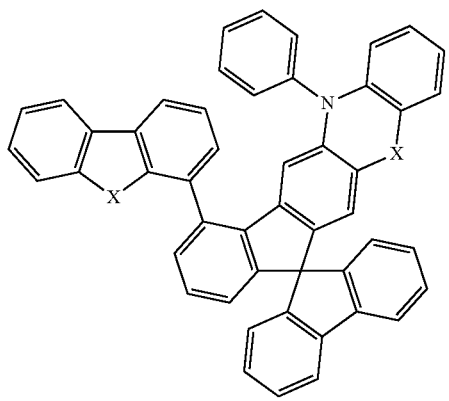
[Chemical Formula 38]
(C-138)
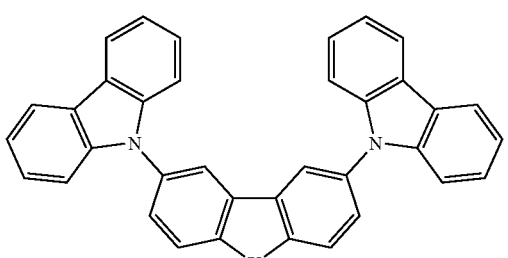
(C-139)
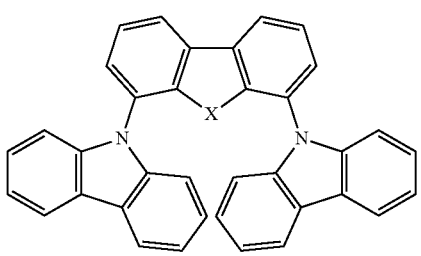
(C-140)

[Chemical Formula 39]

(C-141)

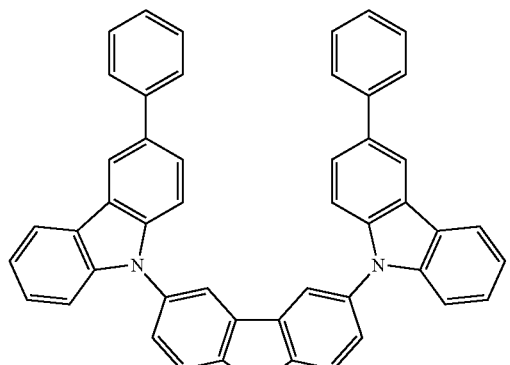

(C-142)

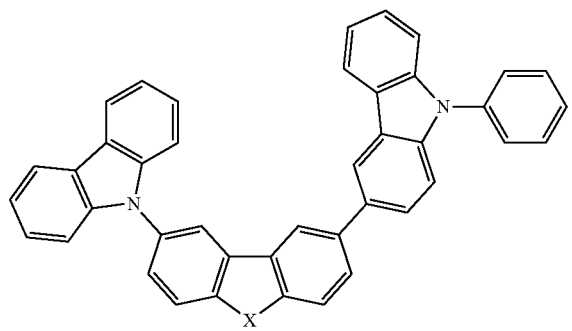

[Chemical Formula 40]

(C-143)

(C-144)

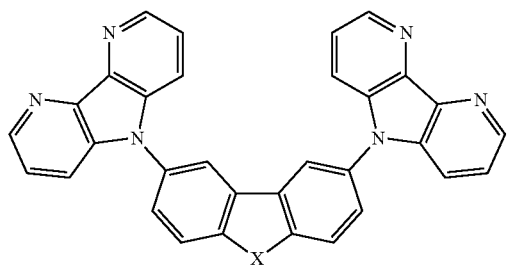

(C-145)

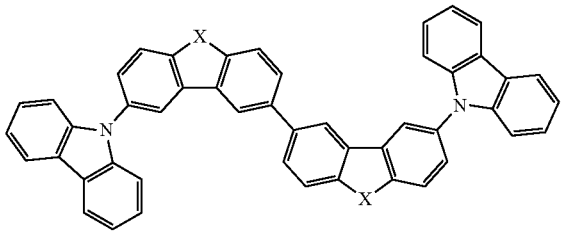

(C-146)

[wherein, X represents an oxygen atom or a sulfur atom. When a plurality of X are present, they may be the same or different.]

X is preferably a sulfur atom.

The compound represented by the formula (C-1) is available from, for example, Aldrich, and Luminescence Technology Corp. The compound represented by the formula (C-1) can be synthesized according to methods described in, for example, International Publication WO 2014/023388, International Publication WO 2013/045408, International Publication WO 2013/045410, International Publication WO 2013/045411, International Publication WO 2012/048820, International Publication WO 2012/048819, International Publication WO 2011/006574, "Organic Electronics vol. 14, 902-908 (2013)", International Publication WO 2009/096202, International Publication WO 2009/086028, Japanese Unexamined Patent Application Publication (JP-A) No. 2009-267255 and JP-A No. 2009-46408, as other means.

In the composition of the present invention, the two or more compounds represented by the formula (C-1) are each preferably a host material having at least one function selected from hole injectability, hole transportability, electron injectability and electron transportability, since the light emitting device of the present invention is more excellent in external quantum efficiency.

In the composition of the present invention, the lowest excited triplet state ($T_1$) of the two or more compounds represented by the formula (C-1) is preferably at energy level corresponding to that of the phosphorescent compound or higher energy level than it, more preferably at higher energy level than it, since the light emitting device of the present invention is more excellent in external quantum efficiency.

In the composition of the present invention, the two or more compounds represented by the formula (C-1) are each preferably one that shows solubility in a solvent which is capable of dissolving the phosphorescent compound, since the light emitting device of the present invention can be fabricated by a solution application process.

"The phosphorescent compound" usually means a compound showing phosphorescence at room temperature (25° C.), and is preferably a metal complex showing light emission from triplet excited state at room temperature. This metal complex showing light emission from triplet excited state has a central metal atom and a ligand.

The central metal atom includes, for example, a metal atom having an atomic number of 40 or more, which has spin-orbit interaction in the complex and can cause intersystem crossing between singlet state and triplet state. The metal atom includes, for example, a ruthenium atom, a rhodium atom, a palladium atom, an iridium atom and a platinum atom, and it is preferably an iridium atom or a platinum atom since the external quantum efficiency of the light emitting device of the present invention is more excellent.

The ligand includes, for example, a neutral or anionic monodentate ligand or a neutral or anionic polydentate ligand which forms at least one kind of bond selected from the group consisting of a coordinate bond and a covalent bond with a central metal atom. The bond between the central metal atom and the ligand includes, for example, a metal-nitrogen bond, a metal-carbon bond, a metal-oxygen bond, a metal-phosphorus bond, a metal-sulfur bond and a metal-halogen bond. The polydentate ligand usually means a bidentate or more and six-dentate or less ligand.

Phosphorescent Compound Represented by the Formula (1)

The phosphorescent compound is preferably a phosphorescent compound represented by the formula (1).

M is preferably an iridium atom or a platinum atom, more preferably an iridium atom, since the light emitting device of the present invention is more excellent in external quantum efficiency.

When M is a ruthenium, a rhodium atom or an iridium atom, $n^1$ is preferably 2 or 3, more preferably 3.

When M is a palladium atom or a platinum atom, $n^1$ is preferably 2.

$E^1$ and $E^2$ are each preferably a carbon atom.

Ring $L^1$ is preferably a 5-membered aromatic hetero ring or a 6-membered aromatic hetero ring, more preferably a 5-membered aromatic hetero ring having 2 or more and 4 or less nitrogen atoms as a constituent atom or a 6-membered aromatic hetero ring having 1 or more and 4 or less nitrogen atoms as a constituent atom, further preferably a 5-membered aromatic hetero ring having 2 or more and 3 or less nitrogen atoms as a constituent atom or a 6-membered aromatic hetero ring having 1 or more and 2 or less nitrogen atoms as a constituent atom, and the foregoing rings optionally have a substituent. When Ring $L^1$ is a 6-membered aromatic hetero ring, $E^1$ is preferably a carbon atom.

Ring $L^1$ includes, for example, a diazole ring, a pyridine ring, a diazabenzene ring, a triazine ring, an azanaphthalene ring and a dianaphthalene ring, and is preferably a diazole ring, a pyridine ring, a diazabenzene ring, a quinoline ring or an isoquinoline, more preferably a diazole ring, a pyridine ring, a quinoline ring or an isoquinoline ring, further preferably an imidazole ring, a pyridine ring or an isoquinoline ring, and the foregoing rings optionally have a substituent.

Ring $L^2$ is preferably a 5-membered or 6-membered aromatic hydrocarbon ring, or a 5-membered or 6-membered aromatic hetero ring, more preferably a 6-membered aromatic hydrocarbon ring or a 6-membered aromatic hetero ring, further preferably a 6-membered aromatic hydrocarbon ring, and the foregoing rings optionally have a substituent. When Ring $R^2$ is a 6-membered aromatic hetero ring, $E^2$ is preferably a carbon atom.

Ring $L^2$ includes, for example, a benzene ring, a naphthalene ring, a fluorene ring, a phenanthrene ring, an indene ring, a pyridine ring, a diazabenzene ring and a triazine ring, and is preferably a benzene ring, a naphthalene ring, a fluorene ring, a pyridine ring or a diazabenzene ring, more preferably a benzene ring, a pyridine ring or a diazabenzene ring, further preferably a benzene ring, and the foregoing rings optionally have a substituent.

The substituent which Ring $L^1$ and Ring $L^2$ optionally have is preferably an alkyl group, a cycloalkyl group, an alkoxy group, a cycloalkoxy group, an aryl group, an aryloxy group, a monovalent heterocyclic group, a substituted amino group or a halogen atom, more preferably an alkyl group, a cycloalkyl group, an alkoxy group, a cycloalkoxy group, an aryl group, a monovalent heterocyclic group, a substituted amino group or a fluorine atom, further preferably an alkyl group, a cycloalkyl group, an aryl group, a monovalent heterocyclic group, a substituted amino group or a fluorine atom, particularly preferably an aryl group, a monovalent heterocyclic group or a fluorine atom, especially preferably an aryl group, and the foregoing groups optionally further have a substituent.

The aryl group as the substituent which Ring $L^1$ and Ring $L^2$ optionally have is preferably a phenyl group, a naphthyl group, an anthracenyl group, a phenanthrenyl group, a dihydrophenanthrenyl group, a fluorenyl group or a pyrenyl group, more preferably a phenyl group, a naphthyl group or a fluorenyl group, further preferably a phenyl group, and the foregoing groups optionally further have a substituent.

The monovalent heterocyclic group as the substituent which Ring $L^1$ and Ring $L^2$ optionally have is preferably a pyridyl group, a pyrimidinyl group, a triazinyl group, a quinolinyl group, an isoquinolinyl group, a dibenzofuranyl group, a dibenzothienyl group, a carbazolyl group, an azacarbazolyl group, a diazacarbazolyl group, a phenoxazinyl group or a phenothiazinyl group, more preferably a pyridyl group, a pyrimidinyl group, a triazinyl group, a carbazolyl group, an azacarbazolyl group or a diazacarbazolyl group, further preferably a pyridyl group, a pyrimidinyl group or a triazinyl group, particularly preferably a triazinyl group, and the foregoing groups optionally further have a substituent.

In the substituted amino group as the substituent which Ring $L^1$ and Ring $L^2$ optionally have, the substituent which the amino group has is preferably an aryl group or a monovalent heterocyclic group, more preferably an aryl group, and the foregoing groups optionally further have a substituent. The examples and preferable ranges of the aryl group as the substituent which the amino group has are the same as the examples and preferable ranges of the aryl group as the substituent which Ring $L^1$ and Ring $L^2$ optionally have. The examples and preferable ranges of the monovalent heterocyclic group as the substituent which the amino group has are the same as the examples and preferable ranges of the monovalent heterocyclic group as the substituent which Ring L and Ring $L^2$ optionally have.

The substituent which the substituent which Ring $L^1$ and Ring $L^2$ optionally have optionally further has is preferably an alkyl group, a cycloalkyl group, an aryl group, a monovalent heterocyclic group, an alkoxy group, a cycloalkoxy group or a substituted amino group, more preferably an alkyl group, a cycloalkyl group, an aryl group, a monovalent heterocyclic group or a substituted amino group, further preferably an alkyl group, a cycloalkyl group or an aryl group, particularly preferably an alkyl group or a cycloalkyl group, and the foregoing groups optionally further have a substituent, but it is preferable that these groups do not further have a substituent.

The aryl group, the monovalent heterocyclic group or the substituted amino group as the substituent which Ring $L^1$ and Ring $L^2$ optionally have is preferably a group represented by the formula (D-A), the formula (D-B) or the formula (D-C), more preferably a group represented by the formula (D-A) or the formula (D-C), since the light emitting device of the present invention is more excellent in external quantum efficiency.

[Chemical Formula 41]

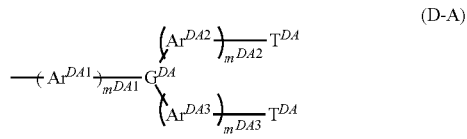

(D-A)

[wherein, $m^{DA1}$, $m^{DA2}$ and $m^{DA1}$ each independently represent an integer of 0 or more.

$G^{DA}$ represents a nitrogen atom, an aromatic hydrocarbon group or a heterocyclic group, and the foregoing groups optionally have a substituent.

$Ar^{DA1}$, $Ar^{DA2}$ and $Ar^{DA3}$ each independently represent an arylene group or a divalent heterocyclic group, and the foregoing groups optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and the foregoing groups optionally have a substituent. A plurality of $T^{DA}$ may be the same or different.]

[Chemical Formula 42]

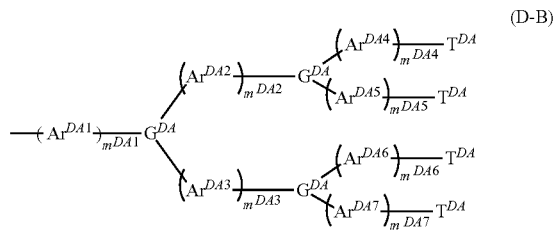

(D-B)

[wherein, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, and the foregoing groups optionally have a substituent. A plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and the foregoing groups optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.

$T^{DA}$ represents an aryl group or a monovalent heterocyclic group, and the foregoing groups optionally have a substituent. A plurality of $T^{DA}$ may be the same or different.]

[Chemical Formula 43]

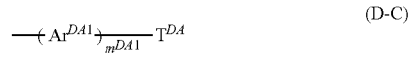

(D-C)

[wherein, $m^{DA1}$ represents an integer of 0 or more.

$Ar^{DA1}$ represents an arylene group or a divalent heterocyclic group, and the foregoing groups optionally have a substituent. When a plurality of $Ar^{DA1}$ are present, they may be the same or different.

$T^{DA}$ represents an aryl group or a monovalent heterocyclic group, and the foregoing groups optionally have a substituent.]

$m^{DA1}$, $m^{DA2}$, $m^{DA3}$, $m^{DA4}$, $m^{DA5}$ $m^{DA6}$ and $m^{DA7}$ are each usually an integer of 10 or less, preferably an integer of 5 or less, more preferably an integer of 2 or less, further preferably 0 or 1. It is preferable that $m^{DA2}$, $m^{DA3}$, $m^{DA4}$, $m^{DA5}$ $m^{DA6}$ and $m^{DA7}$ are the same integer.

$G^{DA}$ is preferably an aromatic hydrocarbon group or a heterocyclic group, more preferably a group obtained by removing from a benzene ring, a pyridine ring, a pyrimidine ring, a triazine ring or a carbazole ring three hydrogen atoms bonding directly to carbon atoms or nitrogen atoms constituting the ring, and the foregoing groups optionally have a substituent.

The substituent which $G^{DA}$ optionally has is preferably an alkyl group, a cycloalkyl group, an alkoxy group, a cycloalkoxy group, an aryl group or a monovalent heterocyclic group, more preferably an alkyl group, a cycloalkyl group, an alkoxy group or a cycloalkoxy group, further preferably an alkyl group or a cycloalkyl group, and the foregoing groups optionally further have a substituent, but it is preferable that these groups do not further have a substituent.

$G^{DA}$ is preferably a group represented by the formula (GDA-11) to the formula (GDA-15), more preferably a group represented by the formula (GDA-11) to the formula (GDA-14), further preferably a group represented by the formula (GDA-11) or the formula (GDA-14), particularly preferably a group represented by the formula (GDA-11).

[Chemical Formula 44]

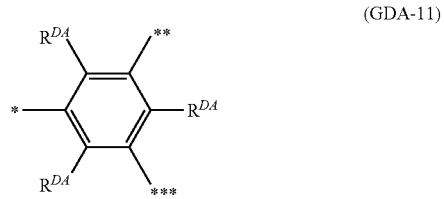

(GDA-11)

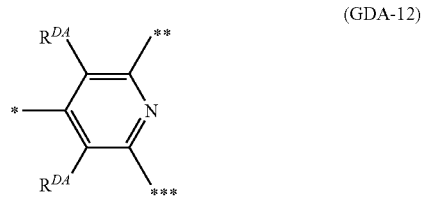

(GDA-12)

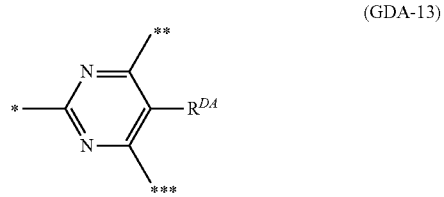

(GDA-13)

(GDA-14)

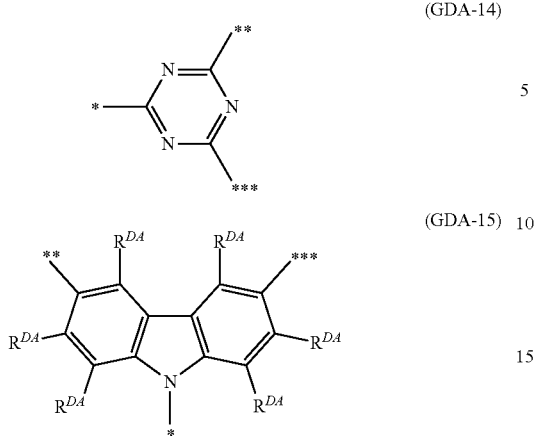

(GDA-15)

[wherein,
\* represents a bond to $Ar^{DA1}$ in the formula (D-A), to $Ar^{DA1}$ in the formula (D-B), to $Ar^{DA2}$ in the formula (D-B) or to $Ar^{DA3}$ in the formula (D-B).
\*\* represents a bond to $Ar^{DA2}$ in the formula (D-A), to $Ar^{DA2}$ in the formula (D-B), to $Ar^{DA4}$ in the formula (D-B) or to $Ar^{DA6}$ in the formula (D-B).
\*\*\* represents a bond to $Ar^{DA3}$ in the formula (D-A), to $Ar^{DA3}$ in the formula (D-B), to $Ar^{DA5}$ in the formula (D-B) or to $Ar^{DA7}$ in the formula (D-B).
$R^{DA}$ represents a hydrogen atom, an alkyl group, a cycloalkyl group, an alkoxy group, a cycloalkoxy group, an aryl group or a monovalent heterocyclic group, and the foregoing groups optionally further have a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or a cycloalkyl group, and the foregoing groups optionally have a substituent.

$Ar^{DA1}$, $Ar^{DA2}$, $Ar^{DA3}$, $Ar^{DA4}$, $Ar^{DA5}$, $Ar^{DA6}$ and $Ar^{DA7}$ are each preferably a phenylene group, a fluorenediyl group or a carbazolediyl group, more preferably a group represented by the formula (ArDA-1) to the formula (ArDA-5), further preferably a group represented by the formula (ArDA-1) to the formula (ArDA-3), particularly preferably a group represented by the formula (ArDA-1) or the formula (ArDA-2), and the foregoing groups optionally have a substituent.

[Chemical Formula 45]

(ArDA-1)

(ArDA-2)

(ArDA-3)

(ArDA-4)

(ArDA-5)

[wherein,
$R^{DA}$ represents the same meaning as described above.
$R^{DB}$ represents a hydrogen atom, an alkyl group, a cycloalkyl group, an aryl group or a monovalent heterocyclic group, and the foregoing groups optionally have a substituent. When a plurality of $R^{DB}$ are present, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

The examples and preferable ranges of the substituent which $Ar^{DA1}$, $Ar^{DA2}$, $Ar^{DA3}$, $Ar^{DA4}$, $Ar^{DA5}$, $Ar^{DA6}$, $Ar^{DA7}$ and $R^{DB}$ optionally have are the same as the examples and preferable ranges of the substituent which $G^{DA}$ optionally has.

$T^{DA}$ is preferably a group represented by the formula (TDA-1) to the formula (TDA-3), more preferably a group represented by the formula (TDA-1)

[Chemical Formula 46]

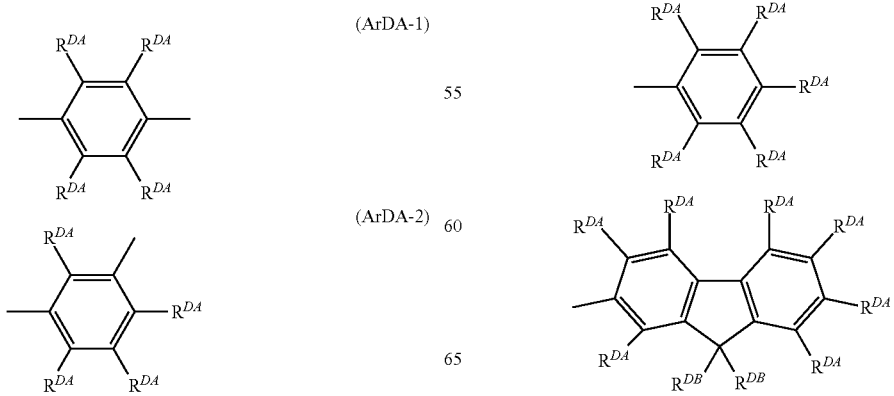

(TDA-1)

(TDA-2)

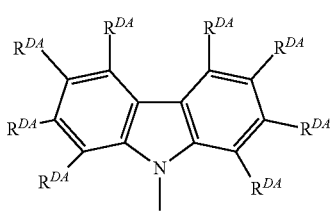
(TDA-3)

[wherein, $R^{DA}$ and $R^{DB}$ represent the same meaning as described above.]

The group represented by the formula (D-A) is preferably a group represented by the formula (D-A1) to the formula (D-A5), more preferably a group represented by the formula (D-A1) or the formula (D-A3) to the formula (D-A5), further preferably a group represented by the formula (D-A1) or the formula (D-A5).

[Chemical Formula 47]

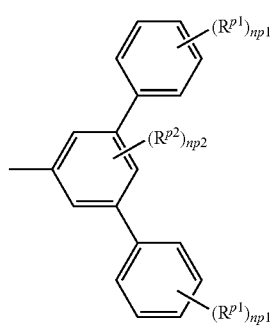
(D-A1)

(D-A2)

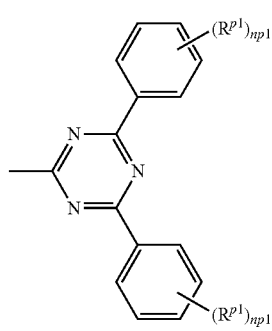
(D-A3)

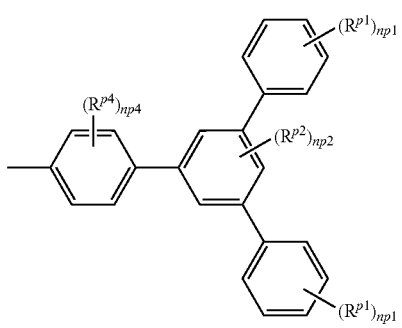
(D-A4)

(D-A5)

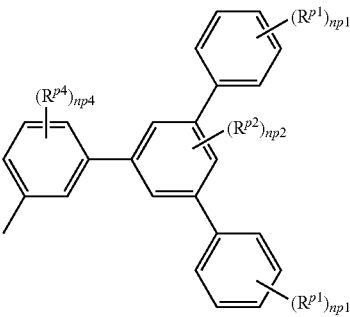

[wherein, $R^{p1}$, $R^{p2}$, $R^{p3}$ and $R^{p4}$ each independently represent an alkyl group, a cycloalkyl group, an alkoxy group, a cycloalkoxy group or a halogen atom. When a plurality of $R^{p1}$, $R^{p2}$ and $R^{p4}$ are present, they may be the same or different at each occurrence.

np1 represents an integer of 0 to 5, np2 represents an integer of 0 to 3, np3 represents 0 or 1, and np4 represents an integer of 0 to 4. A plurality of np1 may be the same or different.]

The group represented by the formula (D-B) is preferably a group represented by the formula (D-B1) to the formula (D-B6), more preferably a group represented by the formula (D-B1) to the formula (D-B3) or the formula (D-B5), further preferably a group represented by the formula (D-B1) or the formula (D-B3).

[Chemical Formula 48]

(D-B1)
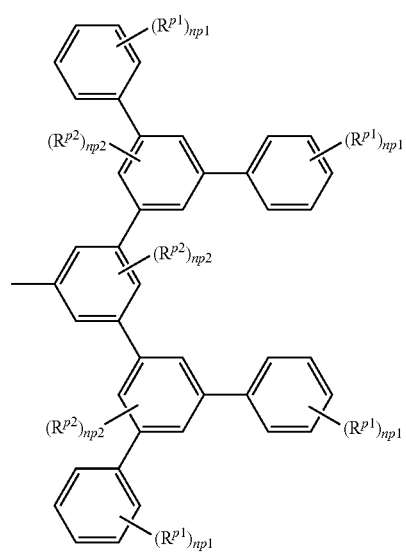
(D-B2)
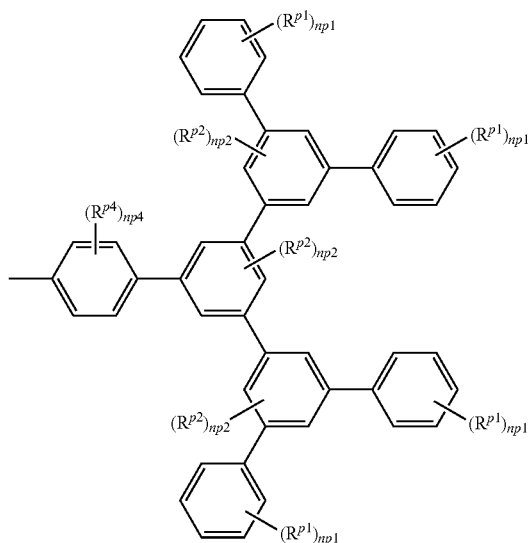
(D-B3)
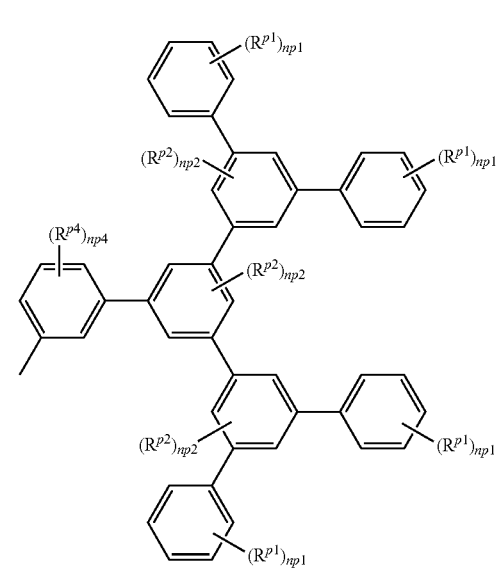
[Chemical Formula 49]
(D-B4)
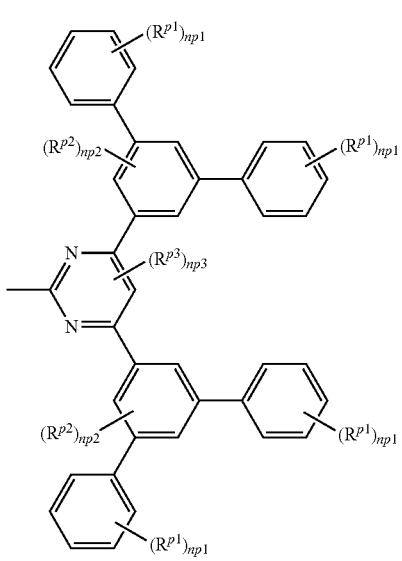

(D-B5)

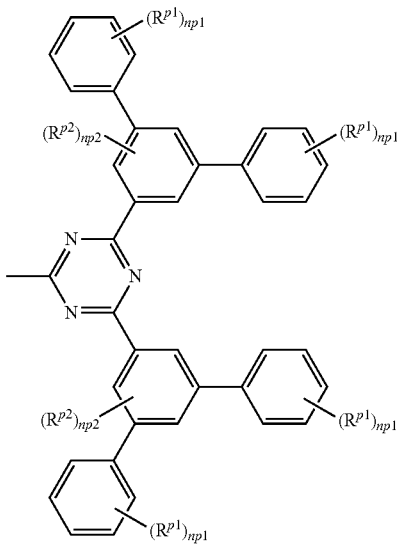

(D-C1)

(D-C2)

(D-C3)

(D-C4)

(D-B6)

[wherein,
$R^{p4}$, $R^{p5}$ and $R^{p6}$ each independently represent an alkyl group, a cycloalkyl group, an alkoxy group, a cycloalkoxy group or a halogen atom. When a plurality of $R^{p4}$, $R^{p5}$ and $R^{p6}$ are present, they may be the same or different at each occurrence.

np4 represents an integer of 0 to 4, np5 represents an integer of 0 to 5, and np6 represents an integer of 0 to 5.]

np1 is preferably an integer of 0 to 2, more preferably 0 or 1. np2 is preferably 0 or 1, more preferably 0. np3 is preferably 0. np4 is preferably an integer of 0 to 2, more preferably 0. np5 is preferably an integer of 0 to 3, more preferably 0 or 1. np6 is preferably an integer of 0 to 2, more preferably 0 or 1.

The alkyl group or the cycloalkyl group represented by $R^{p1}$, $R^{p2}$, $R^{p3}$, $R^{p4}$, $R^{p5}$ and $R^{p6}$ is preferably a methyl group, an ethyl group, an isopropyl group, a tert-butyl group, a hexyl group, a 2-ethylhexyl group, a cyclohexyl group or a tert-octyl group.

The alkoxy group or the cycloalkoxy group represented by $R^{p1}$, $R^{p2}$, $R^{p3}$, $R^{p4}$, $R^{p5}$ and $R^{p6}$ is preferably a methoxy group, a 2-ethylhexyloxy group or a cyclohexyloxy group.

$R^{p1}$, $R^{p2}$, $R^{p3}$, $R^{p4}$, $R^{p5}$ and $R^{p6}$ are each preferably an alkyl group optionally having a substituent or a cycloalkyl group optionally having a substituent, more preferably an alkyl group optionally having a substituent, further preferably a methyl group, an ethyl group, an isopropyl group, a tert-butyl group, a hexyl group, a 2-ethylhexyl group or a tert-octyl group.

When a plurality of the substituents which Ring $L^1$ optionally has are present, it is preferable that they are not combined together to form a ring together with the atoms to which they are attached.

When a plurality of the substituents which Ring $L^2$ optionally has are present, it is preferable that they are not combined together to form a ring together with the atoms to which they are attached.

It is preferable that the substituent which Ring $L^1$ optionally has and the substituent which Ring $L^2$ optionally has are not combined together to form a ring together with the atoms to which they are attached.

[wherein,
$R^{p1}$, $R^{p2}$, $R^{p3}$ and $R^{p4}$ each independently represent an alkyl group, a cycloalkyl group, an alkoxy group, a cycloalkoxy group or a halogen atom. When a plurality of $R^{p1}$, $R^{p2}$ and $R^{p4}$ are present, they may be the same or different at each occurrence.

np1 represents an integer of 0 to 5, np2 represents an integer of 0 to 3, np3 represents 0 or 1, and np4 represents an integer of 0 to 4. A plurality of np1 may be the same or different. A plurality of np2 may be the same or different.]

The group represented by the formula (D-C) is preferably a group represented by the formula (D-C1) to the formula (D-C4), more preferably a group represented by the formula (D-C1) or the formula (D-C2), further preferably a group represented by the formula (D-C2).

[Chemical Formula 50]

[Anionic Bidentate Ligand]

The anionic bidentate ligand represented by $A^1$-$G^1$-$A^2$ includes, for example, ligands represented by the following formulae. However, the anionic bidentate ligand represented by $A^1$-$G^1$-$A^2$ is different from a ligand of which number is defined by subscript $n^1$.

[Chemical Formula 51]

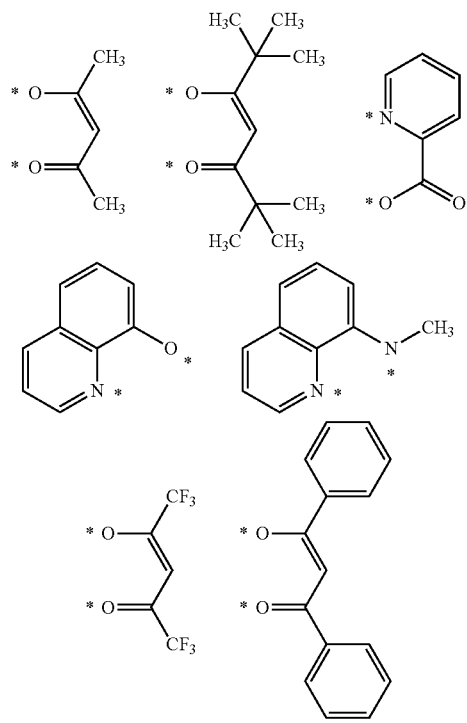

[Chemical Formula 52]

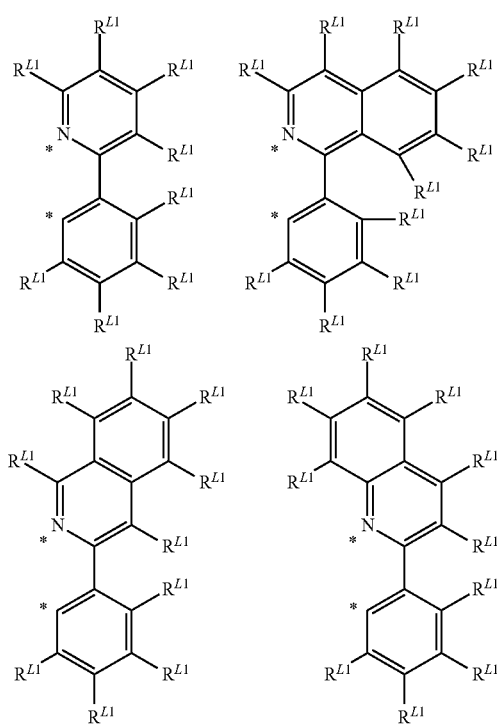

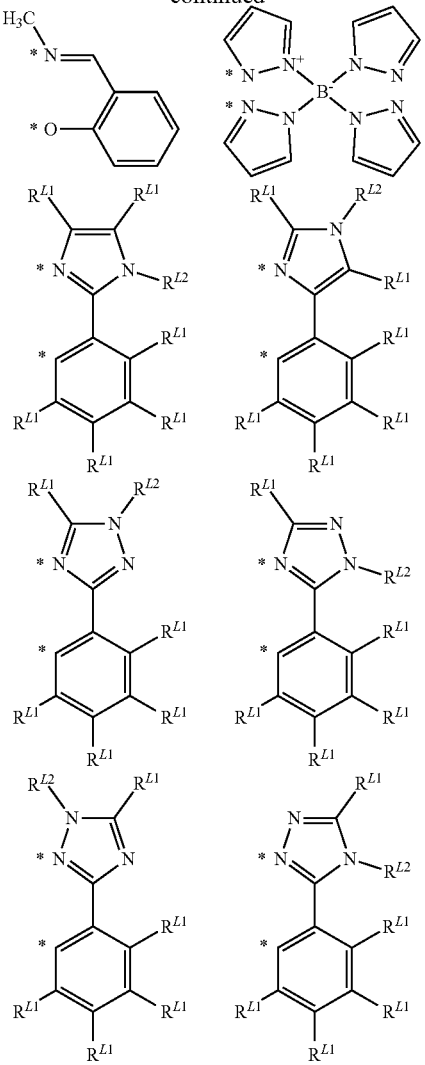

[wherein,

\* represents a site binding to M.

$R^{L1}$ represents a hydrogen atom, an alkyl group, a cycloalkyl group, an aryl group, a monovalent heterocyclic group or a halogen atom, and the foregoing groups optionally have a substituent. A plurality of $R^{L1}$ may be the same or different.

$R^{L2}$ represents an alkyl group, a cycloalkyl group, an aryl group, a monovalent heterocyclic group or a halogen atom, and the foregoing groups optionally have a substituent.]

$R^{L1}$ is preferably a hydrogen atom, an alkyl group, a cycloalkyl group, an aryl group or a fluorine atom, more preferably a hydrogen atom or an alkyl group, and the foregoing groups optionally have a substituent.

$R^{L2}$ is preferably an alkyl group or an aryl group, and the foregoing groups optionally have a substituent.

The phosphorescent compound represented by the formula (1) is preferably a phosphorescent compound represented by the formula (1-A) or a phosphorescent compound represented by the formula (1-B), since the light emitting device of the present invention is more excellent in external quantum efficiency.

[Phosphorescent Compound Represented by the Formula (1-A)]

Ring $L^{1A}$ is preferably an imidazole ring in which $E^{11A}$ is a nitrogen atom or an imidazole ring in which $E^{12A}$ is a nitrogen atom, more preferably an imidazole ring in which $E^{11A}$ is a nitrogen atom.

The examples and preferable ranges of the aryl group, the monovalent heterocyclic group and the substituted amino group represented by $R^{11A}$, $R^{12A}$, $R^{13A}$, $R^{21A}$, $R^{22A}$, $R^{23A}$ and $R^{24A}$ are the same as the examples and preferable ranges of the aryl group, the monovalent heterocyclic group and the substituted amino group as the substituent which Ring $L^1$ and Ring $L^2$ optionally have, respectively.

The examples and preferable ranges of the substituent which $R^{11A}$, $R^{12A}$, $R^{13A}$, $R^{21A}$, $R^{22A}$, $R^{23A}$ and $R^{24A}$ optionally have are the same as the examples and preferable ranges of the substituent which the substituent which Ring $L^1$ and Ring $L^2$ optionally have optionally further has.

When $E^{11A}$ is a nitrogen atom and $R^{11A}$ is present, $R^{11A}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

When $E^{11A}$ is a carbon atom, $R^{11A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, particularly preferably a hydrogen atom, and the foregoing groups optionally have a substituent.

When $E^{12A}$ is a nitrogen atom and $R^{12A}$ is present, $R^{12A}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

When $E^{12A}$ is a carbon atom, $R^{12A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, particularly preferably a hydrogen atom, and the foregoing groups optionally have a substituent.

When $E^{13A}$ is a nitrogen atom and $R^{13A}$ is present, $R^{11A}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

When $E^{13A}$ is a carbon atom, $R^{13A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, particularly preferably a hydrogen atom, and the foregoing groups optionally have a substituent.

When Ring $L^{2A}$ is a pyridine ring, Ring $L^{2A}$ is preferably a pyridine ring in which $E^{21A}$ is a nitrogen atom, a pyridine ring in which $E^{22A}$ is a nitrogen atom or a pyridine ring in which $E^{23A}$ is a nitrogen atom, more preferably a pyridine ring in which $E^{22A}$ is a nitrogen atom.

When Ring $L^{2A}$ is a diazabenzene ring, Ring $L^{2A}$ is preferably a pyrimidine ring in which $E^{22A}$ and $E^{24A}$ are each a nitrogen atom or a pyrimidine ring in which $E^{22A}$ and $E^{24A}$ are each a nitrogen atom, more preferably a pyrimidine ring in which $E^{22A}$ and $E^{24A}$ are each a nitrogen atom.

Ring $L^{2A}$ is preferably a benzene ring.

$R^{21A}$, $R^{22A}$, $R^{23A}$ and $R^{24A}$ are each preferably a hydrogen atom, an alkyl group, a cycloalkyl group, an alkoxy group, a cycloalkoxy group, an aryl group, a monovalent heterocyclic group, a substituted amino group or a fluorine atom, more preferably a hydrogen atom, an alkyl group, a cycloalkyl group, an aryl group, a monovalent heterocyclic group, a substituted amino group or a fluorine atom, further preferably a hydrogen atom, an alkyl group, or a group represented by the formula (D-A), the formula (D-B) or the formula (D-C), particularly preferably a hydrogen atom or a group represented by the formula (D-A), especially preferably a hydrogen atom, and the foregoing groups optionally have a substituent.

When Ring $L^{2A}$ has an aryl group, a monovalent heterocyclic group or a substituted amino group, it is preferable that $R^{22A}$ or $R^{23A}$ is an aryl group, a monovalent heterocyclic group or a substituted amino group, it is more preferable that $R^{22A}$ is an aryl group, a monovalent heterocyclic group or a substituted amino group.

When Ring $L^{2A}$ has a fluorine atom, it is preferable that $R^{21A}$, $R^{22A}$ or $R^{23A}$ is a fluorine atom, it is more preferable that $R^{21A}$ or $R^{23A}$ is a fluorine atom.

It is preferable that $R^{11A}$ and $R^{12A}$, $R^{12A}$ and $R^{13A}$, $R^{14}$ and $R^{21A}$, $R^{21A}$ and $R^{22A}$, $R^{22A}$ and $R^{23A}$, and $R^{23A}$ and $R^{24A}$ are not each combined together to form a ring together with the atoms to which they are attached.

The phosphorescent compound represented by the formula (1-A) is preferably a phosphorescent compound represented by the formula (1-A4), since the light emitting device of the present invention is further excellent in external quantum efficiency.

[Phosphorescent Compound Represented by the Formula (1-B)]

When Ring $L^{1B}$ is a diazabenzene ring, Ring $L^{1B}$ is preferably a pyrimidine ring in which $E^{11B}$ is a nitrogen atom or a pyrimidine ring in which $E^{13B}$ is a nitrogen atom, more preferably a pyrimidine ring in which $E^{11B}$ is a nitrogen atom.

Ring $L^{13}$ is preferably a pyridine ring.

When Ring $L^{2B}$ is a pyridine ring, Ring $L^{2B}$ is preferably a pyridine ring in which $E^{21B}$ is a nitrogen atom, a pyridine ring in which $E^{223}$ is a nitrogen atom or a pyridine ring in which $E^{23B}$ is a nitrogen atom, more preferably a pyridine ring in which $E^{22B}$ is a nitrogen atom.

When Ring $L^{23}$ is a diazabenzene ring, Ring $L^{2B}$ is preferably a pyrimidine ring in which $E^{22B}$ and $E^{24B}$ are each a nitrogen atom or a pyrimidine ring in which $E^{21B}$ and $E^{23B}$ are each a nitrogen atom, more preferably a pyrimidine ring in which $E^{22B}$ and $E^{24B}$ are each a nitrogen atom.

Ring $L^{2B}$ is preferably a benzene ring.

The examples and preferable ranges of the aryl group, the monovalent heterocyclic group and the substituted amino group represented by $R^{11B}$, $R^{12B}$, $R^{13B}$, $R^{14B}$, $R^{21B}$, $R^{22B}$, $R^{23B}$ and $R^{24B}$ are the same as the examples and preferable ranges of the aryl group, the monovalent heterocyclic group and the substituted amino group as the substituent which Ring $L^1$ and Ring $L^2$ optionally have, respectively.

The examples and preferable ranges of the substituent which $R^{11B}$, $R^{12B}$, $R^{11B}$, $R^{14B}$, $R^{21B}$, $R^{22B}$, $R^{23B}$ and $R^{24B}$ optionally have are the same as the examples and preferable ranges of the substituent which the substituent which Ring $L^1$ and Ring $L^2$ optionally have optionally further has.

$R^{11B}$, $R^{12B}$, $R^{13B}$, $R^{14B}$, $R^{21B}$, $R^{22B}$, $R^{23B}$ and $R^{24B}$ are each preferably a hydrogen atom, an alkyl group, a cycloalkyl group, an alkoxy group, a cycloalkoxy group, an aryl group, a monovalent heterocyclic group, a substituted amino group or a fluorine atom, more preferably a hydrogen atom, an alkyl group, a cycloalkyl group, an aryl group, a monovalent heterocyclic group, a substituted amino group or a fluorine atom, further preferably a hydrogen atom, an alkyl group, a fluorine atom, or a group represented by the formula (D-A), the formula (D-B) or the formula (D-C), particularly preferably a hydrogen atom, a fluorine atom, or a group represented by the formula (D-A), and the foregoing groups optionally have a substituent.

When Ring $L^{1B}$ has an aryl group, a monovalent heterocyclic group or a substituted amino group, it is preferable that $R^{11B}$, $R^{12B}$ or $R^{13B}$ is an aryl group, a monovalent heterocyclic group or a substituted amino group, it is more preferable that $R^{12B}$ or $R^{13B}$ is an aryl group, a monovalent heterocyclic group or a substituted amino group, it is further preferable that $R^{13B}$ is an aryl group, a monovalent heterocyclic group or a substituted amino group.

When Ring $L^{2B}$ has an aryl group, a monovalent heterocyclic group or a substituted amino group, it is preferable that $R^{22B}$ or $R^{23B}$ is an aryl group, a monovalent heterocyclic group or a substituted amino group, it is more preferable that $R^{22B}$ is an aryl group, a monovalent heterocyclic group or a substituted amino group.

When Ring $L^{2B}$ has a fluorine atom, it is preferable that $R^{21B}$, $R^{22B}$ or $R^{23B}$ is a fluorine atom, it is more preferable that $R^{21B}$ or $R^{23B}$ is a fluorine atom, it is further preferable that $R^{21B}$ and $R^{23B}$ is a fluorine atom.

The phosphorescent compound represented by the formula (1-B) is preferably a phosphorescent compound represented by the formula (1-B1) to the formula (1-B5), more preferably a phosphorescent compound represented by the formula (1-B1) to the formula (1-B3), further preferably a phosphorescent compound represented by the formula (1-B1) or the formula (1-B2), since the light emitting device of the present invention is further excellent in external quantum efficiency.

The examples and preferable ranges of the aryl group, the monovalent heterocyclic group and the substituted amino group represented by $R^{15B}$, $R^{16B}$, $R^{17B}$ and $R^{18B}$ are the same as the examples and preferable ranges of the aryl group, the monovalent heterocyclic group and the substituted amino group as the substituent which Ring $L^1$ and Ring $L^2$ optionally have, respectively.

The examples and preferable ranges of the substituent which $R^{15B}$, $R^{16B}$, $R^{17B}$ and $R^{18B}$ optionally have are the same as the examples and preferable ranges of the substituent which the substituent which Ring $L^1$ and Ring $L^2$ optionally have optionally further has.

$R^{15B}$, $R^{16B}$, $R^{17B}$ and $R^{18B}$ are each preferably a hydrogen atom, an alkyl group, a cycloalkyl group, an alkoxy group, a cycloalkoxy group, a fluorine atom, an aryl group, a monovalent heterocyclic group or a substituted amino group, more preferably a hydrogen atom, an alkyl group, a cycloalkyl group, an aryl group, a monovalent heterocyclic group or a substituted amino group, further preferably a hydrogen atom, an alkyl group or a cycloalkyl group, particularly preferably a hydrogen atom, and the foregoing groups optionally have a substituent.

The phosphorescent compound includes, for example, phosphorescent compounds represented by the following formulae.

[Chemical Formula 53]

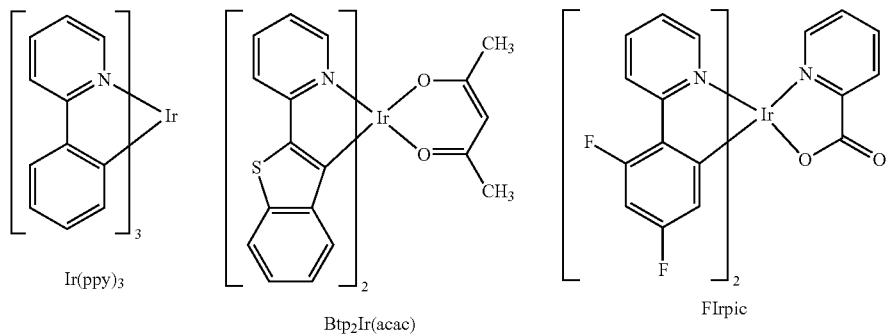

Ir(ppy)₃

Btp₂Ir(acac)

FIrpic

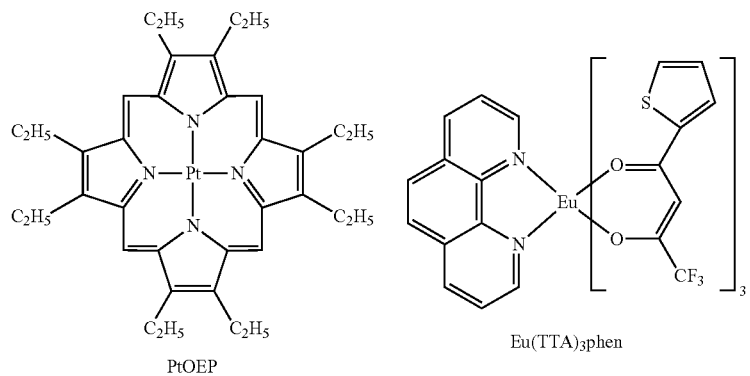

PtOEP

Eu(TTA)₃phen

[Chemical Formula 54]
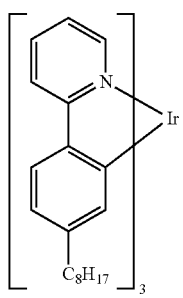
COM-1
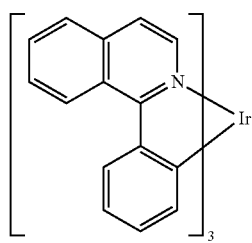
COM-2
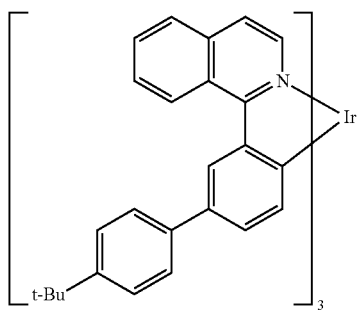
COM-3
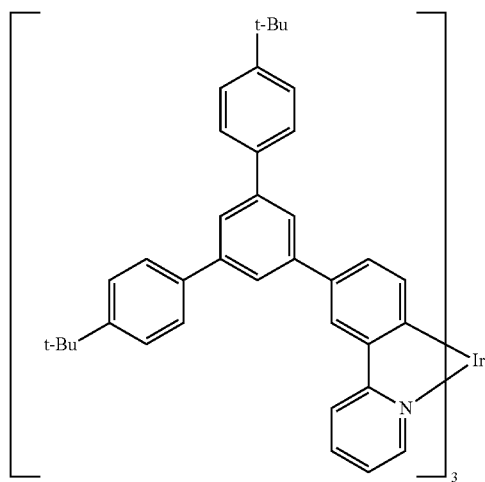
COM-4
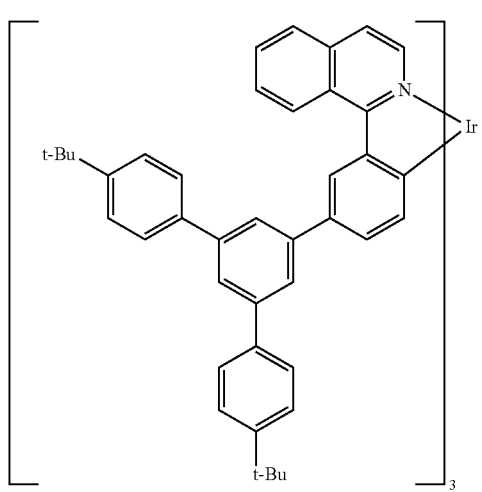
COM-5

[Chemical Formula 55]
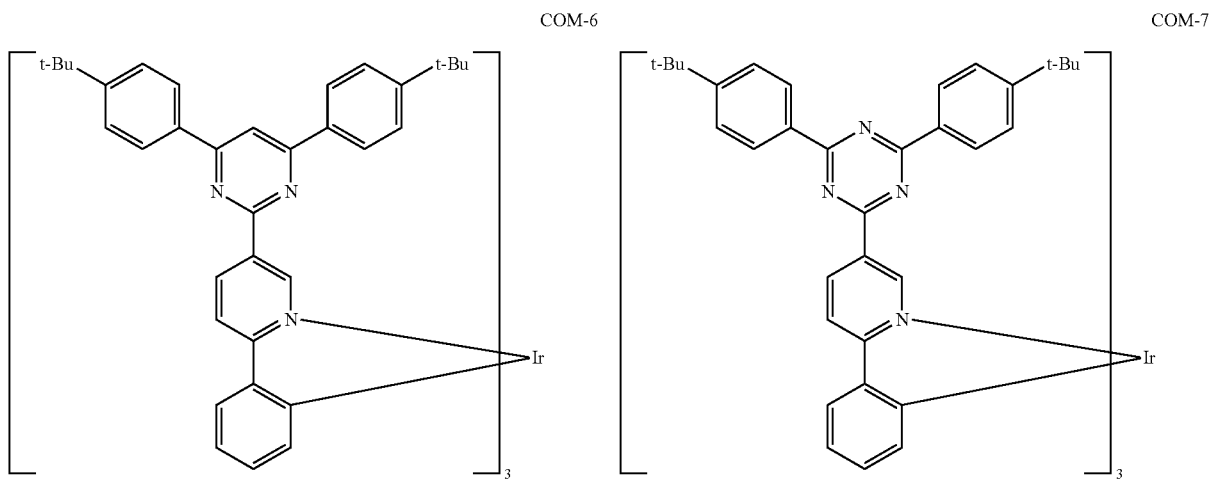
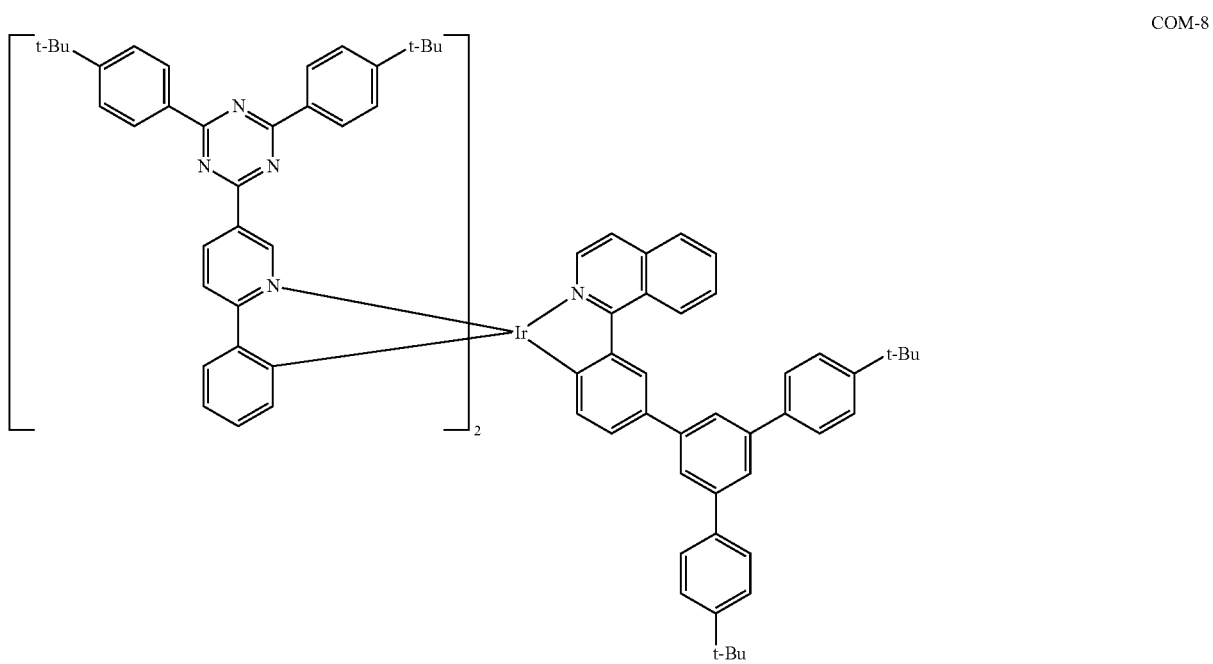
[Chemical Formula 56]
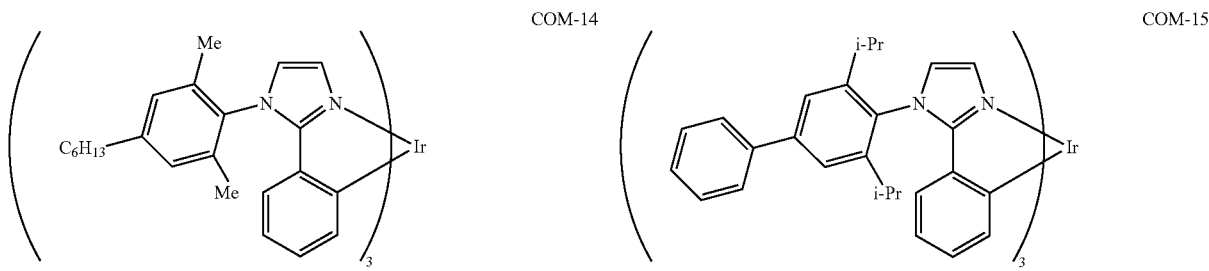

-continued
COM-16
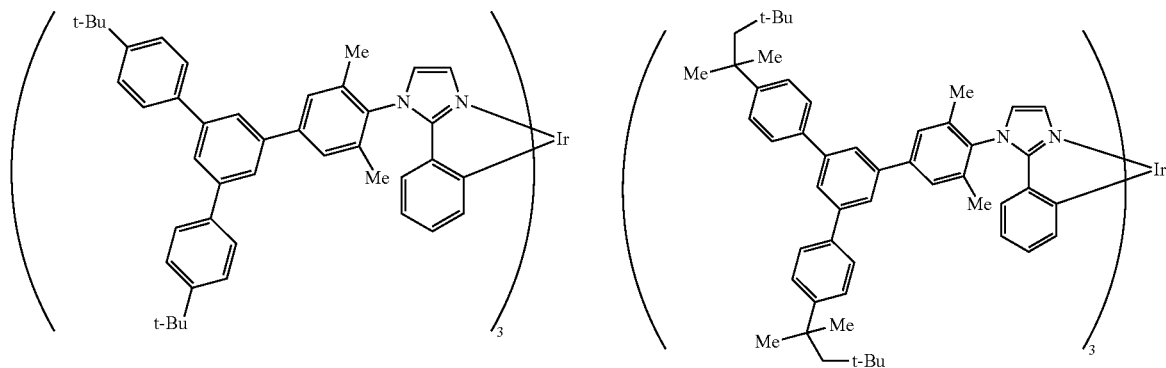
COM-17
COM-18
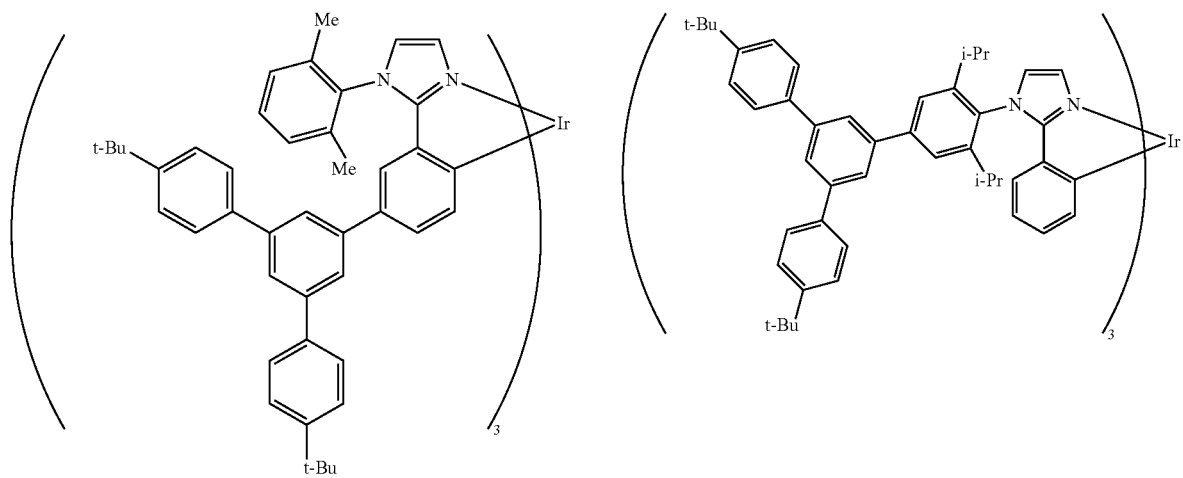
COM-19
COM-20
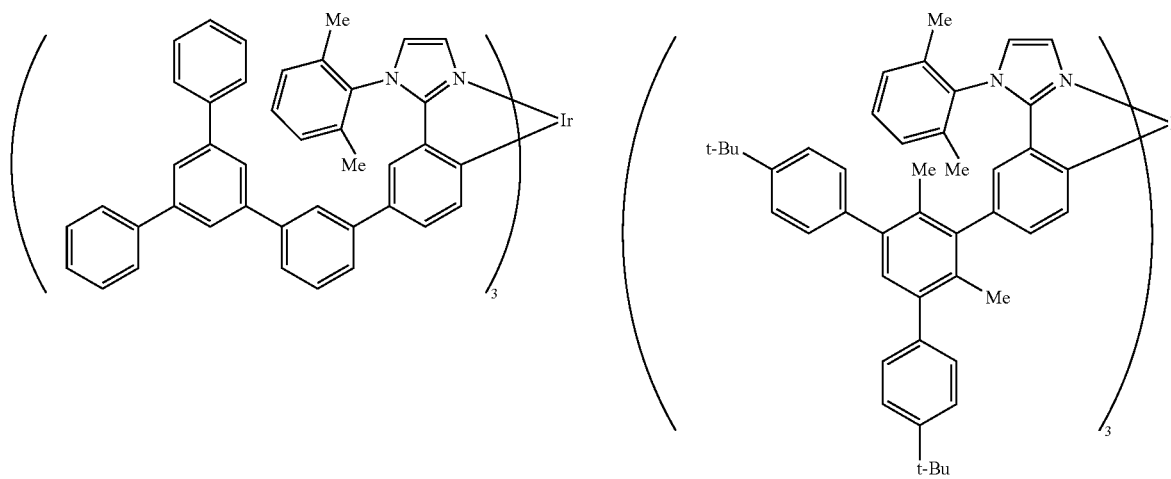
COM-21

[Chemical Formula 57]
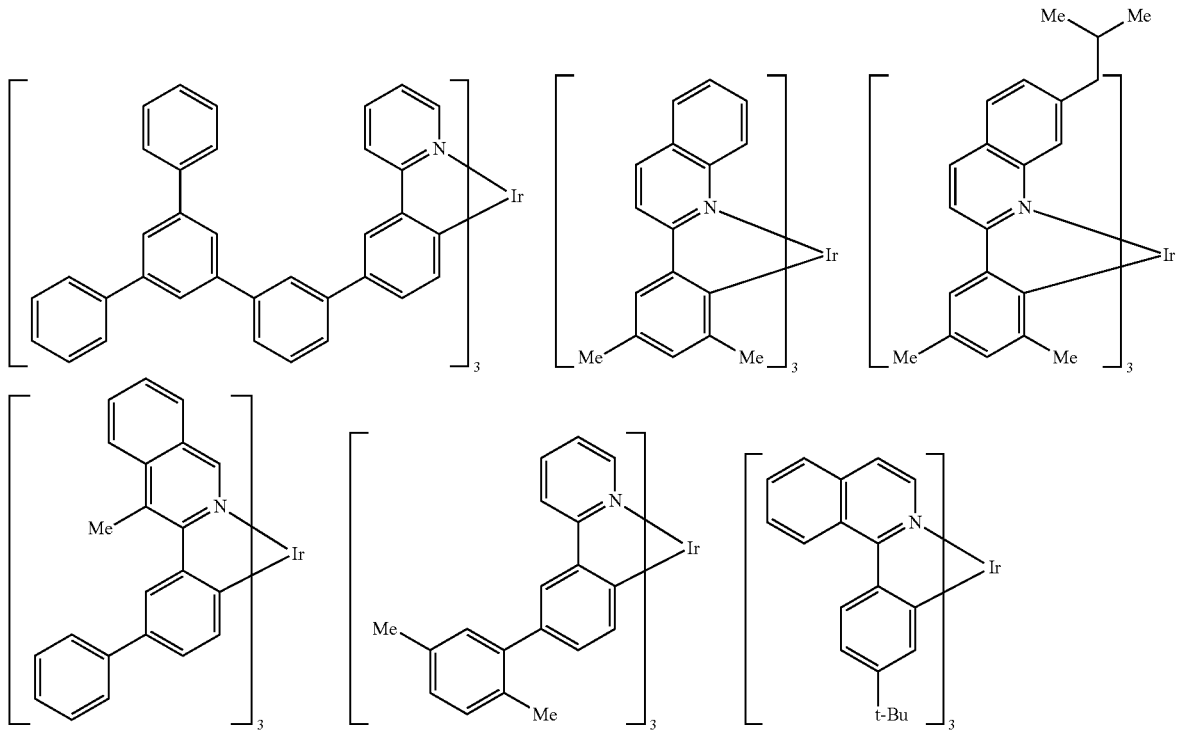
[Chemical Formula 58]
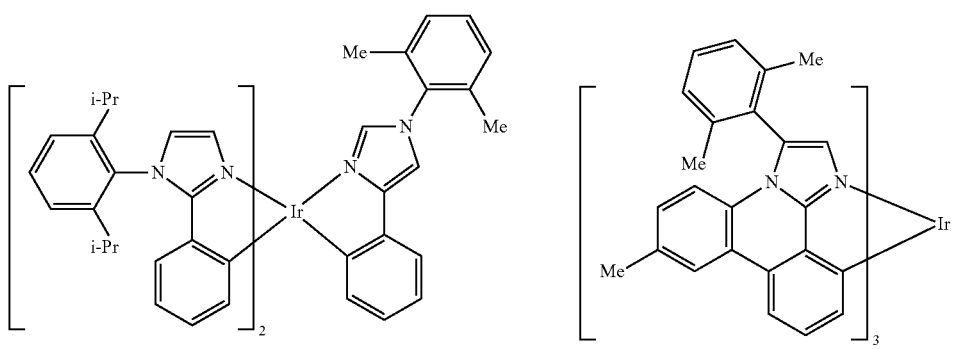
[Chemical Formula 59]
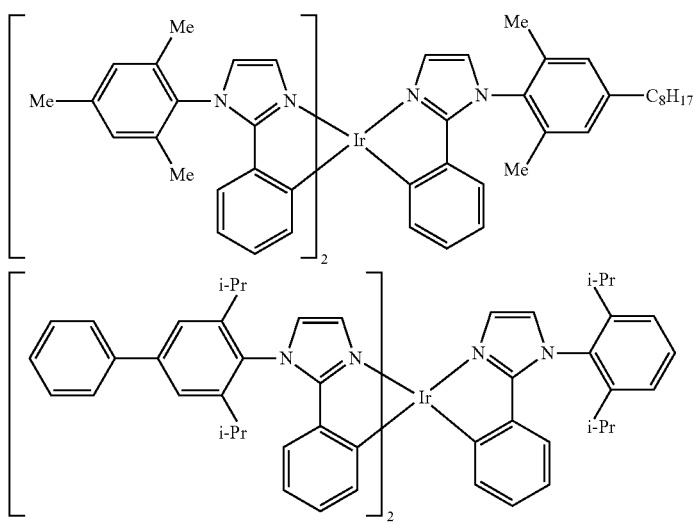

The phosphorescent compound is available from Aldrich, Luminescence Technology Corp., American Dye Source and the like.

Further, it is also possible to produce the phosphorescent compound by known methods described in Journal of the American Chemical Society, vol. 107, 1431-1432 (1985), Journal of the American Chemical Society, vol. 106, 6647-6653 (1984), International Publication WO 2011/024761, International Publication WO 2002/44189, JP-A No. 2006-188673 and the like.

In the composition of the present invention, the content of the phosphorescent compound is usually 0.01 to 99 parts by mass when the sum of two or more compounds represented by the formula (C-1) and the phosphorescent compound is taken as 100 parts by mass, and it is preferably 0.1 to 80 parts by mass, more preferably 1 to 60 parts by mass, further preferably 5 to 40 parts by mass, since the light emitting device of the present invention is more excellent in external quantum efficiency.

When the composition of the present invention contains two or more compounds represented by the formula (C-1) in which $R^C$ is a group represented by the formula (C'-1) (hereinafter, referred to as "compound (C-1-1)"), at least one out of the two or more compounds (C-1-1) is preferably a compound represented by the formula (C-2-1), more preferably a compound represented by the formula (C-3-1), since the light emitting device of the present invention is more excellent in external quantum efficiency.

When the composition of the present invention contains two or more compounds (C-1-1), at least two out of the two or more compounds (C-1-1) are each preferably a compound represented by the formula (C-2-1), more preferably a compound represented by the formula (C-3-1), since the light emitting device of the present invention is further excellent in external quantum efficiency.

When the composition of the present invention contains one or more compounds (C-1-1) and one or more compounds represented by the formula (C-1) in which $R^C$ is an oxygen atom or a sulfur atom (hereinafter, referred to as "compound (C-1-2)"), at least one out of the one or more compounds (C-1-1) is preferably a compound represented by the formula (C-2-1), more preferably a compound represented by the formula (C-3-1), since the light emitting device of the present invention is more excellent in external quantum efficiency.

When the composition of the present invention contains one or more compounds (C-1-1) and one or more compounds (C-1-2), at least one out of the one or more compounds (C-1-2) is preferably a compound represented by the formula (C-2-2), more preferably a compound represented by the formula (C-3-2), since the light emitting device of the present invention is more excellent in external quantum efficiency.

When the composition of the present invention contains one or more compounds (C-1-1) and one or more compounds (C-1-2), it is preferable that at least one out of the one or more compounds (C-1-1) is a compound represented by the formula (C-2-1) and at least one out of the one or more compounds (C-1-2) is a compound represented by the formula (C-2-2), it is more preferable that at least one out of the one or more compounds (C-1-1) is a compound represented by the formula (C-3-1) and at least one out of the one or more compounds (C-1-2) is a compound represented by the formula (C-3-2), since the light emitting device of the present invention is further excellent in external quantum efficiency.

The composition of the present invention preferably contains 2 to 10 kinds of compounds represented by the formula (C-1), more preferably contains 2 to 5 kinds of compounds represented by the formula (C-1), further preferably contains 2 or 3 kinds of compounds represented by the formula (C-1), particularly preferably contains 2 kinds of compounds represented by the formula (C-1), since the composition of the present invention can be produced easily.

In the composition of the present invention, the content of at least one compound (C-1-1) is usually 1 to 99 parts by mass when the total content of two or more compounds represented by the formula (C-1) (that is, the total content of the compound represented by the formula (C-1) contained in the composition of the present invention, the same shall apply hereinafter) is taken as 100 parts by mass, and it is preferably 10 to 90 parts by mass, more preferably 25 to 75 parts by mass, further preferably 40 to 60 parts by mass, since the light emitting device of the present invention is more excellent in external quantum efficiency.

When the composition of the present invention contains two or more compounds (C-1-1), the total content of the two or more compounds (C-1-1) is usually 1 to 100 parts by mass when the total content of two or more compounds represented by the formula (C-1) is taken as 100 parts by mass, and it is preferably 25 to 100 parts by mass, more preferably 50 to 100 parts by mass, further preferably 75 to 100 parts by mass, particularly preferably 95 to 100 parts by mass, since the light emitting device of the present invention is more excellent in external quantum efficiency.

When the composition of the present invention contains one or more compounds (C-1-1) and one or more compounds (C-1-2), the total content of the one or more compounds (C-1-1) is usually 1 to 99 parts by mass when the total content of two or more compounds represented by the formula (C-1) is taken as 100 parts by mass, and it is preferably 10 to 90 parts by mass, more preferably 25 to 75 parts by mass, further preferably 40 to 60 parts by mass, since the light emitting device of the present invention is more excellent in external quantum efficiency.

[Other components] The composition of the present invention may further contain at least one material selected from the group consisting of a hole transporting material, a hole injection material, an electron transporting material, an electron injection material, a light emitting material, an antioxidant and a solvent. However, the hole transporting material, the hole injection material, the electron transporting material and the electron injection material are different from the compound represented by the formula (C-1), and the light emitting material is different from the compound represented by the formula (C-1) and the phosphorescent compound.

[Ink] The composition (hereinafter, referred to as "ink") containing two or more compounds represented by the formula (C-1), a phosphorescent compound and a solvent is suitable for fabrication of a light emitting device using a printing method such as an ink jet print method, a nozzle print method and the like. The viscosity of the ink may be adjusted according to the type of the printing method, and it is preferably 1 to 20 mPa·s at 25° C.

The solvent contained in the ink is preferably a solvent that can dissolve or uniformly disperse the solid content in the ink. The solvent includes, for example, chlorine-based solvents, ether-based solvents, aromatic hydrocarbon-based solvents, aliphatic hydrocarbon-based solvents, ketone-based solvents, ester-based solvents, poly-hydric alcohol-based solvents, alcohol-based solvents, sulfoxide-based solvents and amide-based solvents.

In the ink, the compounding amount of the solvent is usually 1000 to 100000 parts by mass, when the sum of two or more compounds represented by the formula (C-1) and the phosphorescent compound is taken as 100 parts by mass.

The solvents may be used each singly or in combination of two or more.

[Hole transporting material] The hole transporting materials are classified into low molecular compounds and polymer compounds, and preferable are polymer compounds having a crosslinkable group.

The polymer compound includes, for example, polyvinylcarbazole, and derivatives thereof; polyarylenes having an aromatic amine structure in the side chain or main chain, and derivatives thereof. The polymer compound may also be a compound to which an electron accepting site is bound, such as fullerene, tetrafluorotetracyanoquinodimethane, tetracyanoethylene, trinitrofluorenone and the like.

In the composition of the present invention, the compounding amount of the hole transporting material is usually 1 to 400 parts by mass, when the sum of two or more compounds represented by the formula (C-1) and the phosphorescent compound is taken as 100 parts by mass.

The hole transporting materials may be used each singly or in combination two or more.

[Electron Transporting Material]

The electron transporting material is classified into low molecular compounds and polymer compounds. The electron transporting material may have a crosslinkable group.

The low molecular compound includes, for example, metal complexes having 8-hydroxyquinoline as a ligand; oxadiazole, anthraquinodimethane, benzoquinone, naphthoquinone, anthraquinone, tetracyanoanthraquinodimethane, fluorenone, diphenyldicyanoethylene and diphenoquinone, and derivatives thereof.

The polymer compound includes, for example, polyphenylene, polyfluorene, and derivatives thereof. The polymer compound may be doped with a metal.

In the composition of the present invention, the compounding amount of the electron transporting material is usually 1 to 400 parts by mass, when the sum of two or more compounds represented by the formula (C-1) and the phosphorescent compound is taken as 100 parts by mass.

The electron transporting materials may be used each singly or in combination of two or more.

[Hole Injection Material and Electron Injection Material]

The hole injection material and the electron injection material are each classified into low molecular compounds and polymer compounds. The hole injection material and the electron injection material optionally have a crosslinkable group.

The low molecular compound includes, for example, metal phthalocyanines such as copper phthalocyanine and the like; carbon; oxides of metals such as molybdenum, tungsten and the like; and metal fluorides such as lithium fluoride, sodium fluoride, cesium fluoride, potassium fluoride and the like.

The polymer compound includes electrically conductive polymers such as, for example, polyaniline, polythiophene, polypyrrole, polyphenylenevinylene, polythienylenevinylene, polyquinoline and polyquinoxaline, and derivatives thereof; polymers containing an aromatic amine structure in the main chain or side chain, and the like.

In the composition of the present invention, the compounding amounts of the hole injection material and the electron injection material are each usually 1 to 400 parts by mass, when the sum of two or more compounds represented by the formula (C-1) and the phosphorescent compound is taken as 100 parts by mass. The hole injection materials and the electron injection materials each may be used singly or in combination of two or more.

[Ion Doping]

When the hole injection material or the electron injection material contains an electrically conductive polymer, the electric conductivity of the electrically conductive polymer is preferably $1 \times 10^{-5}$ S/cm to $1 \times 10^3$ S/cm. For adjusting the electric conductivity of the electrically conductive polymer within such a range, the electrically conductive polymer can be doped with an appropriate amount of ions. The kind of the ion to be doped is an anion for the hole injection material and a cation for the electron injection material. The anion includes, for example, a polystyrenesulfonate ion, an alkylbenzenesulfonate ion and a camphor sulfonate ion. The cation includes, for example, a lithium ion, a sodium ion, a potassium ion and a tetrabutylammonium ion.

The ions to be doped may be used each singly or in combination of two or more.

[Light Emitting Material]

The light emitting material is classified into low molecular compounds and polymer compounds. The light emitting material optionally has a substituent.

The low molecular compound includes, for example, naphthalene and derivatives thereof, anthracene and derivatives thereof, and, perylene and derivatives thereof.

The polymer compound includes, for example, arylene groups such as a phenylene group, a naphthalenediyl group, a fluorenediyl group, a phenanthrenediyl group, a dihydrophenanthrenediyl group, an anthracenediyl group and a pyrenediyl group and the like; aromatic amine residues such as a group obtained by removing two hydrogen atoms from an aromatic amine, and the like; and polymer compounds containing a divalent heterocyclic group such as a carbazolediyl group, a phenoxazinediyl group and a phenothiazinediyl group and the like.

In the composition of the present invention, the content of the light emitting material is usually 0.1 to 400 parts by mass when the sum of the two or more compounds represented by the formula (C-1) and the phosphorescent compound is taken as 100 parts by mass.

The light emitting materials may be used each singly or in combination of two or more.

[Antioxidant]

The antioxidant may be a compound which is soluble in the same solvent as for the compound represented by the formula (C-1) and the phosphorescent compound and which does not disturb light emission and charge transportation, and includes, for example, phenol-based antioxidants and phosphorus-based antioxidants.

In the composition of the present invention, the compounding amount of the antioxidant is usually 0.001 to 10 parts by mass, when the sum of two or more compounds represented by the formula (C-1) and the phosphorescent compound is taken as 100 parts by mass.

The antioxidants may be used each singly or in combination of two or more.

<Film>

The film contains the composition of the present invention.

The film is suitable as a light emitting layer in a light emitting device.

The film can be fabricated by, for example, a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an ink jet printing method, a capillary coat method or a nozzle coat method, using an ink.

The thickness of the film is usually 1 nm to 10 μm.

<Light Emitting Device>

The light emitting device of the present invention is a light emitting device containing the composition of the present invention.

The constitution of the light emitting device of the present invention includes, for example, electrodes consisting of an anode and a cathode, and a layer containing the composition of the present invention disposed between the electrodes.

[Layer Constitution]

The layer containing the composition of the present invention is usually at least one layer selected from the group consisting of a light emitting layer, a hole transporting layer, a hole injection layer, an electron transporting layer and an electron injection layer, and is preferably a light emitting layer. These layers contain a light emitting material, a hole transporting material, a hole injection material, an electron transporting material and an electron injection material, respectively. These layers can be formed by dissolving a light emitting material, a hole transporting material, a hole injection material, an electron transporting material and an electron injection material in the solvent described above to prepare an ink and by using the same method as for fabrication of the film described above, using the prepared ink.

The light emitting device has a light emitting layer between an anode and a cathode. The light emitting device of the present invention preferably has at least one of a hole injection layer and a hole transporting layer between an anode and a light emitting layer from the standpoint of hole injectability and hole transportability, and preferably has at least one of an electron injection layer and an electron transporting layer between a cathode and a light emitting layer from the standpoint of electron injectability and electron transportability.

As the materials of the hole transporting layer, the electron transporting layer, the light emitting layer, the hole injection layer and the electron injection layer, hole transporting materials, electron transporting materials, light emitting materials, hole injection materials and electron injection materials described above and the like are mentioned, respectively, in addition to the materials in the composition of the present invention.

When the material of the hole transporting layer, the material of the electron transporting layer and the material of the light emitting layer are dissolved in a solvent used in forming a layer adjacent to the hole transporting layer, the electron transporting layer and the light emitting layer in fabrication of a light emitting device, it is preferable that the materials have a crosslinkable group to avoid dissolving of the materials in the solvent. After forming each layer using the material having a crosslinkable group, the crosslinkable group can be cross-linked to insolubilize the layer.

The method for forming each of the first light emitting layer, the second light emitting layer, the hole transporting layer, the electron transporting layer, the hole injection layer, the electron injection layer and the like in the light emitting device of the present invention includes, when a low molecular compound is used, for example, a method of vacuum vapor deposition from a powder and a method of forming a film from a solution or melted state, and when a polymer compound is used, for example, a method of forming a film from a solution or melted state.

The order, the number and the thickness of layers to be laminated may be adjusted in consideration of the external quantum efficiency and luminance life.

[Substrate/Electrode]

The substrate in the light emitting device may advantageously be a substrate on which an electrode can be formed and which does not change chemically in forming an organic layer, and is, for example, a substrate made of a material such as glass, plastic, silicon and the like. When an opaque substrate is used, it is preferable that the electrode farthest from the substrate is transparent or semi-transparent.

The material of the anode includes, for example, electrically conductive metal oxides and semi-transparent metals, preferably includes indium oxide, zinc oxide, tin oxide; electrically conductive compounds such as indium-tin-oxide (ITO), indium-zinc-oxide and the like; argentine-palladium-copper (APC) complex; NESA, gold, platinum, silver and copper.

The material of the cathode includes, for example, metals such as lithium, sodium, potassium, rubidium, cesium, beryllium, magnesium, calcium, strontium, barium, aluminum, zinc, indium and the like; alloys composed of two or more of them; alloys composed of at least one of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each have a laminated structure of two or more layers.

[Application]

In order to obtain planar light emission using a light emitting device, the planar anode and the planar cathode may be arranged so as to overlap each other. In order to obtain patterned light emission, there are a method of installing a mask having a patterned window on the surface of a planar light emitting device, a method in which a layer to be formed as a non-light emitting part is formed extremely thick so as to cause substantially non light emission and a method of forming an anode or a cathode, or both electrodes in a pattern. A segment type display capable of displaying numerals, letters and the like can be obtained by forming a pattern by any one of these methods and disposing several electrodes so that several electrodes can be turned on and off independently. In order to obtain a dot matrix display, both the anode and the cathode may be formed in a stripe shape and arranged so as to be orthogonal to each other. Partial color display and multicolor display become possible by a method of separately coating plural kinds of polymer compounds having different emission colors or a method using a color filter or a fluorescence conversion filter. The dot matrix display can be driven passively or can be driven actively in combination with a TFT and the like. These displays can be used for displays of computers, televisions, portable terminals, and the like. The planar light emitting device can be suitably used as a planar light source for backlight of a liquid crystal display, or as a planar light source for illumination. If a flexible substrate is used, it can be used as a curved light source and a curved display.

EXAMPLES

The present invention will be illustrated further in detail by examples below, but the present invention is not limited to these examples.

In examples, the polystyrene-equivalent number-average molecular weight (Mn) and the polystyrene-equivalent weight-average molecular weight (Mw) of polymer compounds were determined by the following size exclusion chromatography (SEC) using tetrahydrofuran as a mobile phase.

A polymer compound to be measured was dissolved in tetrahydrofuran at a concentration of about 0.05% by mass, and 10 μL of the solution was injected into SEC. The mobile phase was flowed at a flow rate of 1.0 mL/min. As a column, PLgel MIXED-B (manufactured by Polymer Laboratories Ltd.) was used. As a detector, a UV-VIS detector (trade name: UV-8320GPC manufactured by Tosoh Corp.) was used.

NMR was measured by the following method.

Five to ten mg of a measurement sample was dissolved in about 0.5 mL of deuterated chloroform ($CDCl_3$), deuterated tetrahydrofuran, deuterated dimethyl sulfoxide, deuterated acetone, deuterated N,N-dimethylformamide, deuterated toluene, deuterated methanol, deuterated ethanol, deuterated 2-propanol or deuterated methylene chloride, and NMR thereof was measured using an NMR apparatus (trade name: JNM-ECZ400S/L1 manufactured by JEOL RESONANCE).

As an indicator of the purity of the compound, high performance liquid chromatography (HPLC) area percentage value was used. This value is a value by HPLC (trade name: LC-20A manufactured by Shimadzu Corp.) at UV=254 nm unless otherwise stated. In this operation, the compound to be measured was dissolved in tetrahydrofuran or chloroform so as to give a concentration of 0.01 to 0.2% by mass, and 1 to 10 μL of the solution was poured into HPLC depending on the concentration. As a mobile phase of HPLC, acetonitrile/tetrahydrofuran were used while changing the ratio thereof from 100/0 to 0/100 (volume ratio), and flowed at a flow rate of 1.0 mL/min. As a column, SUMIPAX ODS Z-CLUE (manufactured by Sumika Chemical Analysis Service, Ltd., internal diameter: 4.6 mm, length: 250 mm, particle size: 3 μm) or an ODS column having the equivalent performance was used. As a detector, a photodiode array detector (trade name: SPD-M20A manufactured by Shimadzu Corp.) was used.

<Synthesis Example M1> Synthesis of Compounds M1 to M9

Compounds M1, M2 and M3 were synthesized according to the method described in International Publication WO 2013/146806.

A compound M4 was synthesized according to the method described in JP-A No. 2012-33845.

A compound M5 was synthesized according to the method described in JP-A No. 2010-189630.

A compound M6 was synthesized according to the method described in JP-A No. 2011-174062.

A compound M7 was synthesized according to the method described in International Publication WO 2002/045184.

A compound M8 was synthesized according to the method described in International Publication WO 2005/049546.

A compound M9 was synthesized according to the method described in JP-A No. 2008-106241.

[Chemical Formula 60]

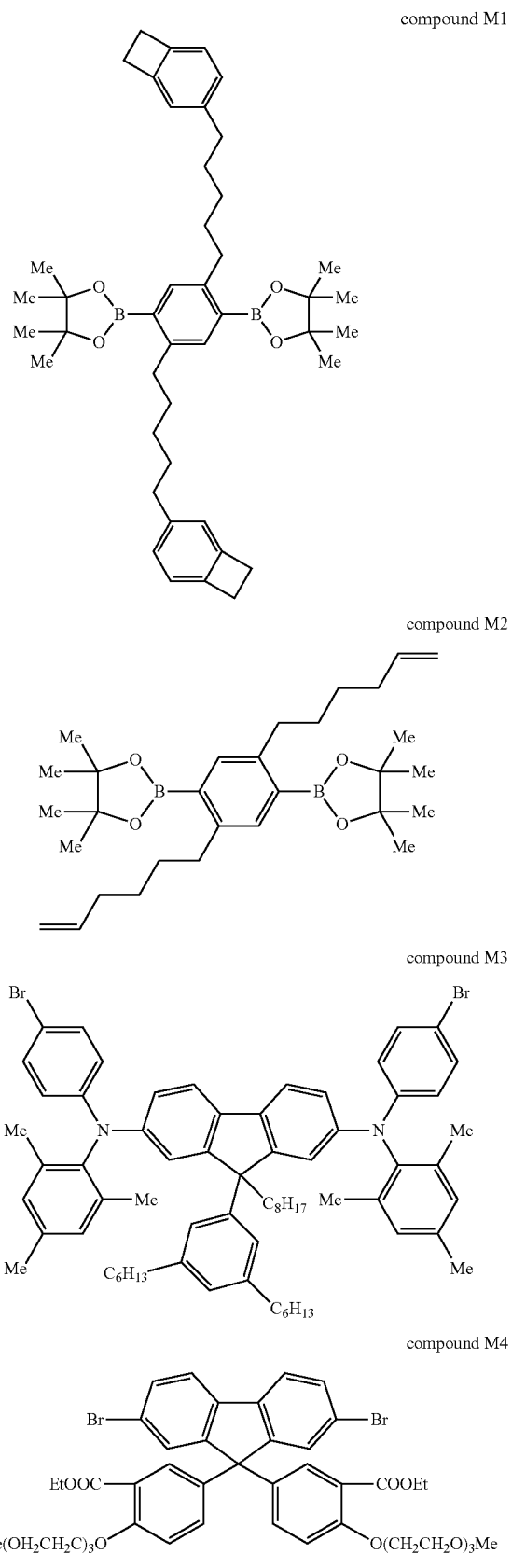

compound M5

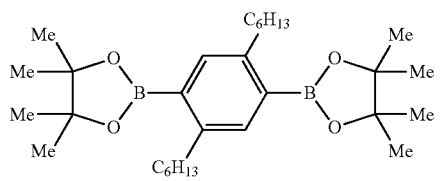

[Chemical Formula 61]

compound M6

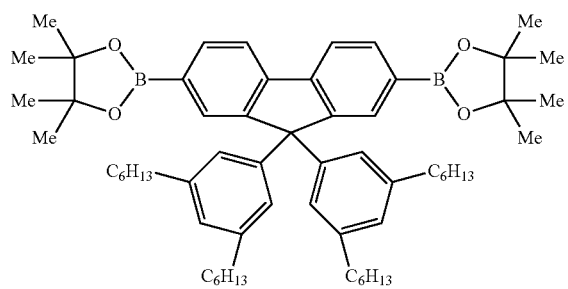

compound M7

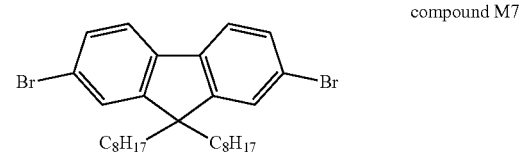

compound M8

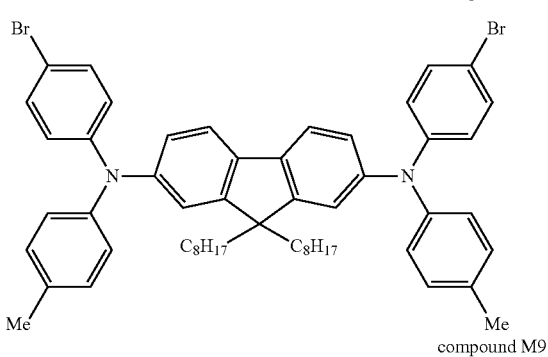

compound M9

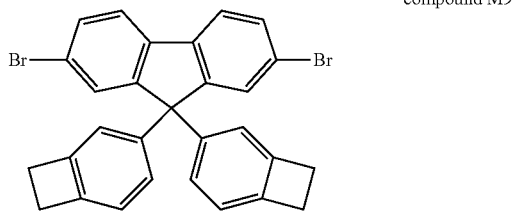

<Synthesis Example HTL1> Synthesis of Polymer Compound HTL-1

An inert gas atmosphere was prepared in a reaction vessel, then, the compound M1 (0.800 g), the compound M2 (0.149 g), the compound M3 (1.66 g), dichlorobis(tris-o-methoxyphenylphosphine)palladium (1.4 mg) and toluene (45 mL) were added, and the mixture was heated at 100° C. Thereafter, into this was dropped a 20% by mass tetraethylammonium hydroxide aqueous solution (16 mL), and the mixture was refluxed for 7 hours. Thereafter, to this were added 2-ethylphenylboronic acid (90 mg) and dichlorobis(tris-o-methoxyphenylphosphine)palladium (1.3 mg), and the mixture was refluxed for 17.5 hours. Thereafter, to this was added a sodium diethyldithiacarbamate aqueous solution, and the mixture was stirred at 85° C. for 2 hours. The resultant reaction liquid was cooled, then, washed with 3.6% by mass hydrochloric acid, 2.5% by mass ammonia water and water, respectively. The resultant solution was dropped into methanol, to generate a precipitate. The resultant precipitate was dissolved in toluene, and purified by passing through an alumina column and a silica gel column in this order. The resultant solution was dropped into methanol, and the mixture was stirred, then, the resultant precipitate was collected by filtration, and dried, to obtain 1.64 g of a polymer compound HTL-1. The polymer compound HTL-1 had an Mn of $3.5 \times 10^4$ and an Mw of $2.2 \times 10^5$.

The polymer compound HTL-1 is a copolymer constituted of a constitutional unit derived from the compound M1, a constitutional unit derived from the compound M2 and a constitutional unit derived from the compound M3 at a molar ratio of 40:10:50, according to the theoretical values calculated from the amounts of the charged raw materials.

<Synthesis Example HTL2> Synthesis of Polymer Compound HTL-2

A polymer compound HTL-2 was synthesized according to the method described in JP-A No. 2012-144722 using the compound M6, the compound M7, the compound M8 and the compound M9. The polymer compound HTL-2 had an Mn of $7.8 \times 10^4$ and an Mw of $2.6 \times 10^5$.

The polymer compound HTL-2 is a copolymer constituted of a constitutional unit derived from the compound M6, a constitutional unit derived from the compound M7, a constitutional unit derived from the compound M8 and a constitutional unit derived from the compound M9 at a molar ratio of 50:12.5:30:7.5, according to the theoretical values calculated from the amounts of the charged raw materials.

<Synthesis Example B1> Synthesis and Acquisition of Phosphorescent Compounds B1 and B2

A phosphorescent compound B1 (FIrpic) was purchased from Aldrich.

A phosphorescent compound B2 was synthesized based on the method described in International Publication WO 2006/121811 and JP-A No. 2013-048190.

[Chemical Formula 62]

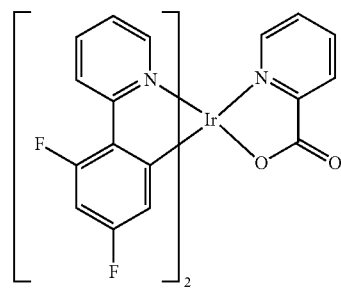

phosphorescent compound B1

-continued

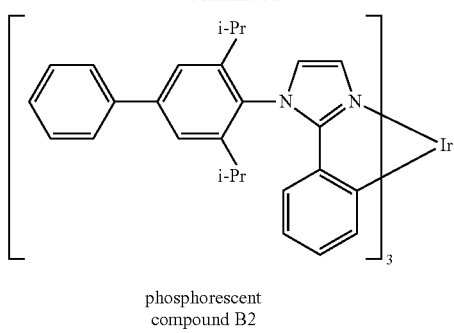

phosphorescent
compound B2

<Synthesis Example G1> Synthesis of
Phosphorescent Compounds G1 and G2

A phosphorescent compound G1 was synthesized based on the method described in International Publication WO 2011/032626.

A phosphorescent compound G2 was synthesized according to the method described in International Publication WO 2009/131255.

[Chemical Formula 63]

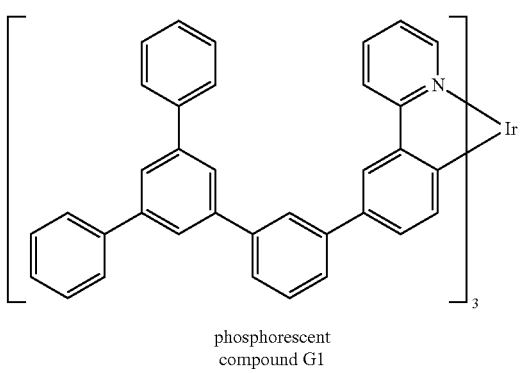

phosphorescent
compound G1

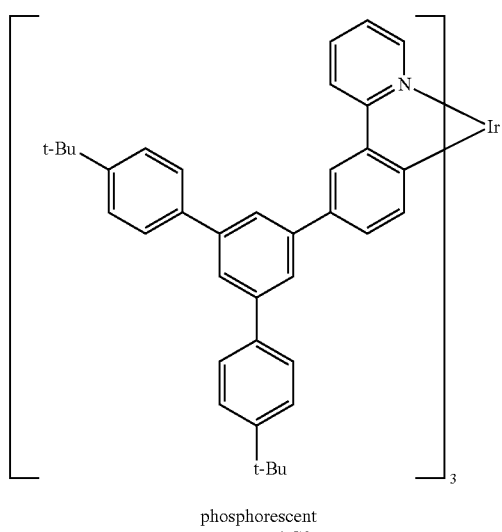

phosphorescent
compound G2

<Synthesis Example R1> Synthesis of
Phosphorescent Compound R1

A phosphorescent compound R1 was synthesized based on the method described in JP-A No. 2006-188673.

[Chemical Formula 64]

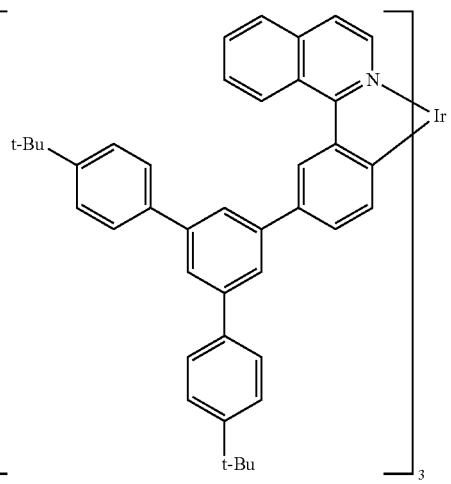

phosphorescent compound R1

<Synthesis Example H1> Synthesis and Acquisition
of Compounds HM-1, HM-5 to HM7, HM-10 to
HM-12 and HM-14 to HM-17

A compound HM-1, a compound HM-6 and a compound HM-7 were purchased from Luminescence Technology Corp.

A compound HM-5 was synthesized based on the method described in, International Publication WO 2010/015306.

A compound HM-10 and a compound HM-12 was synthesized based on the method described in International Publication WO 2012/048820.

A compound HM-11 was synthesized based on the method described in International Publication WO 2014/023388.

A compound HM-14 was synthesized according to the method described in International Publication WO 2016/194695.

A compound HM-15 was synthesized based on the method described in International Publication WO 2013/045411.

A compound HM-16 was purchased from 1-Material.

A compound HM-17 was synthesized based on the method described in International Publication WO 2013/045410.

[Chemical Formula 65]
low molecular compound HM-1
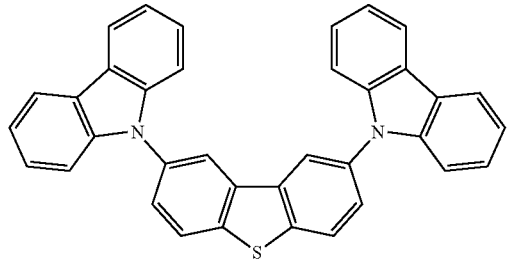
low molecular compound HM-5
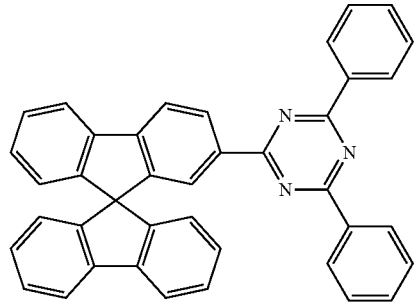
low molecular compound HM-6
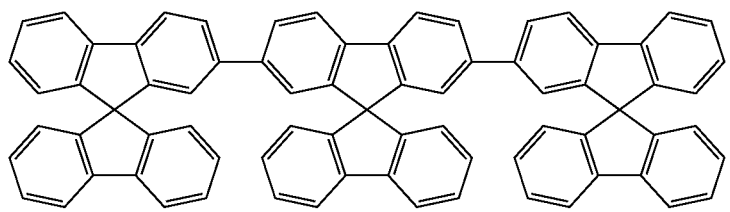
[Chemical Formula 66]
compound HM-7
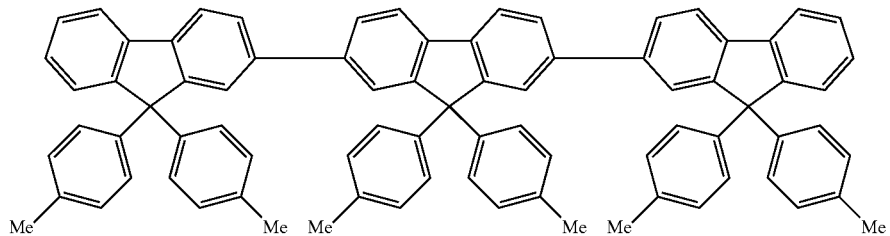
compound HM-10
compound HM-11
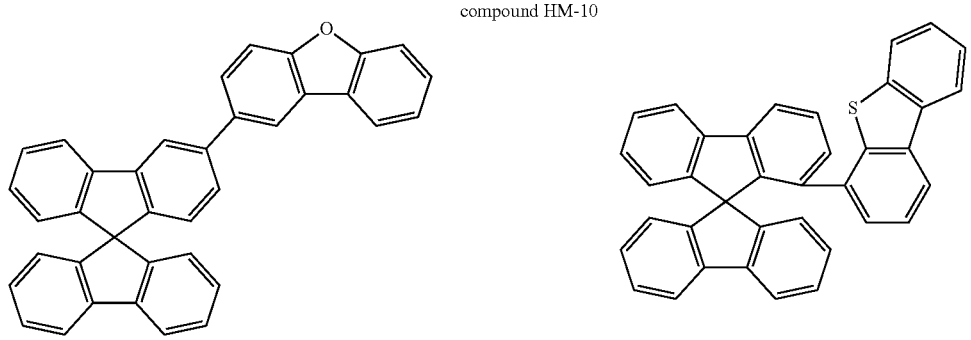
[Chemical Formula 67]
compound HM-12
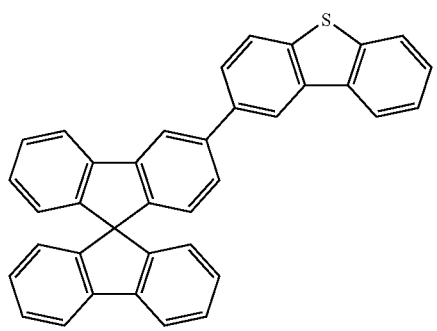
compound HM-14
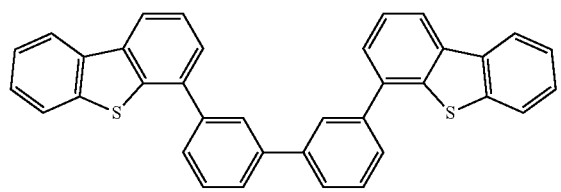

compound HM-15

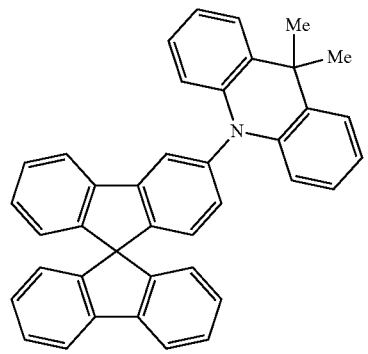

compound HM-16 compound HM-17

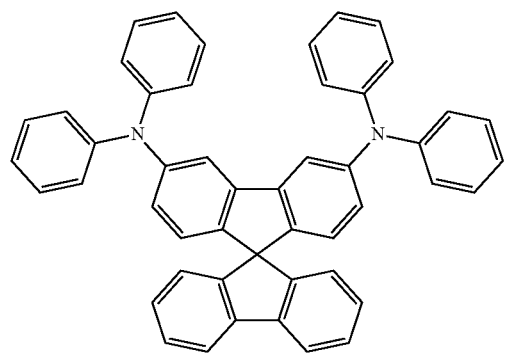

<Synthesis Example HM-2> Synthesis of Compound HM-2

[Chemical Formula 69]

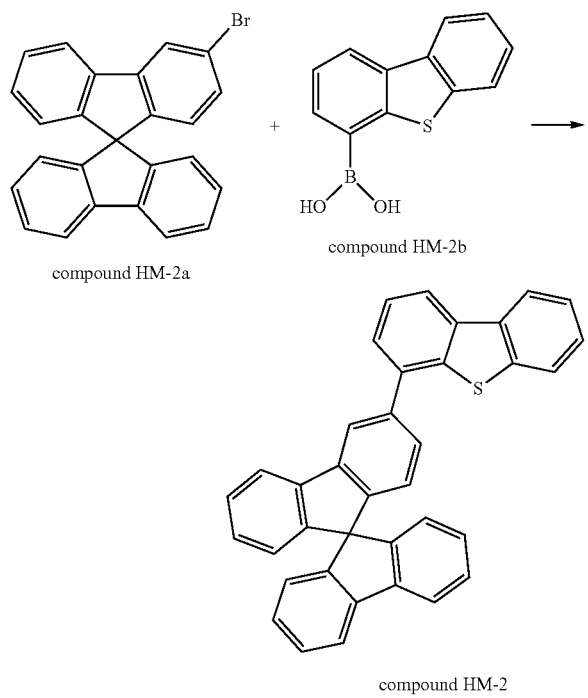

A nitrogen gas atmosphere was prepared in a reaction vessel, then, a compound HM-2a (15.6 g), a compound HM-2b (10.3 g), toluene (390 mL), tetrakis(triphenylphosphine)palladium(0) (2.2 g) and a 20% by mass tetrabutylammonium hydroxide aqueous solution (194 g) were added, and the mixture was stirred at 90° C. for 4 hours. The resultant reaction liquid was cooled down to room temperature, then, filtrated through a filter paved with Celite. The resultant filtrate was washed with ion exchanged water, then, the resultant organic layer was dried over anhydrous sodium sulfate, and filtrated. The resultant filtrate was concentrated under reduced pressure, to obtain a solid. The resultant solid was crystallized using a mixed solvent of toluene and 2-propanol, then, dried at 50° C. under reduced pressure, to obtain a compound HM-2 (15.2 g). The HPLC area percentage value of the compound HM-2 was 99.5% or more.

The analysis result of the compound HM-2 was as described below.

$^1$H-NMR (CD$_2$Cl$_2$, 400 MHz): δ (ppm)=6.70-6.83 (4H, m), 7.15 (3H, t), 7.39 (3H, t), 7.48 (3H, t), 7.59 (2H, t), 7.83-7.93 (4H, m), 8.18-8.23 (3H, m).

\<Synthesis Example HM-3\> Synthesis of Compound HM-3

[Chemical Formula 70]

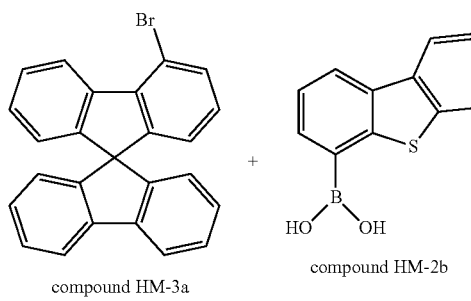

A nitrogen gas atmosphere was prepared in a reaction vessel, then, a compound HM-3a (13.5 g), a compound HM-2b (8.9 g), toluene (404 mL), tetrakis(triphenylphosphine)palladium(0) (2.0 g) and a 20% by mass tetrabutylammonium hydroxide aqueous solution (166 g) were added, and the mixture was stirred at 90° C. for 3 hours. The resultant reaction liquid was cooled down to room temperature, then, filtrated through a filter paved with Celite. The resultant filtrate was washed with ion exchanged water, then, the resultant organic layer was dried over anhydrous sodium sulfate, and filtrated. The resultant filtrate was concentrated under reduced pressure, to obtain a solid. The resultant solid was purified by silica gel column chromatography (using a mixed solvent of hexane and chloroform), and further, crystallized using a mixed solvent of toluene and methanol, then, dried at 50° C. under reduced pressure, to obtain a compound HM-3 (10.5 g). The HPLC area percentage value of the compound HM-3 was 99.5% or more.

The analysis result of the compound HM-3 was as described below.

$^1$H-NMR (CD$_2$Cl$_2$, 400 MHz): δ (ppm)=6.51 (1H, d), 6.60 (1H, d), 6.80 (4H, m), 6.92 (1H, t), 7.21 (3H, m), 7.34 (1H, d), 7.39-7.50 (4H, m), 7.65 (1H, d), 7.71 (1H, t), 7.81 (1H, d), 7.88 (2H, d), 8.28-8.35 (2H, m).

\<Synthesis Example HM-4\> Synthesis of Compound HM-4

[Chemical Formula 71]

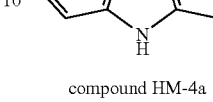

compound HM-4a

compound HM-4b

compound HM-4

A nitrogen gas atmosphere was prepared in a reaction vessel, then, a compound HM-4a (1.6 g), a compound HM-4b (1.3 g), xylene (63 mL), palladium(II) acetate (22 mg), tri-tert-butylphosphonium tetrafluoroborate (63 mg) and sodium tert-butoxide (1.9 g) were added, and the mixture was stirred for 54 hours under reflux with heat. The resultant reaction liquid was cooled down to room temperature, then, filtrated through a filter paved with silica gel and Celite. The resultant filtrate was washed with ion exchanged water, then, the resultant organic layer was dried over anhydrous sodium sulfate, and filtrated. The resultant filtrate was concentrated under reduced pressure, to obtain a solid. The resultant solid was purified by silica gel column chromatography (using a mixed solvent of hexane and chloroform), and further, crystallized using a mixed solvent of chloroform and 2-propanol, then, dried at 50° C. under reduced pressure, to obtain a compound HM-4 (1.0 g). The HPLC area percentage value of the compound HM-4 was 99.5% or more.

The analysis result of the compound HM-4 was as described below.

$^1$H-NMR (CD$_2$Cl$_2$, 400 MHz): δ (ppm)=7.08 (4H, t), 7.34 (6H, m), 7.47-7.57 (12H, m), 8.02 (2H, d), 8.12 (2H, s), 8.22 (4H, d).

<Synthesis Example HM-8> Synthesis of Compound HM-8

[Chemical Formula 72]

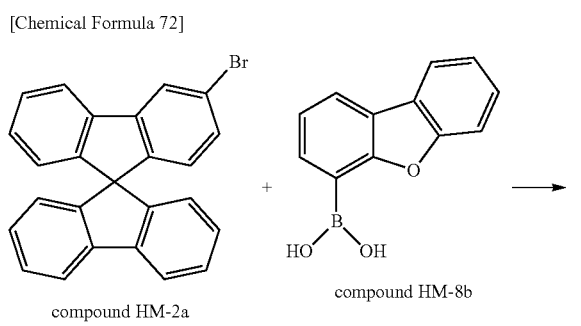

A nitrogen gas atmosphere was prepared in a reaction vessel, then, a compound HM-2a (1.64 g), a compound HM-8b (1.00 g), toluene (40 mL), tetrakis(triphenylphosphine)palladium(0) (0.24 g) and a 20% by mass tetrabutylammonium hydroxide aqueous solution (20 g) were added, and the mixture was stirred at 90° C. for 3 hours. The resultant reaction liquid was cooled down to room temperature, then, toluene was added, and the liquid was washed with ion exchanged water. The resultant organic layer was dried over anhydrous magnesium sulfate, then, filtrated through a filter paved with silica gel and Celite. The resultant filtrate was concentrated under reduced pressure, to obtain a solid. The resultant solid was crystallized using a mixed solvent of toluene and 2-propanol, then, dried at 50° C. under reduced pressure, to obtain a compound HM-8 (1.7 g). The HPLC area percentage value of the compound HM-8 was 99.5% or more.

The analysis result of the compound HM-8 was as described below.

$^{1}$H-NMR (CDCl$_{3}$, 400 MHz): δ (ppm)=8.36 (d, 1H), 8.03-7.99 (m, 1H), 7.98-7.93 (m, 2H), 7.89-7.86 (m, 2H), 7.70-7.60 (m, 3H), 7.51-7.35 (m, 6H), 7.17-7.12 (m, 3H), 6.89 (d, 1H), 6.86-6.82 (m, 2H), 6.78 (d, 1H).

<Synthesis Example HM-9> Synthesis of Compound HM-9

[Chemical Formula 73]

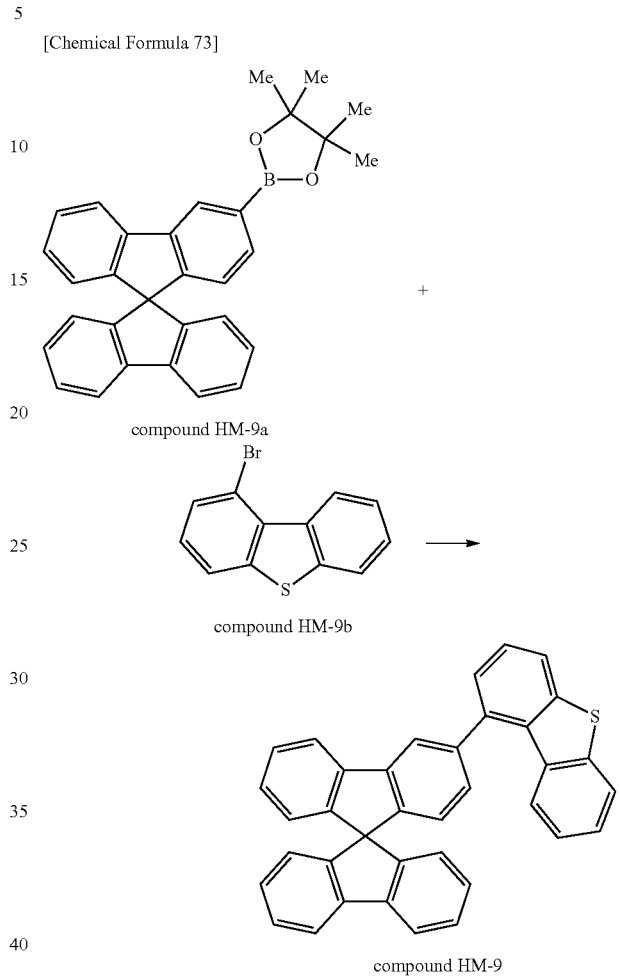

A nitrogen gas atmosphere was prepared in a reaction vessel, then, a compound HM-9a (1.86 g), a compound HM-9b (0.895 g), toluene (30 mL), tetrakis(triphenylphosphine)palladium(0) (0.19 g) and a 20% by mass tetrabutyl ammonium hydroxide aqueous solution (16 g) were added, and the mixture was stirred at 90° C. for 3 hours. The resultant reaction liquid was cooled down to room temperature, then, toluene and ion exchanged water were added, and the liquid was filtrated through a filter paved with Celite. From the resultant filtrate, an aqueous layer was removed, then, the resultant organic layer was washed with ion exchanged water. The resultant organic layer was dried over anhydrous magnesium sulfate, then, filtrated through a filter paved with silica gel and Celite. The resultant filtrate was concentrated under reduced pressure, to obtain a solid. The resultant solid was purified by silica gel column chromatography (hexane solvent), then, crystallized using a mixed solvent of tetrahydrofuran and methanol, then, crystallized using a mixed solvent of toluene and methanol, then, dried at 50° C. under reduced pressure, to obtain a compound HM-9 (1.0 g). The HPLC area percentage value of the compound HM-9 was 99.5% or more.

The analysis result of the compound HM-9 was as described below.

$^1$H-NMR (CD$_2$Cl$_2$, 400 MHz): δ (ppm)=6.73 (1H, d), 6.81 (2H, t), 6.90 (1H, d), 7.04 (1H, t), 7.12-7.23 (5H, m), 7.32-7.40 (5H, m), 7.50 (1H, t), 7.81 (2H, t), 7.93 (4H, t)

<Synthesis Example HM-13> Synthesis of Compound HM-13

[Chemical Formula 74]

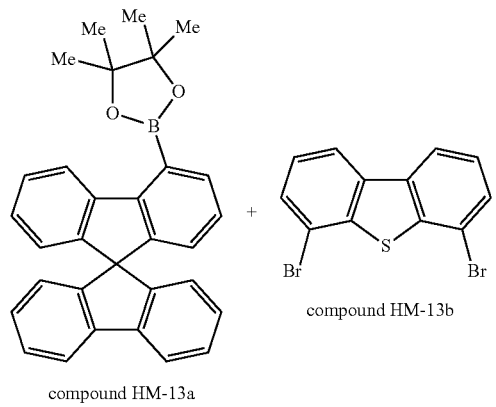

compound HM-13a compound HM-13b

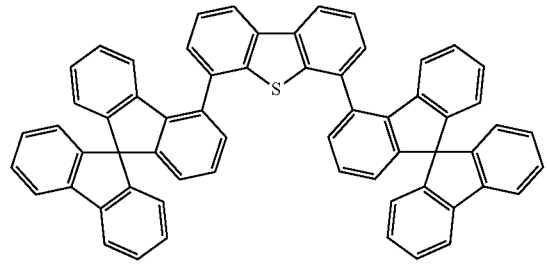

compound HM-13b

A nitrogen gas atmosphere was prepared in a reaction vessel, then, a compound HM-13a (3.07 g), a compound HM-13b (1.05 g), toluene (40 mL), tetrakis(triphenylphosphine)palladium(0) (0.18 g) and a 20% by mass tetrabutyl ammonium hydroxide aqueous solution (12 g) were added, and the mixture was stirred at 90° C. for 3 hours. The resultant reaction liquid was cooled down to room temperature, then, toluene and ion exchanged water were added, and the liquid was filtrated through a filter paved with Celite. From the resultant filtrate, an aqueous layer was removed, then, the resultant organic layer was washed with ion exchanged water. The resultant organic layer was dried over anhydrous magnesium sulfate, then, filtrated through a filter paved with silica gel and Celite. The resultant filtrate was concentrated under reduced pressure, to obtain a solid. The resultant solid was purified by silica gel column chromatography (hexane solvent), then, crystallized using a mixed solvent of toluene and 2-proanol, then, dried at 50° C. under reduced pressure, to obtain a compound HM-13 (2.0 g). The HPLC area percentage value of the compound HM-13 was 99.5% or more.

The analysis result of the compound HM-13 was as described below.

$^1$H-NMR (CD$_2$Cl$_2$, 400 MHz): δ (ppm)=6.24 (1H, d), 6.45-6.58 (6H, m), 6.65-6.74 (6H, m), 6.86 (3H, m), 7.10-7.26 (7H, m), 7.36 (3H, m), 7.67 (2H, d), 7.75-7.86 (6H, m), 8.45 (2H, d).

<Synthesis Example HM-18> Synthesis of Compound HM-18

[Chemical Formula 75]

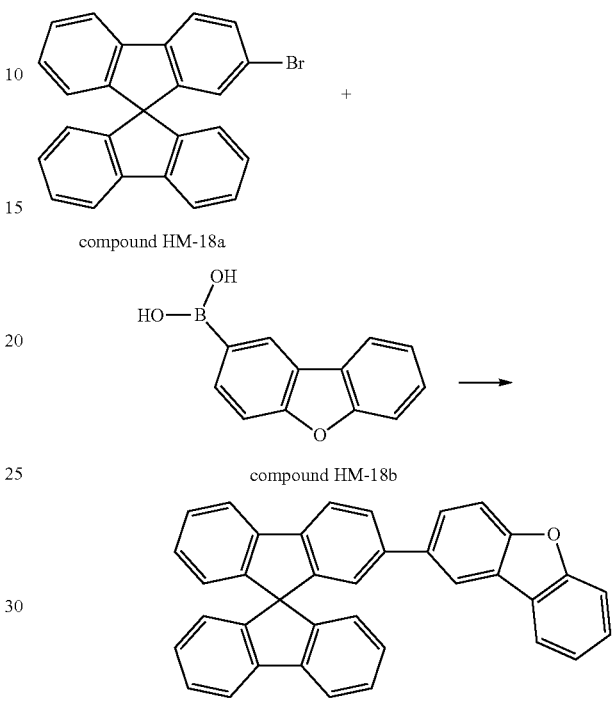

compound HM-18a compound HM-18b compound HM-18

A nitrogen gas atmosphere was prepared in a reaction vessel, then, a compound HM-18a (2.0 g), a compound HM-18b (1.2 g), toluene (50 mL), tetrakis(triphenylphosphine)palladium(0) (0.29 g) and a 20% by mass tetrabutyl ammonium hydroxide aqueous solution (20 g) were added, and the mixture was stirred at 90° C. for 3 hours. The resultant reaction liquid was cooled down to room temperature, then, toluene and ion exchanged water were added, and the liquid was filtrated through a filter paved with Celite. From the resultant filtrate, an aqueous layer was removed, then, the resultant organic layer was washed with ion exchanged water. The resultant organic layer was dried over anhydrous sodium sulfate, and filtrated. To the resultant filtrate was added activated carbon, and the mixture was stirred, then, filtrated through a filter paved with Celite and silica gel. The resultant filtrate was concentrated under reduced pressure, to obtain a solid. The resultant solid was crystallized using a mixed solvent of toluene and 2-proanol, then, dried at 50° C. under reduced pressure, to obtain a compound HM-18 (1.9 g). The HPLC area percentage value of the compound HM-18 was 99.5% or more.

The analysis result of the compound HM-18 was as described below.

$^1$H-NMR (CD$_2$Cl$_2$, 400 MHz): δ (ppm)=6.65 (1H, d), 6.74 (2H, d), 7.01 (1H, s), 7.12 (3H, m), 7.28-7.53 (8H, m), 7.73 (1H, d), 7.87-7.99 (6H, m).

<Synthesis Example HM-19> Synthesis of Compound HM-19

[Chemical Formula 76]

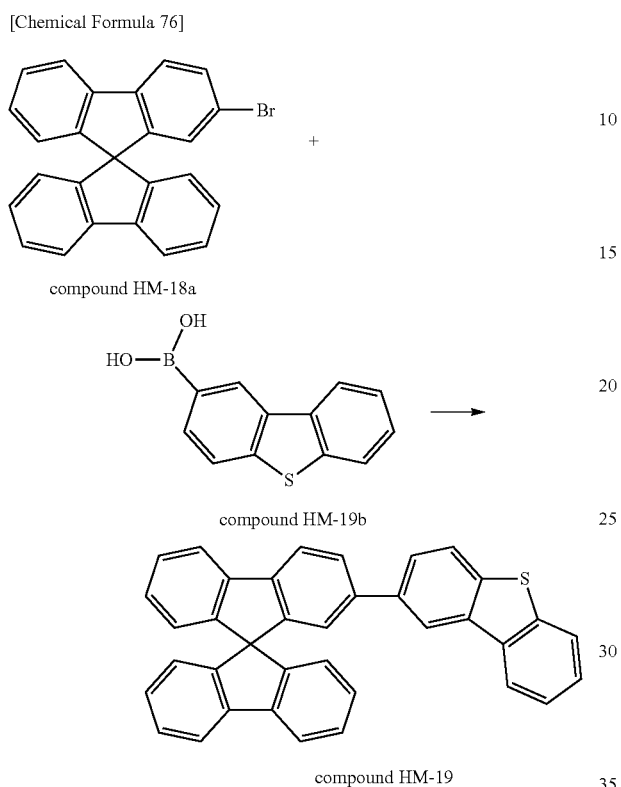

<Synthesis Example HM-20> Synthesis of Compound HM-20

[Chemical Formula 77]

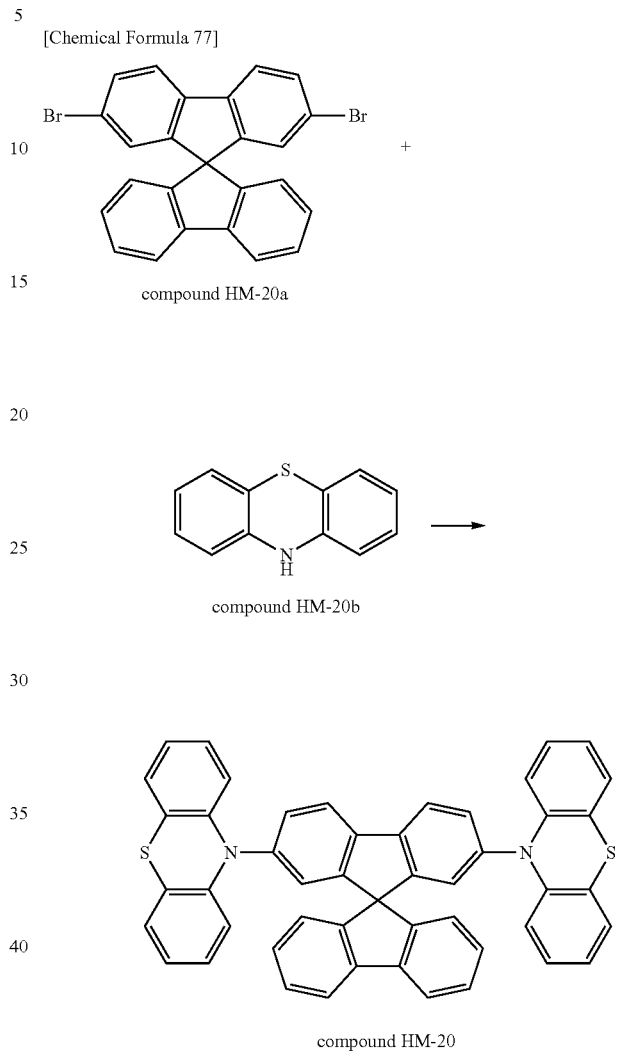

A nitrogen gas atmosphere was prepared in a reaction vessel, then, a compound HM-18a (5.0 g), a compound HM-19b (3.3 g), toluene (125 mL), tetrakis(triphenylphosphine)palladium(O) (0.73 g) and a 20% by mass tetrabutyl ammonium hydroxide aqueous solution (49 g) were added, and the mixture was stirred at 90° C. for 3 hours. The resultant reaction liquid was cooled down to room temperature, then, toluene and ion exchanged water were added, and the liquid was filtrated through a filter paved with Celite. From the resultant filtrate, an aqueous layer was removed, then, the resultant organic layer was washed with ion exchanged water. The resultant organic layer was dried over anhydrous sodium sulfate, and filtrated. To the resultant filtrate was added activated carbon, and the mixture was stirred, then, filtrated through a filter paved with Celite and silica gel. The resultant filtrate was concentrated under reduced pressure, to obtain a solid. The resultant solid was crystallized using a mixed solvent of toluene and 2-proanol, then, dried at 50° C. under reduced pressure, to obtain a compound HM-19 (5.0 g). The HPLC area percentage value of the compound HM-19 was 99.5% or more.

The analysis result of the compound HM-19 was as described below.

$^1$H-NMR (CD$_2$Cl$_2$, 400 MHz): δ (ppm)=6.66 (1H, d), 6.74 (2H, d), 7.13 (4H, m), 7.37-7.52 (6H, m), 7.76-7.99 (7H, m), 8.12 (1H, d), 8.19 (1H, s).

A nitrogen gas atmosphere was prepared in a reaction vessel, then, a compound HM-20a (3.0 g), a compound HM-20b (2.8 g), toluene (150 mL), palladium(II) acetate (43 mg), tri-tert-butylphosphonium tetrafluoroborate (0.12 g) and sodium tert-butoxide (3.7 g) were added, and the mixture was stirred at 105° C. for 3 hours. The resultant reaction liquid was cooled down to room temperature, to deposit a solid. The resultant solid was collected by filtration, then, dissolved in chloroform. To the resultant chloroform solution was added activated carbon, and the mixture was stirred, then, filtrated through a filter paved with Celite and silica gel. The resultant filtrate was concentrated under reduced pressure, to obtain a solid. The resultant solid was crystallized using toluene, then, dried at 50° C. under reduced pressure, to obtain a compound HM-20 (3.0 g). The HPLC area percentage value of the compound HM-20 was 99.5%.

The analysis result of the compound HM-20 was as described below.

$^1$H-NMR (CD$_2$Cl$_2$, 400 MHz): δ (ppm)=6.09 (2H, d), 6.72-6.77 (5H, m), 6.85-6.92 (3H, m), 7.11-7.21 (1H, m), 7.32 (1H, t), 7.45 (1H, d), 7.79 (1H, d), 8.15 (1H, d).

<Synthesis Example HM-21> Synthesis of Compound HM-21

[Chemical Formula 78]

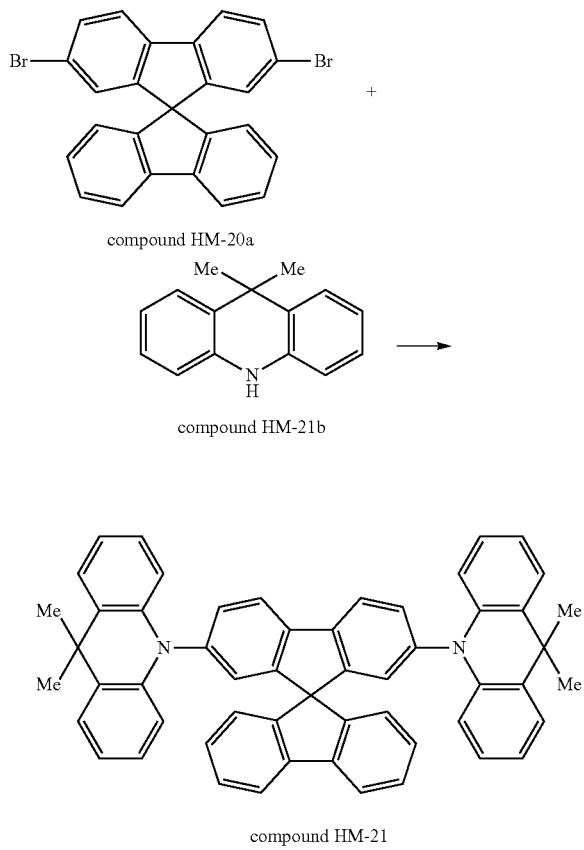

compound HM-20a compound HM-21b compound HM-21

A nitrogen gas atmosphere was prepared in a reaction vessel, then, a compound HM-20a (1.5 g), a compound HM-21b (1.5 g), toluene (75 mL), palladium(II) acetate (21 mg), tri-tert-butylphosphonium tetrafluoroborate (61 mg) and sodium tert-butoxide (1.2 g) were added, and the mixture was stirred at 105° C. for 3 hours. The resultant reaction liquid was cooled down to room temperature, then, toluene and ion exchanged water were added, and the liquid was filtrated through a filter paved with Celite. From the resultant filtrate, an aqueous layer was removed, then, the resultant organic layer was washed with ion exchanged water. The resultant organic layer was dried over anhydrous sodium sulfate, and filtrated. The resultant filtrate was concentrated under reduced pressure, to obtain a solid. The resultant solid was dissolved in chloroform. To the resultant chloroform solution was added activated carbon, and the mixture was stirred, then, filtrated through a filter paved with Celite and silica gel. The resultant filtrate was concentrated under reduced pressure, to obtain a solid. The resultant solid was crystallized using toluene, then, dried at 50° C. under reduced pressure, to obtain a compound HM-21 (1.3 g). The HPLC area percentage value of the compound HM-21 was 99.5% or more.

The analysis result of the compound HM-21 was as described below.

$^1$H-NMR (CD$_2$Cl$_2$, 400 MHz): δ (ppm)=1.54 (6H, s), 6.16 (2H, d), 6.70 (1H, s), 6.80-6.94 (5H, m), 7.15 (1H, t), 7.28-7.39 (4H, m), 7.74 (1H, d), 8.19 (1H, d).

<Synthesis Example ETL1> Synthesis of Polymer Compound ETL-1

An inert gas atmosphere was prepared in a reaction vessel, then, the compound M4 (9.23 g), the compound M5 (4.58 g), dichlorobis(tris-o-methoxyphenylphosphine)palladium (8.6 mg), methyltrioctylammonium chloride (trade name: Aliquat336 (registered trademark) manufactured by Sigma Aldrich)(0.098 g) and toluene (175 mL) were added, and the mixture was heated at 105° C. Thereafter, into this was dropped a 12% by mass sodium carbonate aqueous solution (40.3 mL), and the mixture was refluxed for 29 hours. Thereafter, to this were added phenylboronic acid (0.47 g) and dichlorobis(tris-o-methoxyphenylphosphine)palladium (8.7 mg), and the mixture was refluxed for 14 hours. Thereafter, to this was added a sodium diethyldithiacarbamate aqueous solution, and the mixture was stirred at 80° C. for 2 hours. The resultant reaction liquid was cooled, then, dropped into methanol, to generate a precipitate. The resultant precipitate was collected by filtration, and washed with methanol and water, respectively, then, dried. The resultant solid was dissolved in chloroform, and purified by sequentially passing through an alumina column and a silica gel column through which chloroform had been passed previously. The resultant purified liquid was dropped into methanol, and the liquid was stirred, to generate a precipitate. The resultant precipitate was collected by filtration, and dried, to obtain a polymer compound ETL-1a (7.15 g). The polymer compound ETL-1a had an Mn of 3.2×10$^4$ and an Mw of 6.0×10$^4$.

The polymer compound ETL-1a is a copolymer constituted of a constitutional unit derived from the compound M4 and a constitutional unit derived from the compound M5 at a molar ratio of 50:50, according to the theoretical values calculated from the amounts of the charged raw materials.

An argon gas atmosphere was prepared in a reaction vessel, then, the polymer compound ETL-1a (3.1 g), tetrahydrofuran (130 mL), methanol (66 mL), cesium hydroxide monohydrate (2.1 g) and water (12.5 mL) were added, and the mixture was stirred at 60° C. for 3 hours. Thereafter, to this was added methanol (220 mL), and the mixture was stirred for 2 hours. The resultant reaction mixture was concentrated, then, dropped into isopropyl alcohol, and the liquid was stirred, to generate a precipitate. The resultant precipitate was collected by filtration, and dried, to obtain a polymer compound ETL-1 (3.5 g). By 1H-NMR analysis of the polymer compound ETL-1, it was confirmed that a signal of an ethyl ester site in the polymer compound ETL-1 disappeared and reaction was completed.

The polymer compound ETL-1 is a copolymer constituted of a constitutional unit represented by the following formula and a constitutional unit derived from the compound M5 at a molar ratio of 50:50, according to the theoretical values calculated from the amounts of the charged raw materials of the polymer compound ETL-1a.

[Chemical Formula 79]

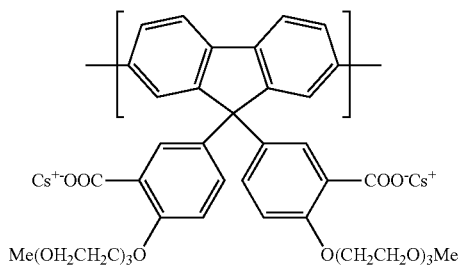

<Example D1> Fabrication and Evaluation of Light Emitting Device D1

(Formation of Anode and Hole Injection Layer)

An ITO film with a thickness of 45 nm was deposited on a glass substrate by a sputtering method, to form an anode. On the anode, a hole injection material ND-3202 (manufactured by Nissan Chemical Corporation) was spin-coated to form a film with a thickness of 35 nm. In an air atmosphere, the film was heated on a hot plate at 50° C. for 3 minutes, further heated at 230° C. for 15 minutes, to form a hole injection layer.

(Formation of Hole Transporting Layer)

The polymer compound HTL-1 was dissolved in xylene at a concentration of 0.7% by mass. The resultant xylene solution was spin-coated on the hole injection layer, to form a film with a thickness of 20 nm, and the film was heated on a hot plate at 180° C. for 60 minutes under a nitrogen gas atmosphere, to form a hole transporting layer.

(Formation of Light Emitting Layer)

The compound HM-2, the compound HM-3 and the phosphorescent compound B2 (compound HM-2/compound HM-3/phosphorescent compound B2=37.5% by mass/37.5% by mass/25% by mass) were dissolved at a concentration of 2.0% by mass in toluene. The resultant toluene solution was spin-coated on the hole transporting layer, to form a film with a thickness of 75 nm, and the film was heated at 130° C. for 10 minutes under a nitrogen gas atmosphere, to form a light emitting layer.

(Formation of Electron Transporting Layer)

The polymer compound ETL-1 was dissolved in 2,2,3,3,4,4,5,5-octafluoro-1-pentanol at a concentration of 0.25% by mass. The resultant 2,2,3,3,4,4,5,5-octafluoro-1-pentanol solution was spin-coated on the light emitting layer, to form a film with a thickness of 10 nm, and the film was heated at 130° C. for 10 minutes under a nitrogen gas atmosphere, to form an electron transporting layer.

(Formation of Cathode)

The substrate carrying the electron transporting layer formed thereon was placed in a vapor deposition machine and the inner pressure thereof was reduced to $1.0 \times 10^{-4}$ Pa or less, then, as cathode, sodium fluoride was vapor-deposited with a thickness of about 4 nm on the electron transporting layer, then, aluminum was vapor-deposited with a thickness of about 80 nm on the sodium fluoride layer. After vapor deposition, sealing was performed with a glass substrate, to fabricate a light emitting device D1.

(Evaluation of Light Emitting Device)

Voltage was applied to the light emitting device D1, to observe EL light emission. The external quantum efficiency at 100 cd/m² was measured. The CIE chromaticity coordinate (x, y) at 100 cd/m² was (0.20, 0.44).

<Example D2> Fabrication and Evaluation of Light Emitting Device D2

A light emitting device D2 was fabricated in the same manner as in Example D1, except that "the compound HM-3, the compound HM-8 and the phosphorescent compound B2 (compound HM-3/compound HM-8/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D2, to observe EL light emission. The external quantum efficiency at 100 cd/m² was measured. The CIE chromaticity coordinate (x, y) at 100 cd/m² was (0.20, 0.44).

<Example D3> Fabrication and Evaluation of Light Emitting Device D3

A light emitting device D3 was fabricated in the same manner as in Example D1, except that "the compound HM-3, the compound HM-9 and the phosphorescent compound B2 (compound HM-3/compound HM-9/phosphorescent compound B2=37.5% by mass/37.5% by mass/25% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D3, to observe EL light emission. The external quantum efficiency at 100 cd/m² was measured. The CIE chromaticity coordinate (x, y) at 100 cd/m² was (0.19, 0.42).

<Example D4> Fabrication and Evaluation of Light Emitting Device D4

A light emitting device D4 was fabricated in the same manner as in Example D1, except that "the compound HM-3, the compound HM-10 and the phosphorescent compound B2 (compound HM-3/compound HM-10/phosphorescent compound B2=37.5% by mass/37.5% by mass/25% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D4, to observe EL light emission. The external quantum efficiency at 100 cd/m² was measured. The CIE chromaticity coordinate (x, y) at 100 cd/m² was (0.19, 0.44).

<Example D5> Fabrication and Evaluation of Light Emitting Device D5

A light emitting device D5 was fabricated in the same manner as in Example D1, except that "the compound HM-3, the compound HM-11 and the phosphorescent compound B2 (compound HM-3/compound HM-11/phosphorescent compound B2=37.5% by mass/37.5% by mass/25% by mass)" were used instead of "the compound HM-2, the compound HM-3 and the phosphorescent compound B2

(compound HM-2/compound HM-3/phosphorescent compound B2=37.5% by mass/37.5% by mass/25% by mass)" in (Formation of light emitting layer) in Example D1.

Voltage was applied to the light emitting device D5, to observe EL light emission. The external quantum efficiency at 100 cd/m$^2$ was measured. The CIE chromaticity coordinate (x, y) at 100 cd/m$^2$ was (0.19, 0.44).

<Example D6> Fabrication and Evaluation of Light Emitting Device D6

A light emitting device D6 was fabricated in the same manner as in Example D1, except that "the compound HM-3, the compound HM-12 and the phosphorescent compound B2 (compound HM-3/compound HM-12/phosphorescent compound B2=37.5% by mass/37.5% by mass/25% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D6, to observe EL light emission. The external quantum efficiency at 100 cd/m$^2$ was measured. The CIE chromaticity coordinate (x, y) at 100 cd/m$^2$ was (0.20, 0.44).

<Example D7> Fabrication and Evaluation of Light Emitting Device D7

A light emitting device D7 was fabricated in the same manner as in Example D1, except that "the compound HM-3, the compound HM-13 and the phosphorescent compound B2 (compound HM-3/compound HM-13/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D7, to observe EL light emission. The external quantum efficiency at 100 cd/m$^2$ was measured. The CIE chromaticity coordinate (x, y) at 100 cd/m$^2$ was (0.20, 0.44).

<Example D8> Fabrication and Evaluation of Light Emitting Device D8

A light emitting device D8 was fabricated in the same manner as in Example D1, except that "the compound HM-3, the compound HM-14 and the phosphorescent compound B2 (compound HM-3/compound HM-14/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D8, to observe EL light emission. The external quantum efficiency at 100 cd/m$^2$ was measured. The CIE chromaticity coordinate (x, y) at 100 cd/m$^2$ was (0.21, 0.46).

<Example D9> Fabrication and Evaluation of Light Emitting Device D9

A light emitting device D9 was fabricated in the same manner as in Example D1, except that "the compound HM-3, the compound HM-4 and the phosphorescent compound B2 (compound HM-3/compound HM-4/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D9, to observe EL light emission. The external quantum efficiency at 100 cd/m$^2$ was measured. The CIE chromaticity coordinate (x, y) at 100 cd/m$^2$ was (0.21, 0.46).

<Example D10> Fabrication and Evaluation of Light Emitting Device D10

A light emitting device D10 was fabricated in the same manner as in Example D1, except that "the compound HM-3, the compound HM-1 and the phosphorescent compound B2 (compound HM-3/compound HM-1/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D10, to observe EL light emission. The external quantum efficiency at 100 cd/m$^2$ was measured. The CIE chromaticity coordinate (x, y) at 100 cd/m$^2$ was (0.19, 0.42).

<Example D11> Fabrication and Evaluation of Light Emitting Device D11

A light emitting device D11 was fabricated in the same manner as in Example D1, except that "the phosphorescent compound B1" was used instead of "the phosphorescent compound B2" in (Formation of light emitting layer) in Example D1.

Voltage was applied to the light emitting device D11, to observe EL light emission. The external quantum efficiency at 100 cd/m$^2$ was measured. The CIE chromaticity coordinate (x, y) at 100 cd/m$^2$ was (0.17, 0.35).

<Comparative Example CD1> Fabrication and Evaluation of Light Emitting Device CD1

A light emitting device CD1 was fabricated in the same manner as in Example D1, except that "the compound HM-3 and the phosphorescent compound B1 (compound HM-3/phosphorescent compound B1=75% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD1, to observe EL light emission. The external quantum efficiency at 100 cd/m$^2$ was measured. The CIE chromaticity coordinate (x, y) at 100 cd/m$^2$ was (0.16, 0.34).

The results of Examples D1 to D11 and Comparative Example CD1 are shown in Table 1. The relative value of the external quantum efficiency of the light emitting devices D1 to D11 when the external quantum efficiency of the light emitting device CD1 was taken as 1.0 is shown.

TABLE 1

| | light emitting device | light emitting layer material | composition ratio (% by mass) | external quantum efficiency (relative value) |
|---|---|---|---|---|
| Example D1 | D1 | HM-3/HM-2/B2 | 37.5/37.5/25 | 49.8 |
| Example D2 | D2 | HM-3/HM-8/B2 | 37.5/37.5/25 | 64.1 |
| Example D3 | D3 | HM-3/HM-9/B2 | 37.5/37.5/25 | 57.5 |
| Example D4 | D4 | HM-3/HM-10/B2 | 37.5/37.5/25 | 68.9 |
| Example D5 | D5 | HM-3/HM-11/B2 | 37.5/37.5/25 | 75.1 |
| Example D6 | D6 | HM-3/HM-12/B2 | 37.5/37.5/25 | 64.7 |
| Example D7 | D7 | HM-3/HM-13/B2 | 37.5/37.5/25 | 75.6 |
| Example D8 | D8 | HM-3/HM-14/B2 | 37.5/37.5/25 | 45.7 |
| Example D9 | D9 | HM-3/HM-4/B2 | 37.5/37.5/25 | 73.1 |
| Example D10 | D10 | HM-3/HM-1/B2 | 37.5/37.5/25 | 83.5 |
| Example D11 | D11 | HM-3/HM-2/B1 | 37.5/37.5/25 | 3.1 |
| Comparative Example CD1 | CD1 | HM-3/B1 | 75/25 | 1.0 |

<Example D12> Fabrication and Evaluation of Light Emitting Device D12

A light emitting device D3 was fabricated in the same manner as in Example D1, except that "the compound HM-1" was used instead of "the compound HM-3" in (Formation of light emitting layer) in Example D1.

Voltage was applied to the light emitting device D3, to observe EL light emission. The external quantum efficiency at 1000 cd/m$^2$ was measured. The CIE chromaticity coordinate (x, y) at 1000 cd/m$^2$ was (0.19, 0.44).

<Example D13> Fabrication and Evaluation of Light Emitting Device D13

A light emitting device D13 was fabricated in the same manner as in Example D1, except that "the compound HM-1, the compound HM-15 and the phosphorescent compound B2 (compound HM-1/compound HM-15/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D13, to observe EL light emission. The external quantum efficiency at 1000 cd/m$^2$ was measured. The CIE chromaticity coordinate (x, y) at 1000 cd/m$^2$ was (0.18, 0.42).

<Example D14> Fabrication and Evaluation of Light Emitting Device D14

A light emitting device D14 was fabricated in the same manner as in Example D1, except that "the compound HM-1, the compound HM-16 and the phosphorescent compound B2 (compound HM-1/compound HM-16/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D14, to observe EL light emission. The external quantum efficiency at 1000 cd/m$^2$ was measured. The CIE chromaticity coordinate (x, y) at 1000 cd/m$^2$ was (0.19, 0.42).

<Example D15> Fabrication and Evaluation of Light Emitting Device D15

A light emitting device D15 was fabricated in the same manner as in Example D1, except that "the compound HM-1, the compound HM-17 and the phosphorescent compound B2 (compound HM-1/compound HM-17/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D15, to observe EL light emission. The external quantum efficiency at 1000 cd/m$^2$ was measured. The CIE chromaticity coordinate (x, y) at 1000 cd/m$^2$ was (0.18, 0.39).

<Comparative Example CD2> Fabrication and Evaluation of Light Emitting Device CD2

A light emitting device CD2 was fabricated in the same manner as in Example D1, except that "the compound HM-1 and the phosphorescent compound B2 (compound HM-1/phosphorescent compound B2=75% by mass/25% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD2, to observe EL light emission. The external quantum efficiency at 1000 cd/m$^2$ was measured. The CIE chromaticity coordinate (x, y) at 1000 cd/m$^2$ was (0.20, 0.46).

<Comparative Example CD3> Fabrication and Evaluation of Light Emitting Device CD3

A light emitting device CD3 was fabricated in the same manner as in Example D1, except that "the compound HM-2 and the phosphorescent compound B2 (compound HM-2/phosphorescent compound B2=75% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD3, to observe EL light emission. The external quantum efficiency at 1000 cd/m$^2$ was measured. The CIE chromaticity coordinate (x, y) at 1000 cd/m$^2$ was (0.20, 0.45).

The results of Examples D12 to D15, Comparative Example CD2 and Comparative Example CD3 are shown in Table 2. The relative value of the external quantum efficiency of the light emitting devices D12 to D15 and CD3 when the external quantum efficiency of the light emitting device CD2 was taken as 1.0 is shown.

TABLE 2

| | light emitting device | light emitting layer material | composition ratio (% by mass) | external quantum efficiency (relative value) |
|---|---|---|---|---|
| Example D12 | D12 | HM-1/HM-2/B2 | 37.5/37.5/25 | 1.5 |
| Example D13 | D13 | HM-1/HM-15/B2 | 37.5/37.5/25 | 2.1 |
| Example D14 | D14 | HM-1/HM-16/B2 | 37.5/37.5/25 | 1.7 |

TABLE 2-continued

| light emitting device | light emitting layer material | composition ratio (% by mass) | external quantum efficiency (relative value) |
|---|---|---|---|
| Example D15 | D15 | HM-1/HM-17/B2 | 37.5/37.5/25 | 1.6 |
| Comparative Example CD2 | CD2 | HM-1/B2 | 75/25 | 1.0 |
| Comparative Example CD3 | CD3 | HM-2/B2 | 75/25 | 0.6 |

<Example D16> Fabrication and Evaluation of Light Emitting Device D16

A light emitting device D16 was fabricated in the same manner as in Example D1, except that "the compound HM-4, the compound HM-1 and the phosphorescent compound B2 (compound HM-4/compound HM-1/phosphorescent compound B2=37.5% by mass/37.5% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D16, to observe EL light emission. The external quantum efficiency at 10000 cd/m² was measured. The CIE chromaticity coordinate (x, y) at 10000 cd/m² was (0.19, 0.44).

<Comparative Example CD4> Fabrication and Evaluation of Light Emitting Device CD4

A light emitting device CD4 was fabricated in the same manner as in Example D1, except that "the compound HM-4 and the phosphorescent compound B2 (compound HM-4/phosphorescent compound B2=75% by mass/25% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD4, to observe EL light emission. The external quantum efficiency at 10000 cd/m² was measured. The CIE chromaticity coordinate (x, y) at 10000 cd/m² was (0.22, 0.48).

The results of Example D16 and Comparative Example CD4 are shown in Table 3. The relative value of the external quantum efficiency of the light emitting device D16 when the external quantum efficiency of the light emitting device CD4 was taken as 1.0 is shown.

TABLE 3

| light emitting device | light emitting layer material | composition ratio (% by mass) | external quantum efficiency (relative value) |
|---|---|---|---|
| Example D16 | D16 | HM-4/HM-1/B2 | 37.5/37.5/25 | 1.2 |
| Comparative Example CD4 | CD4 | HM-4/B2 | 75/25 | 1.0 |

<Example D17> Fabrication and Evaluation of Light Emitting Device D17

A light emitting device D17 was fabricated in the same manner as in Example D1, except that "the compound HM-5, the compound HM-6 and the phosphorescent compound G1 (compound HM-5/compound HM-6/phosphorescent compound G1=35% by mass/35% by mass/30% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D17, to observe EL light emission. The external quantum efficiency at 100 cd/m² was measured. The CIE chromaticity coordinate (x, y) at 100 cd/m² was (0.34, 0.62).

<Comparative Example CD5> Fabrication and Evaluation of Light Emitting Device CD5

A light emitting device CD5 was fabricated in the same manner as in Example D1, except that "the compound HM-5, the compound HM-7 and the phosphorescent compound G1 (compound HM-5/compound HM-7/phosphorescent compound G1=35% by mass/35% by mass/30% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD5, to observe EL light emission. The external quantum efficiency at 100 cd/m² was measured. The CIE chromaticity coordinate (x, y) at 100 cd/m² was (0.34, 0.61).

The results of Example D5 and Comparative Example CD4 are shown in Table 4. The relative value of the external quantum efficiency of the light emitting device D5 when the external quantum efficiency of the light emitting device CD4 was taken as 1.0 is shown.

TABLE 4

| light emitting device | light emitting layer material | composition ratio (% by mass) | external quantum efficiency (relative value) |
|---|---|---|---|
| Example D17 | D17 | HM-5/HM-6/G1 | 35/35/30 | 8.5 |
| Comparative Example CD5 | CD5 | HM-5/HM-7/G1 | 35/35/30 | 1.0 |

<Example D18> Fabrication and Evaluation of Light Emitting Device D18

A light emitting device D18 was fabricated in the same manner as in Example D1, except that "the compound HM-5, the compound HM-6 and the phosphorescent compound G2 (compound HM-5/compound HM-6/phosphorescent compound G2=35% by mass/35% by mass/30% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1, and further, "the polymer compound HTL-2" was used instead of "polymer compound HTL-1" in (Formation of hole transporting layer) in Example D1.

Voltage was applied to the light emitting device D18, to observe EL light emission. The external quantum efficiency at 100 cd/m$^2$ was measured. The CIE chromaticity coordinate (x, y) at 100 cd/m$^2$ was (0.35, 0.60).

<Example D19> Fabrication and Evaluation of Light Emitting Device D19

A light emitting device D19 was fabricated in the same manner as in Example D18, except that "the compound HM-18" was used instead of "the compound HM-5" in (Formation of light emitting layer) in Example D18.

Voltage was applied to the light emitting device D19, to observe EL light emission. The external quantum efficiency at 100 cd/m$^2$ was measured. The CIE chromaticity coordinate (x, y) at 100 cd/m$^2$ was (0.31, 0.63).

<Example D20> Fabrication and Evaluation of Light Emitting Device D20

A light emitting device D20 was fabricated in the same manner as in Example D18, except that "the compound HM-19" was used instead of "the compound HM-5" in (Formation of light emitting layer) in Example D18.

Voltage was applied to the light emitting device D20, to observe EL light emission. The external quantum efficiency at 100 cd/m$^2$ was measured. The CIE chromaticity coordinate (x, y) at 100 cd/m$^2$ was (0.32, 0.62).

<Example D21> Fabrication and Evaluation of Light Emitting Device D21

A light emitting device D21 was fabricated in the same manner as in Example D18, except that "the compound HM-11" was used instead of "the compound HM-5" in (Formation of light emitting layer) in Example D18.

Voltage was applied to the light emitting device D21, to observe EL light emission. The external quantum efficiency at 100 cd/m$^2$ was measured. The CIE chromaticity coordinate (x, y) at 100 cd/m$^2$ was (0.31, 0.63).

<Example D22> Fabrication and Evaluation of Light Emitting Device D22

A light emitting device D22 was fabricated in the same manner as in Example D18, except that "the compound HM-20" was used instead of "the compound HM-5" in (Formation of light emitting layer) in Example D18.

Voltage was applied to the light emitting device D22, to observe EL light emission. The external quantum efficiency at 100 cd/m$^2$ was measured. The CIE chromaticity coordinate (x, y) at 100 cd/m$^2$ was (0.33, 0.62).

<Example D23> Fabrication and Evaluation of Light Emitting Device D23

A light emitting device D23 was fabricated in the same manner as in Example D18, except that "the compound HM-21" was used instead of "the compound HM-5" in (Formation of light emitting layer) in Example D18.

Voltage was applied to the light emitting device D23, to observe EL light emission. The external quantum efficiency at 100 cd/m$^2$ was measured. The CIE chromaticity coordinate (x, y) at 100 cd/m$^2$ was (0.31, 0.63).

<Example D24> Fabrication and Evaluation of Light Emitting Device D24

A light emitting device D24 was fabricated in the same manner as in Example D18, except that "the compound HM-3" was used instead of "the compound HM-5" in (Formation of light emitting layer) in Example D18.

Voltage was applied to the light emitting device D24, to observe EL light emission. The external quantum efficiency at 100 cd/m$^2$ was measured. The CIE chromaticity coordinate (x, y) at 100 cd/m$^2$ was (0.32, 0.62).

<Example D25> Fabrication and Evaluation of Light Emitting Device D25

A light emitting device D25 was fabricated in the same manner as in Example D18, except that "the compound HM-3, the compound HM-11 and the phosphorescent compound G2 (compound HM-3/compound HM-11/phosphorescent compound G2=35% by mass/35% by mass/30% by mass)" were used instead of "the compound HM-5, the compound HM-6 and the phosphorescent compound G2 (compound HM-5/compound HM-6/phosphorescent compound G2=35% by mass/35% by mass/30% by mass)" in (Formation of light emitting layer) in Example D18.

Voltage was applied to the light emitting device D25, to observe EL light emission. The external quantum efficiency at 100 cd/m$^2$ was measured. The CIE chromaticity coordinate (x, y) at 100 cd/m$^2$ was (0.30, 0.64).

<Example D26> Fabrication and Evaluation of Light Emitting Device D26

A light emitting device D26 was fabricated in the same manner as in Example D18, except that "the compound HM-3, the compound HM-2 and the phosphorescent compound G2 (compound HM-3/compound HM-2/phosphorescent compound G2=35% by mass/35% by mass/30% by mass)" were used instead of "the compound HM-5, the compound HM-6 and the phosphorescent compound G2 (compound HM-5/compound HM-6/phosphorescent compound G2=35% by mass/35% by mass/30% by mass)" in (Formation of light emitting layer) in Example D18.

Voltage was applied to the light emitting device D26, to observe EL light emission. The external quantum efficiency at 100 cd/m$^2$ was measured. The CIE chromaticity coordinate (x, y) at 100 cd/m$^2$ was (0.30, 0.64).

<Example D27> Fabrication and Evaluation of Light Emitting Device D27

A light emitting device D27 was fabricated in the same manner as in Example D18, except that "the compound HM-2, the compound HM-14 and the phosphorescent compound G2 (compound HM-2/compound HM-14/phosphorescent compound G2=35% by mass/35% by mass/30% by mass)" were used instead of "the compound HM-5, compound HM-6 and the phosphorescent compound G2 (compound HM-5/compound HM-6/phosphorescent compound G2=35% by mass/35% by mass/30% by mass)" in (Formation of light emitting layer) in Example D18.

Voltage was applied to the light emitting device D27, to observe EL light emission. The external quantum efficiency at 100 cd/m$^2$ was measured. The CIE chromaticity coordinate (x, y) at 100 cd/m$^2$ was (0.31, 0.64).

\<Comparative Example CD6\> Fabrication and Evaluation of Light Emitting Device CD6

A light emitting device CD6 was fabricated in the same manner as in Example D18, except that "the compound HM-5, the compound HM-7 and the phosphorescent compound G2 (compound HM-5/compound HM-7/phosphorescent compound G2=35% by mass/35% by mass/30% by mass)" were used instead of "the compound HM-5, the compound HM-6 and the phosphorescent compound G2 (compound HM-5/compound HM-6/phosphorescent compound G2=35% by mass/35% by mass/30% by mass)" in (Formation of light emitting layer) in Example D18.

Voltage was applied to the light emitting device CD6, to observe EL light emission. The external quantum efficiency at 100 cd/m² was measured. The CIE chromaticity coordinate (x, y) at 100 cd/m² was (0.32, 0.54).

The results of Examples D18 to D27 and Comparative Example CD6 are shown in Table 5. The relative value of the external quantum efficiency of the light emitting devices D18 to D27 when the external quantum efficiency of the light emitting device CD6 was taken as 1.0 is shown.

TABLE 5

| | light emitting device | light emitting layer material | composition ratio (% by mass) | external quantum efficiency (relative value) |
|---|---|---|---|---|
| Example D18 | D18 | HM-5/HM-6/G2 | 35/35/30 | 9.4 |
| Example D19 | D19 | HM-18/HM-6/G2 | 35/35/30 | 122.3 |
| Example D20 | D20 | HM-19/HM-6/G2 | 35/35/30 | 114.6 |
| Example D21 | D21 | HM-11/HM-6/G2 | 35/35/30 | 118.2 |
| Example D22 | D22 | HM-20/HM-6/G2 | 35/35/30 | 195.3 |
| Example D23 | D23 | HM-21/HM-6/G2 | 35/35/30 | 251.9 |
| Example D24 | D24 | HM-3/HM-6/G2 | 35/35/30 | 114.2 |
| Example D25 | D25 | HM-3/HM-11/G2 | 35/35/30 | 507.1 |
| Example D26 | D26 | HM-3/HM-2/G2 | 35/35/30 | 406.1 |
| Example D27 | D27 | HM-2/HM-14/G2 | 35/35/30 | 351.9 |
| Comparative Example CD6 | CD6 | HM-5/HM-7/G2 | 35/35/30 | 1.0 |

\<Example D28\> Fabrication and Evaluation of Light Emitting Device D28

A light emitting device D28 was fabricated in the same manner as in Example D1, except that "the compound HM-5, the compound HM-1 and the phosphorescent compound $R^1$ (compound HM-5/compound HM-1/phosphorescent compound $R^1$=45% by mass/45% by mass/10% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D28, to observe EL light emission. The external quantum efficiency at 100 cd/m² was measured. The CIE chromaticity coordinate (x, y) at 100 cd/m² was (0.67, 0.33).

\<Example D29\> Fabrication and Evaluation of Light Emitting Device D29

A light emitting device D29 was fabricated in the same manner as in Example D1, except that "the compound HM-5, the compound HM-6 and the phosphorescent compound R1 (compound HM-5/compound HM-6/phosphorescent compound R1=45% by mass/45% by mass/10% by mass)" were used instead of "the compound HM-2, the compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device D29, to observe EL light emission. The external quantum efficiency at 100 cd/m² was measured. The CIE chromaticity coordinate (x, y) at 100 cd/m² was (0.65, 0.35).

\<Comparative Example CD7\> Fabrication and Evaluation of Light Emitting Device CD7

A light emitting device CD7 was fabricated in the same manner as in Example D1, except that "the compound HM-5, the compound HM-7 and the phosphorescent compound R1 (compound HM-5/compound HM-7/phosphorescent compound $R^1$=45% by mass/45% by mass/10% by mass)" were used instead of "the compound HM-2, compound HM-3 and the phosphorescent compound B2 (compound HM-2/compound HM-3/phosphorescent compound B2=37.5% by mass/37.5% by mass/25% by mass)" in (Formation of light emitting layer) in Example D1.

Voltage was applied to the light emitting device CD7, to observe EL light emission. The external quantum efficiency at 100 cd/m² was measured. The CIE chromaticity coordinate (x, y) at 100 cd/m² was (0.65, 0.34).

The results of Example D28, Example D29 and Comparative Example CD7 are shown in Table 6. The relative value of the external quantum efficiency of the light emitting devices D28 and D29 when the external quantum efficiency of the light emitting device CD7 was taken as 1.0 is shown.

TABLE 6

| | light emitting device | light emitting layer material | composition ratio (% by mass) | external quantum efficiency (relative value) |
|---|---|---|---|---|
| Example D28 | D28 | HM-5/HM-1/R1 | 45/45/10 | 26.5 |
| Example D29 | D29 | HM-5/HM-6/R1 | 45/45/10 | 2.7 |
| Comparative Example CD7 | CD7 | HM-5/HM-7/R1 | 45/45/10 | 1.0 |

INDUSTRIAL APPLICABILITY

According to the present invention, a composition which is useful for production of a light emitting device excellent in external quantum efficiency can be provided. Further, according to the present invention, a light emitting device comprising this composition can be provided.

The invention claimed is:

1. A composition comprising two or more compounds represented by the formula (C-1) and a phosphorescent compound, wherein
   at least one of the two or more compounds represented by the formula (C-1) is a compound in which $R^C$ is a group represented by the formula (C'-1):

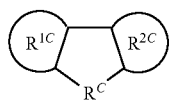

(C-1)

wherein

Ring $R^{1C}$ and Ring $R^{2C}$ each independently represent an aromatic hydrocarbon ring or an aromatic hetero ring, and the foregoing rings optionally have a substituent, and when a plurality of the substituents are present, they may be combined together to form a ring together with the atoms to which they are attached, $R^C$ represents an oxygen atom, a sulfur atom or a group represented by the formula (C'-1),

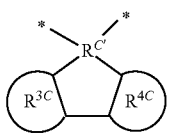

(C'-1)

wherein

Ring $R^{3C}$ and Ring $R^{4C}$ each independently represent an aromatic hydrocarbon ring or an aromatic hetero ring, and the foregoing rings optionally have a substituent, and when a plurality of the substituents are present, they may be combined together to form a ring together with the atoms to which they are attached, and $R^{C'}$ represents a carbon atom, a silicon atom, a germanium atom, a tin atom or a lead atom, and wherein in the compound represented by the formula (C-1) in which $R^C$ is a group represented by the formula (C'-1), at least one of Ring $R^{1C}$, Ring $R^{2C}$, Ring $R^{3C}$ and Ring $R^{4C}$ has a group represented by the formula (D-1), the formula (E-1), the formula (D-A) or the formula (D-B) as the substituent,

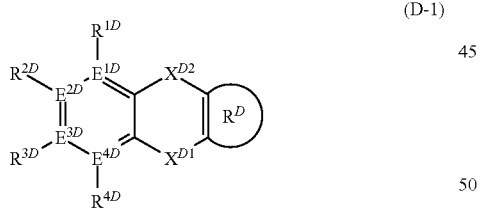

(D-1)

wherein:

Ring $R^D$ represents an aromatic hydrocarbon ring or an aromatic hetero ring, and the foregoing rings optionally have a substituent; when a plurality of the substituents are present, they may be combined together to form a ring together with the atoms to which they are attached, $X^{D1}$ and $X^{D2}$ each independently represent a single bond, an oxygen atom, a sulfur atom, a group represented by —N($R^{XD1}$)— or a group represented by —C($R^{XD2}$)$_2$—; $R^{XD1}$ and $R^{XD2}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent; a plurality of $R^{XD2}$ may be the same or different and may be combined together to form a ring together with the carbon atoms to which they are attached, $E^{1D}$, $E^{2D}$, $E^{3D}$ and $E^{4D}$ each independently represent a nitrogen atom or a carbon atom; at least one of $E^{1D}$, $E^{2D}$, $E^{3D}$ and $E^{4D}$ is a carbon atom, $R^{1D}$, $R^{2D}$, $R^{3D}$ and $R^{4D}$ each independently represent, a connecting bond, a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent; one of $R^{1D}$, $R^{2D}$, $R^{3D}$ and $R^{4D}$ is a connecting bond, when $E^{1D}$ is a nitrogen atom, $R^{1D}$ is absent, when $E^{2D}$ is a nitrogen atom, $R^{2D}$ is absent, when $E^{3D}$ is a nitrogen atom, $R^{3D}$ is absent, and when $E^{4D}$ is a nitrogen atom, $R^{4D}$ is absent, when $R^{1D}$ is a connecting bond, $E^{1D}$ is a carbon atom, when $R^{2D}$ is a connecting bond, $E^{2D}$ is a carbon atom, when $R^{3D}$ is a connecting bond, $E^{3D}$ is a carbon atom, when $R^{4D}$ is a connecting bond, $E^{4D}$ is a carbon atom, $R^{1D}$ and $R^{2D}$ may be combined together to form a ring together with the atoms to which they are attached, $R^{2D}$ and $R^{3D}$ may be combined together to form a ring together with the atoms to which they are attached, $R^{3D}$ and $R^{4D}$ may be combined together to form a ring together with the atoms to which they are attached, $R^{1D}$ and $R^{XD1}$ may be combined together to form a ring together with the atoms to which they are attached, $R^{1D}$ and $R^{XD2}$ may be combined together to form a ring together with the atoms to which they are attached, $R^{4D}$ and $R^{XD1}$ may be combined together to form a ring together with the atoms to which they are attached, and $R^{4D}$ and $R^{XD2}$ may be combined together to form a ring together with the atoms to which they are attached; the substituent which Ring $R^D$ optionally has and $R^{XD1}$ may be combined together to form a ring together with the atoms to which they are attached: the substituent which Ring $R^D$ optionally has and $R^{XD2}$ may be combined together to form a ring together with the carbon atoms to which they are attached,

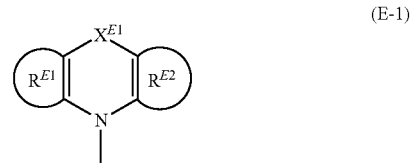

(E-1)

wherein:

Ring $R^{E1}$ and Ring $R^{E2}$ each independently represent an aromatic hydrocarbon ring or an aromatic hetero ring, and the foregoing rings optionally have a substituent; when a plurality of the substituents are present, they may be combined together to form a ring together with the atoms to which they are attached, $X^{E1}$ represents a single bond, an oxygen atom, a sulfur atom, a group represented by —N($R^{XE1}$)— or a group represented by —C($R^{XE2}$)$_2$—; $R^{XE1}$ and $R^{XE2}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent; a plurality of $R^{XE2}$ may be the same or different and may be combined together to form a ring together with the carbon atoms to which they are attached,

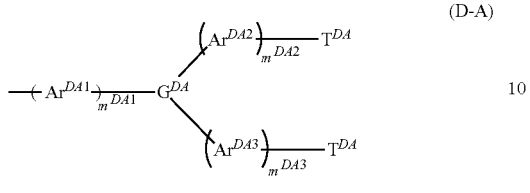
(D-A)

wherein:
$m^{DA1}$, $m^{DA2}$ and $m^{DA3}$ each independently represent an integer of 0 or more,
$G^{DA}$ represents a nitrogen atom, an aromatic hydrocarbon group or a heterocyclic group, and the foregoing groups optionally have a substituent,
$Ar^{DA1}$, $Ar^{DA2}$ and $Ar^{DA3}$ each independently represent an arylene group or a divalent heterocyclic group, and the foregoing groups optionally have a substituent; when a plurality of $Ar^{DA1}$, $Ar^{DA2}$ and $Ar^{DA3}$ are present, they may be the same or different at each occurrence,
$T^{DA}$ represents an aryl group or a monovalent heterocyclic group, and the foregoing groups optionally have a substituent; a plurality of $T^{DA}$ may be the same or different,

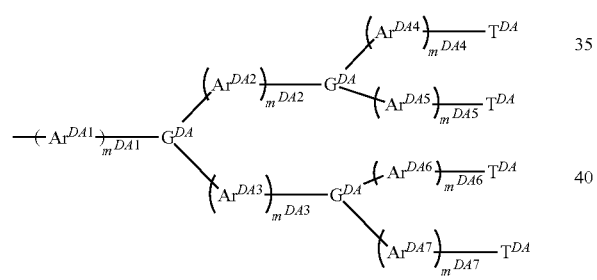
(D-B)

wherein:
$m^{DA1}$, $m^{DA2}$, $m^{DA3}$, $m^{DA4}$, $m^{DA5}$, $m^{DA6}$ and $m^{DA7}$ each independently represent an integer of 0 or more,
$G^{DA}$ represents a nitrogen atom, an aromatic hydrocarbon group or a heterocyclic group, and the foregoing groups optionally have a substituent; a plurality of $G^{DA}$ may be the same or different,
$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and the foregoing groups optionally have a substituent; when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence,
$T^{DA}$ represents an aryl group or a monovalent heterocyclic group, and the foregoing groups optionally have a substituent; a plurality of $T^{DA}$ may be the same or different.

2. The composition according to claim 1, wherein the above-described compound represented by the formula (C-1) in which $R^C$ is a group represented by the formula (C'-1) is a compound represented by the formula (C-2-1):

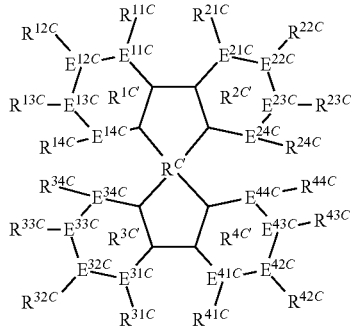
(C-2-1)

wherein:
$E^{11C}$, $E^{12C}$, $E^{13C}$, $E^{14C}$, $E^{21C}$, $E^{22C}$, $E^{23C}$, $E^{24C}$, $E^{31C}$, $E^{32C}$, $E^{33C}$, $E^{34C}$, $E^{41C}$, $E^{42C}$, $E^{43C}$ and $E^{44C}$ each independently represent a nitrogen atom or a carbon atom,
Ring $R^{1C\prime}$, Ring $R^{2C\prime}$, Ring $R^{3C\prime}$ and Ring $R^{4C\prime}$ each independently represent a benzene ring, a pyridine ring or a diazabenzene ring,
$R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent, with the provision that at least one of $R^{11C}$, $R^{12C}$, $R^{13C}$, $R^{14C}$, $R^{21C}$, $R^{22C}$, $R^{23C}$, $R^{24C}$, $R^{31C}$, $R^{32C}$, $R^{33C}$, $R^{34C}$, $R^{41C}$, $R^{42C}$, $R^{43C}$ and $R^{44C}$ is the group represented by the formula (D-1), the group represented by the formula (E-1), the group represented by the formula (D-A), or the group represented by the formula (D-B), and when $E^{11C}$ is a nitrogen atom, $R^{11C}$ is absent, when $E^{12C}$ is a nitrogen atom, $R^{12C}$ is absent, when $E^{13C}$ is a nitrogen atom, $R^{13C}$ is absent, when $E^{14C}$ is a nitrogen atom, $R^{14C}$ is absent, when $E^{21C}$ is a nitrogen atom, $R^{21C}$ is absent, when $E^{22C}$ is a nitrogen atom, $R^{22C}$ is absent, when $E^{23C}$ is a nitrogen atom, $R^{23C}$ is absent, when $E^{24C}$ is a nitrogen atom, $R^{24C}$ is absent, when $E^{31C}$ is a nitrogen atom, $R^{31C}$ is absent, when $E^{32C}$ is a nitrogen atom, $R^{32C}$ is absent, when $E^{33C}$ is a nitrogen atom, $R^{33C}$ is absent, when $E^{34C}$ is a nitrogen atom, $R^{34C}$ is absent, when $E^{41C}$ is a nitrogen atom, $R^{41C}$ is absent, when $E^{42C}$ is a nitrogen atom, $R^{42C}$ is absent, when $E^{43C}$ is a nitrogen atom, $R^{43C}$ is absent, and when $E^{44C}$ is a nitrogen atom, $R^{44C}$ is absent, and $R^{11C}$ and $R^{12C}$, $R^{12C}$ and $R^{13C}$, $R^{13C}$ and $R^{14C}$, $R^{14C}$ and $R^{34C}$, $R^{34C}$ and $R^{33C}$, $R^{33C}$ and $R^{32C}$, $R^{32C}$ and $R^{31C}$, $R^{31C}$ and $R^{41C}$, $R^{41C}$ and $R^{42C}$, $R^{42C}$ and $R^{43C}$, $R^{43C}$ and $R^{44C}$, $R^{44C}$ and $R^{24C}$, $R^{24C}$ and $R^{23C}$, $R^{23C}$ and $R^{22C}$, $R^{22C}$ and $R^{21C}$, and $R^{21C}$ and $R^{11C}$ may each be combined together to form a ring together with the carbon atoms to which they are attached.

3. The composition according to claim 2, wherein formula (C-2-1) is a compound represented by the formula (C-3-1):

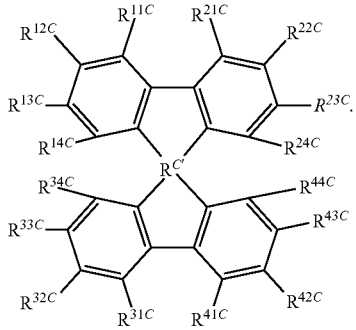
(C-3-1)

4. The composition according to claim 1, wherein at least one of the above-described two or more compounds represented by the formula (C-1) is a compound represented by the formula (C-2-2):

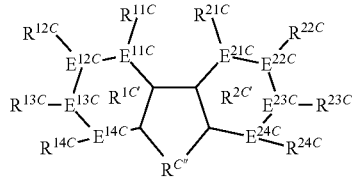
(C-2-2)

wherein:
R$^{C"}$ represents an oxygen atom or a sulfur atom,
E$^{11C}$, E$^{12C}$, E$^{13C}$, E$^{14C}$, E$^{21C}$, E$^{22C}$, E$^{23C}$ and E$^{24C}$ each independently represent a nitrogen atom or a carbon atom,
Ring R$^{1C'}$ and Ring R$^{2C'}$ each independently represent a benzene ring, a pyridine ring or a diazabenzene ring,
R$^{11C}$, R$^{12C}$, R$^{13C}$, R$^{14C}$, R$^{21C}$, R$^{22C}$, R$^{23C}$ and R$^{24C}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent, and
when E$^{11C}$ is a nitrogen atom, R$^{11C}$ is absent, when E$^{12C}$ is a nitrogen atom, R$^{12C}$ is absent, when E$^{13C}$ is a nitrogen atom, R$^{13C}$ is absent, when E$^{14C}$ is a nitrogen atom, R$^{14C}$ is absent, when E$^{21C}$ is a nitrogen atom, R$^{21C}$ is absent, when E$^{22C}$ is a nitrogen atom, R$^{22C}$ is absent, when E$^{23C}$ is a nitrogen atom, R$^{23C}$ is absent, and when E$^{24C}$ is a nitrogen atom, R$^{24C}$ is absent, and
R$^{11C}$ and R$^{12C}$, R$^{12C}$ and R$^{13C}$, R$^{13C}$ and R$^{14C}$, R$^{24C}$ and R$^{23C}$, R$^{23C}$ and R$^{22C}$, R$^{22C}$ and R$^{21C}$, and R$^{21C}$ and R$^{11C}$ may each be combined together to form a ring together with the carbon atoms to which they are attached.

5. The composition according to claim 4, wherein formula (C-2-2) is a compound represented by the formula (C-3-2):

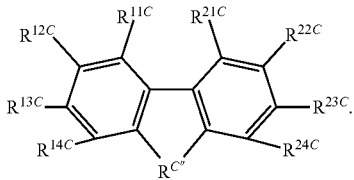
(C-3-2)

6. The composition according to claim 1, wherein the phosphorescent compound is represented by the formula (1):

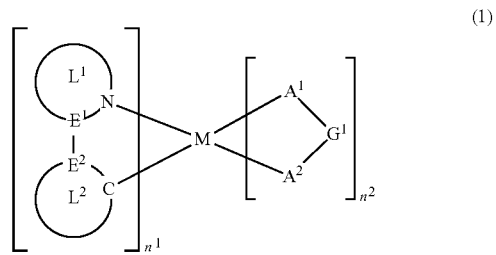
(1)

wherein:
M represents a ruthenium, a rhodium atom, a palladium atom, an iridium atom or a platinum atom,
n$^1$ represents an integer of 1 or more, n$^2$ represents an integer of 0 or more, and n$^1$+n$^2$ is 3 when M is a ruthenium, a rhodium atom or an iridium atom, while n$^1$+n$^2$ is 2 when M is a palladium atom or a platinum atom,
E$^1$ and E$^2$ each independently represent a carbon atom or a nitrogen atom, at least one of E$^1$ and E$^2$ is a carbon atom, and when a plurality of E$^1$ and E$^2$ are present, they may be the same or different at each occurrence,
Ring L$^1$ represents an aromatic hetero ring, and this aromatic hetero ring optionally has a substituent, and when a plurality of the substituents are present, they may be combined together to form a ring together with the atoms to which they are attached, and when a plurality of Ring L$^1$ are present, they may be the same or different,
Ring L$^2$ represents an aromatic hydrocarbon ring or an aromatic hetero ring, and the foregoing rings optionally have a substituent, and when a plurality of the substituents are present, they may be combined together to form a ring together with the atoms to which they are attached, and when a plurality of Ring L$^2$ are present, they may be the same or different,
the substituent which Ring L$^1$ optionally has and the substituent which Ring L$^2$ optionally has may be combined together to form a ring together with the atoms to which they are attached, and
A$^1$-G$^1$-A$^2$ represents an anionic bidentate ligand, A$^1$ and A$^2$ each independently represent a carbon atom, an oxygen atom or a nitrogen atom, and these atoms may be a ring constituent atom, G$^1$ represents a single bond or an atomic group constituting a bidentate ligand together with A$^1$ and A$^2$, and when a plurality of A$^1$-G$^1$-A$^2$ are present, they may be the same or different.

7. The composition according to claim 6, wherein the phosphorescent compound represented by the formula (1) is a phosphorescent compound represented by the formula (1-B):

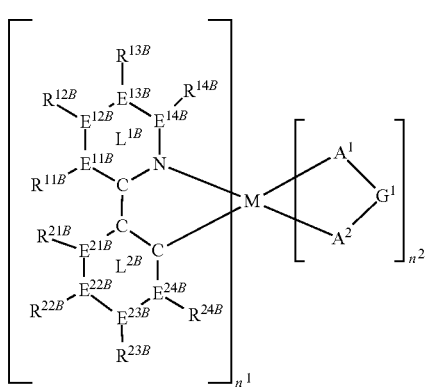

(1-B)

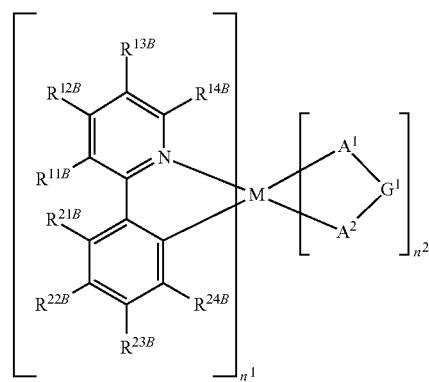

(1-B1)

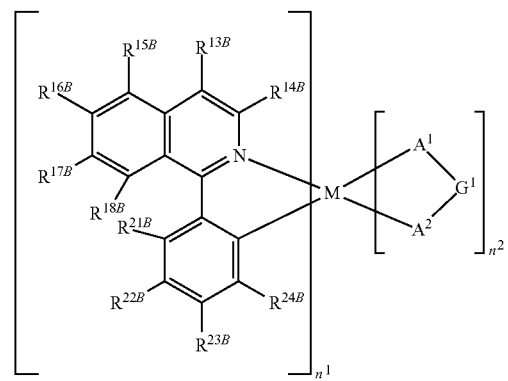

(1-B2)

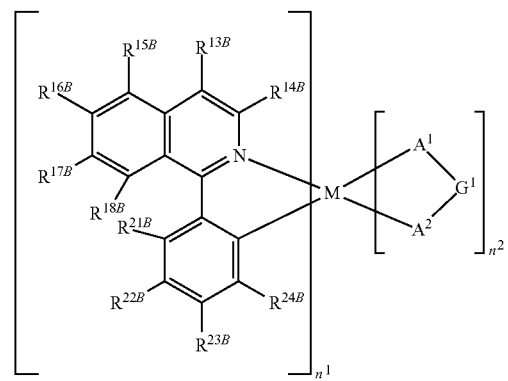

(1-B3)

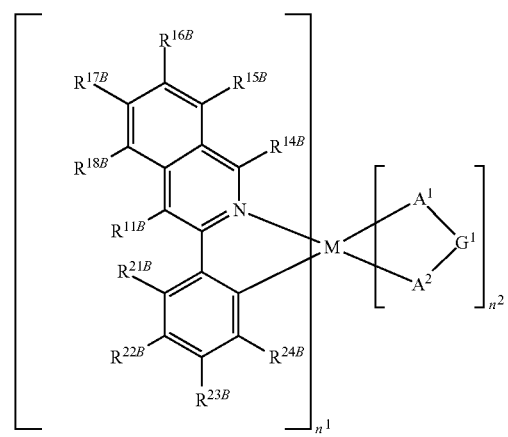

(1-B4)

wherein:
- $E^{11B}$, $E^{12B}$, $E^{13B}$, $E^{14B}$, $E^{21B}$, $E^{22B}$, $E^{23B}$ and $E^{24B}$ each independently represent a nitrogen atom or a carbon atom, and when a plurality of $E^{11B}$, $E^{12B}$, $E^{13B}$, $E^{14B}$, $E^{21B}$, $E^{22B}$, $E^{23B}$ and $E^{24B}$ are present, they may be the same or different at each occurrence, and when $E^{11B}$ is a nitrogen atom, $R^{11B}$ is absent, when $E^{12B}$ is a nitrogen atom, $R^{12B}$ is absent, when $E^{13B}$ is a nitrogen atom, $R^{13B}$ is absent, when $E^{14B}$ is a nitrogen atom, $R^{14B}$ is absent, when $E^{21B}$ is a nitrogen atom, $R^{21B}$ is absent, when $E^{22B}$ is a nitrogen atom, $R^{22B}$ is absent, when $E^{23B}$ is a nitrogen atom, $R^{23B}$ is absent, and when $E^{24B}$ is a nitrogen atom, $R^{24B}$ is absent,
- $R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent, and when a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence, and, $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ may each be combined together to form a ring together with the atoms to which they are attached,
- Ring $L^{1B}$ represents a pyridine ring or a diazabenzene ring, and
- Ring $L^{2B}$ represents a benzene ring, a pyridine ring or a diazabenzene ring.

8. The composition according to claim 7, wherein the phosphorescent compound represented by the formula (1-B) is a phosphorescent compound represented by the formula (1-B1), a phosphorescent compound represented by the formula (1-B2), a phosphorescent compound represented by the formula (1-B3), a phosphorescent compound represented by the formula (1-B4) or a phosphorescent compound represented by the formula (1-B5):

-continued (1-B5)

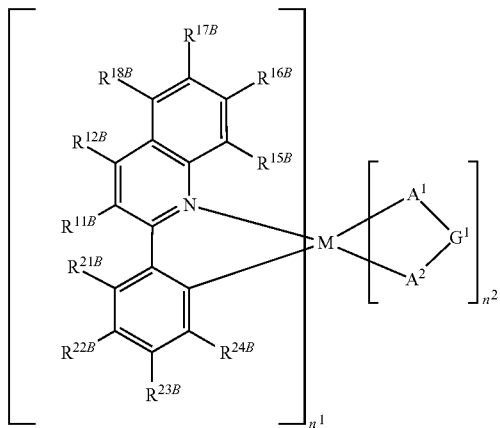

wherein:
n¹¹ and n²¹ each independently represent an integer of 1 or more, and n¹¹+n²¹ is 3 when M is a ruthenium, a rhodium atom or an iridium atom, while n¹¹+n²¹ is 2 when M is a palladium atom or a platinum atom, and $R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent, and when a plurality of $R^{15B}$, $R^{16B}$, $R^{17B}$ and $R^{15B}$ are present, they may be the same or different at each occurrence, and, $R^{13B}$ and $R^{15B}$, $R^{15B}$ and $R^{16B}$, $R^{16B}$ and $R^{17B}$, $R^{17B}$ and $R^{18B}$, and $R^{21B}$ may each be combined together to form a ring together with the atoms to which they are attached.

9. The composition according to claim 6, wherein the phosphorescent compound represented by the formula (1) is a phosphorescent compound represented by the formula (1-A):

(1-A)

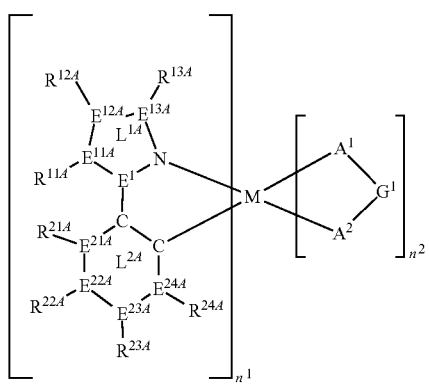

wherein:
$E^{11A}$, $E^{12A}$, $E^{13A}$, $E^{21A}$, $E^{22A}$, $E^{23A}$ and $E^{24A}$ each independently represent a nitrogen atom or a carbon atom, and when a plurality of $E^{11A}$, $E^{12A}$, $E^{13A}$, $E^{21A}$, $E^{22A}$, $E^{23A}$ and $E^{24A}$ are present, they may be the same or different at each occurrence, and when $E^{11A}$ is a nitrogen atom, $R^{11A}$ may be present or absent, when $E^{12A}$ is a nitrogen atom, $R^{12A}$ may be present or absent, when $E^{13A}$ is a nitrogen atom, $R^{13A}$ may be present or absent, when $E^{21A}$ is a nitrogen atom, $R^{21A}$ is absent, when $E^{22A}$ is a nitrogen atom, $R^{22A}$ is absent, when $E^{23A}$ is a nitrogen atom, $R^{23A}$ is absent, and when $E^{24A}$ is a nitrogen atom, $R^{24A}$ is absent, $R^{11A}$, $R^{12A}$, $R^{13A}$, $R^{21A}$, $R^{22A}$, $R^{23A}$ and $R^{24A}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent, and when a plurality of $R^{11A}$, $R^{12A}$, $R^{13A}$, $R^{21A}$, $R^{22A}$, $R^{23A}$ and $R^{24A}$ are present, they may be the same or different at each occurrence, and, $R^{11A}$ and $R^{12A}$, $R^{12A}$ and $R^{13A}$, $R^{11A}$ and $R^{21A}$, $R^{21A}$ and $R^{22A}$, $R^{22A}$ and $R^{23A}$, and $R^{23A}$ and $R^{24A}$ may each be combined together to form a ring together with the atoms to which they are attached, Ring $L^{1A}$ represents a diazole ring, and
Ring $L^{2A}$ represents a benzene ring, a pyridine ring or a diazabenzene ring.

10. The composition according to claim 9, wherein the above-described phosphorescent compound represented by the formula (1-A) is a phosphorescent compound represented by the formula (1-A4) or a phosphorescent compound represented by the formula (1-A5):

(1-A4)

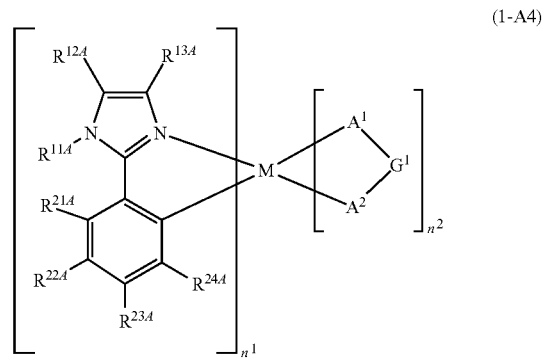

(1-A5)

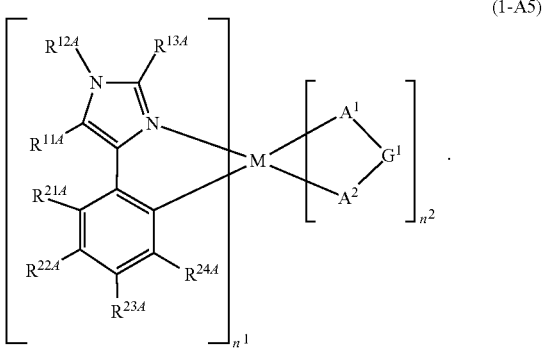

11. A light emitting device comprising the composition according to claim 1.

12. The composition according to claim 1, wherein the at least one of the two or more compounds represented by the formula (C-1) is a compound in which $R^C$ is a group represented by the formula (C'-1) has a group represented by the formula (D-1), the formula (E-1), the formula (D-A) or the formula (D-B), wherein $G^{DA}$ represents an aromatic hydrocarbon group or a heterocyclic group.

* * * * *